US011891417B2

(12) United States Patent
Gimenez-Lirola et al.

(10) Patent No.: US 11,891,417 B2
(45) Date of Patent: *Feb. 6, 2024

(54) **CHIMERIC *M. HYORHINIS* POLYPROTEIN FOR VACCINES AND DIAGNOSTICS**

(71) Applicant: Iowa State University Research Foundation, Inc., Ames, IA (US)

(72) Inventors: Luis Gabriel Gimenez-Lirola, Ames, IA (US); Bailey Arruda, Ames, IA (US)

(73) Assignee: Iowa State University Research Foundation, Inc., Ames, IA (US)

(*) Notice: Subject to any disclaimer, the term of this patent is extended or adjusted under 35 U.S.C. 154(b) by 0 days.

This patent is subject to a terminal disclaimer.

(21) Appl. No.: 18/052,434

(22) Filed: Nov. 3, 2022

(65) Prior Publication Data

US 2023/0174594 A1 Jun. 8, 2023

Related U.S. Application Data

(62) Division of application No. 16/774,474, filed on Jan. 28, 2020, now Pat. No. 11,524,982.

(60) Provisional application No. 62/797,690, filed on Jan. 28, 2019.

(51) Int. Cl.
| | | |
|---|---|---|
| *A61K 39/02* | (2006.01) | |
| *C07K 14/30* | (2006.01) | |
| *C12N 15/11* | (2006.01) | |
| *G01N 33/569* | (2006.01) | |
| *A61K 39/04* | (2006.01) | |

(52) U.S. Cl.
CPC .......... *C07K 14/30* (2013.01); *A61K 39/0241* (2013.01); *A61K 39/04* (2013.01); *C12N 15/11* (2013.01); *G01N 33/5695* (2013.01); *G01N 33/56933* (2013.01); *C07K 2319/00* (2013.01); *C12N 2310/3519* (2013.01); *C12N 2710/14041* (2013.01)

(58) Field of Classification Search
None
See application file for complete search history.

(56) References Cited

U.S. PATENT DOCUMENTS 11,524,982 B2 * 12/2022 Gimenez-Lirola .... A61K 39/04

OTHER PUBLICATIONS

Yogev et al (J.Bacteriol. Oct. 1995, 177(19): 5636-5643).*
Cleavinger et al (J.Bacteriol. 1994. 176(8): 2463-7).*
Mikayama et al. (Nov. 1993. Proc.Natl.Acad.Sci. USA, vol. 90 : 10056-10060) Nov. 1993.
Rudinger et al. (Jun. 1976. Peptide Hormones. Biol.Council. pp. 5-7) Jun. 1976.
Greenspan et al. (Nature Biotechnology 7: 936-937, 1999) 1999.
Chothia et al. (The EMBO Journal, 1986, 5/4:823-26) 1986.
Gimenez-Lirola et al., "Chimeric variant membrane surface lipoprotein (VlpA-G) as biomarker for early diagnosis of active Mycoplasma hyorhinis infection", IPVS MFR Vlp Infection biomarker, submitted Jan. 26, 2018.
Gimenez-Lirola et al., "Early detection and differential serodiagnosis of Mycoplasma hyorhinis and Mycoplasma hyosynoviae infections under experimental conditions", PLOS One, 20 pages, Oct. 7, 2019.
Gomes Neto et al., "Quantitative real-time polymerase chain reaction for detecting Mycoplasma hyosynoviae and Mycoplasma hyorhinis in pen-based oral, tonsillar, and nasal fluids", J. Vet. Sci., vol. 16(2), pp. 195-201, 2015.
Perkel, Jeffrey, "Mycoplasma Detection Kits", Life Science Articles, https://www.biocompare.com/Editorial-Articles/41799-Mycoplasma-Detection-Kits, 8 pages, Feb. 9, 2011.
Stakenborg et al., "A Multiplex PCR to Identify Porcine Mycoplasmas Present in Broth Cultures", Veterinary Research Communications, vol. 30, pp. 239-247, 2006.

* cited by examiner

*Primary Examiner* — Jennifer E Graser
(74) *Attorney, Agent, or Firm* — McKee, Voorhees & Sease, PLC

(57) ABSTRACT

The present invention is directed to novel polynucleotides, polypeptides, and polyproteins of Mycoplasma surface proteins, all of which are useful in detecting infection and for the preparation of vaccines for treating and preventing diseases in swine and other animals. Vaccines provided according to the practice of the invention are effective against Mycoplasma infections. Detection and therapeutic polyclonal and monoclonal antibodies are also a feature of the present invention. Assays, kits, systems, and nanoparticle encapsulated compositions related to the polynucleotides, polypeptides, polyproteins, antibodies or fragments, derivatives, and variants thereof are also disclosed.

6 Claims, 6 Drawing Sheets

Specification includes a Sequence Listing.

CHIMERIC *M. HYORHINIS* POLYPROTEIN FOR VACCINES AND DIAGNOSTICS

CROSS REFERENCE TO RELATED APPLICATIONS

This is a Divisional Application which claims priority to U.S. Ser. No. 16/774,474, filed Jan. 28, 2020, which application claims priority under 35 U.S.C. § 119 to Provisional Application U.S. Ser. No. 62/797,690, filed on Jan. 28, 2019, which are herein incorporated by reference in their entirety including without limitation, the specification, claims, and abstract, as well as any figures, tables, or examples thereof.

SEQUENCE LISTING

The instant application contains a sequence listing, which has been submitted in XML file format by electronic submission and is hereby incorporated by reference in its entirety. Said XML file, created on Jan. 16, 2023, is named 2023-01-16_P12846US02.xml and is 7,445 bytes in size.

FIELD OF THE INVENTION

The present invention is directed to novel nucleotide, polypeptide, and immunogenic compositions which diagnose and treat disease caused by Mycoplasma.

BACKGROUND OF THE INVENTION

*Mycoplasma hyorhinis* (MHR) and *Mycoplasma hyosynoviae* (MHS) are common commensal microorganisms in the swine upper respiratory tract and tonsils that can go systemic and cause disease. An increasing frequency of mycoplasma-associated arthritis cases have been reported in the United States over the last several years. The identification of the etiological agent by conventional methods can be difficult and time-consuming.

MHR and MHS are members of the class Mollicutes, a heterogeneous group of cell wall-less bacteria that differs significantly in their structure, habitat, and growth requirements, recognized as the smallest prokaryotic cells (0.2 and 0.8 μm) capable of self-replication. Although MHR and MHS are considered commensal microorganisms in the upper respiratory tract and tonsils of swine, they can cause disease under specific conditions through mechanisms that are poorly understood. MHS has an affinity for joints, causing arthritis most commonly in pigs of 10 weeks of age or older. MHS-related disease may affect individual pigs or become an epidemic with 10 to 50% of pigs affected before reaching market weight. MHR-associated disease has recently been identified as one of the main concerns of the U.S. pork industry, emerging as an important contributor to mortality in nursery pigs. MHR colonization has been detected in nearly every production system in which it is sought at prevalence's varying by age. Unlike MHS, MHR also causes polyserositis and arthritis.

Over the last several years, MHR and MHS have emerged as important contributors of arthritis and lameness in growing pigs. Lameness results in significant production losses due to reduced growth rate, increased mortality or culling, and antibiotic expenses. Lameness results in significant production losses due to reduced growth rate, increased mortality or culling, and antibiotic costs. Field diagnosis is mostly based on clinical signs and gross lesions, which is complicated by the presence of other bacteria (e.g., *Haemophilus parasuis*, *Streptococcus suis*, and *Erysipelothrix rhusiopathiae*) causing fibrinous lesions comparable to those produced by MHR and MHS. Therefore, there is a need for antemortem diagnostics as well as a better understanding of disease pathogenesis and the immunologic response that can help quantify the timing and effect of potential interventions of mycoplasma-associated arthritis.

A tentative diagnosis of MHR- and MHS-associated disease often can be made based on history, clinical signs and typical gross and microscopic lesions. The diagnosis should be confirmed by culture of the agent in specific media from lesions affecting serous membranes, joints, synovial fluid or other affected tissues (e.g., tonsil, lung). The use of molecular techniques such as real time PCR (qPCR) have significantly improved the detection and diagnosis of MHR and MHS-associated disease. In addition, several antibody-based methods have been used for evaluating exposure to MHR and/or for vaccine compliance at the herd level. However, although highly diagnostic specific, the identification of the etiologic agent by conventional methods can be difficult and time-consuming. Such time frames have been decreased using several PCR-based differential detection methods. Also, because their presence as commensal microbiota in the swine upper respiratory tract, PCR results must be interpreted with caution. Detection of MHR and MHS in nasal swabs, oral fluids and tonsillar scraping in apparently healthy pigs is common. Furthermore, the use of antibody detection methods for MHR and MHS for evaluating exposure and/or vaccine compliance at the population level has been investigated and reported in the literature for decades. Despite this, a well-validated, commercially available tests for MHR or MHS has never been developed. Moreover, potential serologic cross-reactivity between different swine Mycoplasma species has also been reported by different antibody assays.

Surface proteins on Mycoplasma, for example the variable surface lipoproteins (Vlp) in MHR, are subject to immune recognition and may also be used to detect Mycoplasma infected subjects. However, no such test has ever been developed.

Thus, there is a need to develop an assay for early and accurate diagnosis of MHR and MHS and to provide a treatment which may prevent or block the progression of the disease and/or reverse an established disease.

SUMMARY OF THE INVENTION

The present invention encompasses nucleotides and peptides of Mycoplasma surface proteins, antibodies to the Mycoplasma surface proteins, chimeric recombinant polypeptides and nucleotides of surface proteins, fragments, and methods of making and using the same for detection and treatment of Mycoplasma. The surface proteins, for example, may be extracted from the Mycoplasma bacterium infecting subjects, Mycoplasma grown in vitro, or made synthetically. The surface proteins may then be linked together to form chimeric surface protein polyproteins. The surface proteins alone or in chimeric polypeptides may be used as a vaccine by administrating in whole or a fragment thereof to a subject. The chimeric surface protein polyproteins may be used to detect antibodies present in a subject or be provided to a subject as a vaccine. The surface proteins alone or in chimeric polypeptide may further be used to generate polyclonal or monoclonal antibodies. Also, antibodies to Mycoplasma may be used to identify Mycoplasma surface proteins which may then be used alone or as a chimeric surface protein polyprotein for detection or treatment of one or more Mycoplasma.

Thus, the invention comprises an immunogenic composition, suitable to be used as a vaccine, which comprises one or more Mycoplasma surface proteins, preferably a chimeric recombinant polypeptide, or an immunogenic fragment thereof, one or more adjuvants, and optionally one or more excipients, in an amount effective to elicit production of neutralizing antibodies in swine. The immunogenic compositions of the invention protect swine from infection by Mycoplasma, and are effective in single doses, in two-dose programs, or in vaccination programs involving multiple doses, which may be spread apart by at least a week, and optionally at greater intervals of time, such as one to several months. It should be noted that depending on the level of epidemic threat in a particular swine population, the vaccine dose program of one, two, or multiple doses may be repeated, from time to time, as a precautionary measure. Additionally, it should be noted that vaccinating a mother sow during pregnancy will provide protection to a young piglet, via maternal transfer of antibodies and T-cells in colostrum and milk, although such protection may need to be followed up with additional vaccination doses to the piglet. Vaccination of all swine, including piglets and adults is contemplated.

The present invention includes novel nucleotide and amino acid sequences of chimeric Mycoplasma surface protein recombinant polyproteins. Vaccines provided according to the practice of the invention are effective against multiple Mycoplasma bacterium.

The present invention provides a method of treating or preventing a disease or disorder in an animal caused by infection with Mycoplasma bacterium, including disease states that are directly caused by Mycoplasma bacterium, and disease states contributed to or potentiated by Mycoplasma bacterium.

The present invention also includes the option to administer a combination vaccine, that is, a bivalent or multivalent combination of antigens, with appropriate choice of adjuvant.

Based in part upon the chimeric Mycoplasma sequences as disclosed herein, the present invention also provides a diagnostic kit for differentiating between porcine animals vaccinated with the above described Mycoplasma vaccines and porcine animals infected with field strains of Mycoplasma.

Representative embodiments of the invention include an isolated polynucleotide sequence that includes a chimeric variable surface lipoprotein (VlpA-G) recombinant nucleotide (together CVRPs) which encodes all seven of the variable surface lipoproteins (Vlp) in MHR and may be used as an immunogenic composition. This can include the whole CVRP sequences selected from the group of:

(a) the sequence of FIG. 1 or an immunogenic fragment thereof that encodes the CVRP;
(b) the complement of any sequence in (a);
(c) a polynucleotide that hybridizes with a sequence of (a) or (b) under stringent conditions defined as hybridizing to filter bound DNA in 0.5M $NaHPO_4$, 7% SDS, 1 mM EDTA at 65° C., and washing in 0.1×SSC/0.1% SDS at 68° C.
(d) a polynucleotide that is at least 70% identical to the polynucleotide of (a) or (b);
(e) a polynucleotide that is at least 80% identical to the polynucleotide of (a) or (b);
(f) a polynucleotide that is at least 90% identical to the polynucleotide of (a) or (b); and
(g) a polynucleotide that is at least 95% identical to the polynucleotide of (a) or (b)

Preferably in combination with a second heterologous sequence.

The invention further provides RNA and DNA molecules, their complements, fragments and vectors and plasmids for the expression of any such RNA or DNA polynucleotides.

The invention also provides a vaccine that comprises a polynucleotide sequence as aforementioned, and corresponding nucleotide sequences that may function as infectious clones.

The invention further provides nucleic acid sequences and resultant protein variants that have amino acid substitutions, and which reduce virulence, cause attenuation and allow the compositions to be used safely as immunogenic compositions and as vaccines.

In a further embodiment the invention includes vaccine compositions comprising a CVRP, and a carrier, wherein said composition is capable of protecting swine from challenge by Mycoplasma bacteria and preventing or treating one or more of symptoms associated with Mycoplasma bacterial infection, and wherein achievement of protection is determined by an endpoint selected from the group consisting of prevention or control of any of the Mycoplasma bacterial infection symptoms including limb lameness, polyserositis, increased fluid in the joints, and arthritis.

It is within the scope of the invention to make additional modifications in any chimeric polypeptide, such as CVRP, or the individual surface proteins described herein using known methods according to one of skill in the art, for example, homologous recombination or point mutations.

Applicants have identified individual surface proteins, surface protein compositions, and chimeric polypeptides which have high affinity to antibodies of subjects with Mycoplasma infections. In some embodiments, the antibody or fragment belongs to the IgG family. In other embodiments, the antibody or fragment belongs to the IgA family. In some embodiments, polyclonal Abs are made from injecting individual surface proteins or chimeric polypeptides into a subject and then isolating the resulting Abs from that subject. In some embodiments, the monoclonal Abs are made from hybridomas. In further embodiments, the Abs made in a different species may be modified in order to more safely administered to a subject, for example porcinized or chimeric Abs. In some embodiments, fragments of the Abs may also be used in place of Abs. In some embodiments are antibodies that bind to same epitopes as the disclosed antibodies. In yet further embodiments the antibodies are encoded by a polynucleotide.

The Abs or fragments may be used in any organism infected by Mycoplasma bacteria for detection, diagnostics, and treatment by binding to the Mycoplasma bacteria.

To enhance their use, the antibodies or fragments may be conjugated with a variety of compounds. In order to be used in a detection system, in some embodiments, the Abs or fragments are conjugated with a fluorophore or enzyme that may be detected in a system.

In other embodiments, the Abs or fragments may be loaded onto nanoparticles to enhance their effectiveness when used as a therapy. The nanoparticles may allow the Abs or fragments to avoid degradation, uptake into the wrong organ, or for enhanced passage across the blood brain barrier.

In yet another embodiment, the Abs or fragments may be provided in a kit for a detection system. The kit would include at least the antibodies or fragments for binding to Mycoplasma surface proteins in a sample and instructions for their use. In an additional embodiment, the Abs or fragments may be used in a system to detect Mycoplasma surface proteins in a sample.

In additional embodiments, the individual surface proteins, surface protein composition, or the chimeric polypeptides may be used to indirectly detect a Mycoplasma infection in a subject. The individual surface proteins, surface protein composition, or the chimeric polypeptide may be exposed to antibodies from a subject, and then antibodies bound to the individual surface proteins, surface protein composition, or the polyprotein may then be assayed. For example, the individual surface proteins, surface protein composition, or the chimeric polypeptide may be the antigen used in an indirect ELISA or other alternative immunoassay platforms, such as, but not limited to, chemiluminescence immunoassay, microbead based immunoassay, or AlphaLISA platforms. In a further embodiment, the individual surface protein, surface protein compositions, or the chimeric polypeptide may be provided in a kit. The kit may further assay the presence of the antibodies in a subject's sample.

While multiple embodiments are disclosed, still other embodiments of the present invention will become apparent to those skilled in the art from the following detailed descriptions, which show and describe illustrative embodiments of the invention. Accordingly, the figures and detailed description are to be regarded as illustrative in nature and not restrictive.

BRIEF DESCRIPTION OF THE DRAWINGS

The following drawings form part of the specification and are included to further demonstrate certain embodiments or various aspects of the invention. In some instances, embodiments of the invention can be best understood by referring to the accompanying drawings in combination with the detailed description presented herein. The description and accompanying drawings may highlight a certain specific example, or a certain aspect of the invention. However, one skilled in the art will understand that portions of the example or aspect may be used in combination with other examples or aspects of the invention.

DETAILED DESCRIPTION

Figure 1:
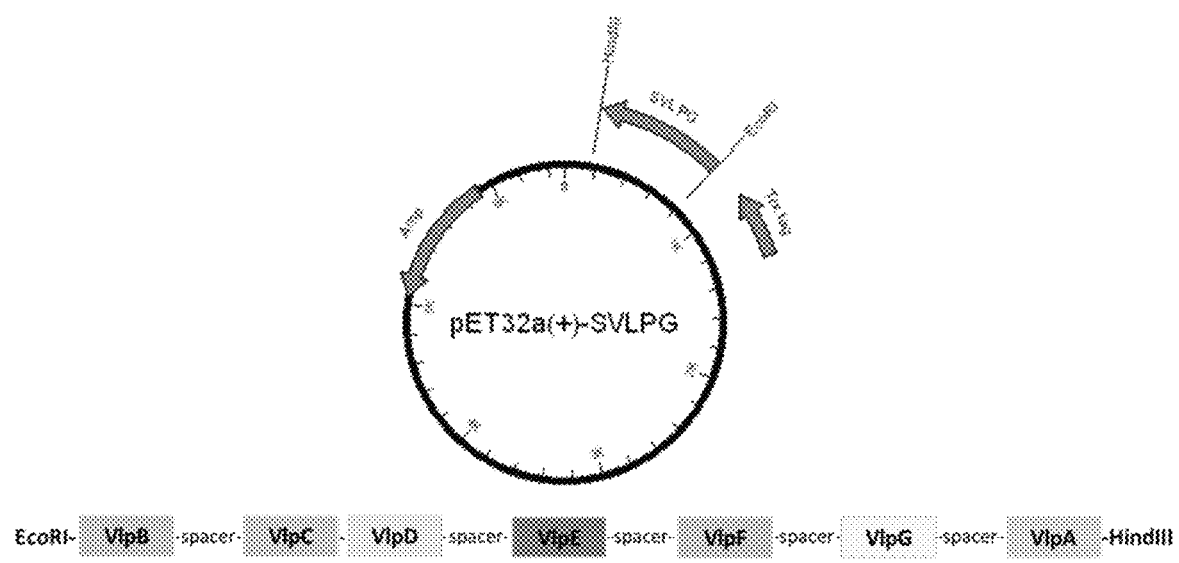
FIG. 1 is a schematic representation of the *Mycoplasma hyorhinis* chimeric VlpA-B expression plasmid.

In order to provide a clear and consistent understanding of the specification and the claims, including the scope given to such terms, the following definitions are provided. Units, prefixes, and symbols may be denoted in their SI accepted form. Unless otherwise indicated, nucleic acids are written left to right in 5' to 3' orientation; amino acid sequences are written left to right in amino to carboxy orientation, respectively. Numeric ranges are inclusive of the numbers defining the range and include each integer within the defined range. Amino acids may be referred to herein by either their commonly known three letter symbols or by the one-letter symbols recommended by the IUPAC-IUB Biochemical Nomenclature Commission.

Nucleotides, likewise, may be referred to by their commonly accepted single-letter codes. The terms defined below are more fully defined by reference to the specification as a whole.

The singular terms "a", "an", and "the" include plural referents unless context clearly indicates otherwise. Similarly, the word "or" is intended to include "and" unless the context clearly indicate otherwise. The word "or" means any one member of a particular list and also includes any combination of members of that list.

Numeric ranges recited within the specification are inclusive of the numbers defining the range and include each integer within the defined range. Throughout this disclosure, various aspects of this invention are presented in a range format. It should be understood that the description in range format is merely for convenience and brevity and should not be construed as an inflexible limitation on the scope of the invention. Accordingly, the description of a range should be considered to have specifically disclosed all the possible sub-ranges, fractions, and individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6, and decimals and fractions, for example, 1.2, 3.8, $1^{1/2}$, and 4% This applies regardless of the breadth of the range.

The phrase "and/or," when used between elements in a list, is intended to mean either (1) that only a single listed element is present, or (2) that more than one element of the list is present. For example, "A, B, and/or C" indicates that the selection may be A alone; B alone; C alone; A and B; A and C; B and C; or A, B, and C. The phrase "and/or" may be used interchangeably with "at least one of" or "one or more of" the elements in a list.

The term "adjuvant" refers to a compound that enhances the effectiveness of the vaccine and may be added to the formulation that includes the immunizing agent. Adjuvants provide enhanced immune response even after administration of only a single dose of the vaccine.

Adjuvants may include, for example, muramyl dipeptides, pyridine, aluminum hydroxide, dimethyldioctadecyl ammonium bromide (DDA), oils, oil-in-water emulsions, saponins, cytokines, and other substances known in the art. Examples of suitable adjuvants are described in U.S. Patent Application Publication No. US2004/0213817 A1. "Adjuvanted" refers to a composition that incorporates or is combined with an adjuvant.

As used herein, a "binding molecule" relates primarily to antibodies, and fragments thereof, but may also refer to other non-antibody molecules that bind to. Mycoplasma surface proteins including but not limited to hormones, receptors, ligands, major histocompatibility complex (MHC) molecules, chaperones such as heat shock proteins (HSPs) as well as cell-cell adhesion molecules such as members of the cadherin, intergrin, C-type lectin and immunoglobulin (Ig) superfamilies. Thus, for the sake of clarity only and without restricting the scope of the present invention most of the following embodiments are discussed with respect to antibodies and antibody-like molecules which represent the preferred binding molecules for the development of therapeutic and diagnostic agents.

The terms "antibody" and "immunoglobulin" are used interchangeably herein. An antibody or immunoglobulin is a Mycoplasma surface protein-binding molecule which comprises at least the variable domain of a heavy chain, and normally comprises at least the variable domains of a heavy chain and a light chain. Basic immunoglobulin structures in vertebrate systems are relatively well understood; see, e.g., Harlow et al., Antibodies: A Laboratory Manual, (Cold Spring Harbor Laboratory Press, 2nd ed. 1988).

As will be discussed in more detail below, the term "immunoglobulin" comprises various broad classes of polypeptides that can be distinguished biochemically. Those skilled in the art will appreciate that heavy chains are classified as gamma, mu, alpha, delta, or, epsilon, (γ, μ, α, δ, ε) with some subclasses among them (e.g., γ1-γ4). It is the nature of this chain that determines the "class" of the antibody as IgG, IgM, IgA IgG, or IgE, respectively. The immunoglobulin subclasses (isotypes) e.g., IgG1, IgG2, IgG3, IgG4, IgA1, etc. are well characterized and are known to confer functional specialization. Modified versions of each of these classes and isotypes are readily discernable to the skilled artisan in view of the instant disclosure and, accordingly, are within the scope of the instant invention. All immunoglobulin classes are clearly within the scope of the present invention, the following discussion will generally be directed to the IgG class of immunoglobulin molecules as merely an example. For example, with regard to IgG, a standard immunoglobulin molecule comprises two identical light chain polypeptides of molecular weight approximately 23,000 Daltons, and two identical heavy chain polypeptides of molecular weight 53,000-70,000. The four chains are typically joined by disulfide bonds in a "Y" configuration wherein the light chains bracket the heavy chains starting at the mouth of the "Y" and continuing through the variable region. IgM share the similar Y structure, however they generally resemble a pentamer or hexamer, depending on the organism of origin, of IgG joined in various ways through disulfide bonds.

Light chains are classified as either kappa or lambda (κ, λ). Each heavy chain class may be bound with either a kappa or lambda light chain. In general, the light and heavy chains are covalently bonded to each other, and the "tail" portions of the two heavy chains are bonded to each other by covalent disulfide linkages or non-covalent linkages when the immunoglobulins are generated either by hybridomas, B cells or genetically engineered host cells. In the heavy chain, the amino acid sequences run from an N-terminus at the forked ends of the Y configuration to the C-terminus at the bottom of each chain.

Both the light and heavy chains are divided into regions of structural and functional homology. The terms "constant" and "variable" are used functionally. In this regard, it will be appreciated that the variable domains of both the light ($V_L$) and heavy ($V_H$) chain portions determine antigen recognition and specificity. Conversely, the constant domains of the light chain (CL) and the heavy chain (CH1, CH2 or CH3) confer important biological properties such as secretion, transplacental mobility, Fc receptor binding, complement binding, and the like. By convention the numbering of the constant region domains increases as they become more distal from the antigen-binding site or amino-terminus of the antibody. The N-terminal portion is a variable region and at the C-terminal portion is a constant region; the CH3 and CL domains actually comprise the carboxy-terminus of the heavy and light chain, respectively.

As indicated above, the variable region allows the antibody to selectively recognize and specifically bind epitopes on antigens. That is, the $V_L$ domain and $V_H$ domain, or subset of the complementarity determining regions (CDRs), of an antibody combine to form the variable region that defines a three-dimensional antigen-binding site. This quaternary antibody structure forms the antigen-binding site present at the end of each arm of the Y. More specifically, the antigen-binding site is defined by three CDRs on each of the $V_H$ and $V_L$ chains. Any antibody or immunoglobulin fragment which contains sufficient structure to specifically bind to Mycoplasma surface proteins is denoted herein interchangeably as a "binding fragment" or an "immunospecific fragment."

In naturally occurring antibodies, an antibody comprises six hypervariable regions, sometimes called "complementarity determining regions" or "CDRs" present in each antigen-binding domain, which are short, non-contiguous sequences of amino acids that are specifically positioned to form the antigen-binding domain as the antibody assumes its three-dimensional configuration in an aqueous environment. The "CDRs" are flanked by four relatively conserved "framework" regions or "FRs" which show less inter-molecular variability. The framework regions largely adopt a β-sheet conformation and the CDRs form loops which connect, and in some cases form part of the β-sheet structure. Thus, framework regions act to form a scaffold that provides for positioning the CDRs in correct orientation by inter-chain, non-covalent interactions. The antigen-binding domain formed by the positioned CDRs defines a surface complementary to the epitope on the immunoreactive antigen. This complementary surface promotes the non-covalent binding of the antibody to its cognate epitope. The amino acids comprising the CDRs and the framework regions, respectively, can be readily identified for any given heavy or light chain variable region by one of ordinary skill in the art, since they have been precisely defined; see, "Sequences of Proteins of Immunological Interest," Kabat, E., et al., U.S. Department of Health and Human Services, (1983); and Chothia and Lesk, J. Mol. Biol., 196 (1987), 901-917, which are incorporated herein by reference in their entireties.

In the case where there are two or more definitions of a term which is used and/or accepted within the art, the definition of the term as used herein is intended to include all such meanings unless explicitly stated to the contrary. A specific example is the use of the term "complementarity determining region" (CDR) to describe the non-contiguous antigen combining sites found within the variable region of both heavy and light chain polypeptides. This particular region has been described by Kabat et al., U.S. Dept. of Health and Human Services, "Sequences of Proteins of Immunological Interest" (1983) and by Chothia and Lesk, J. Mol. Biol., 196 (1987), 901-917, which are both incorporated herein by reference, where the definitions include overlapping or subsets of amino acid residues when compared against each other. Nevertheless, application of either definition to refer to a CDR of an antibody or variants thereof is intended to be within the scope of the term as defined and used herein. The appropriate amino acid residues which encompass the CDRs as defined by each of the above cited references are set forth below in Table 1 as a comparison. The exact residue numbers which encompass a particular CDR will vary depending on the sequence and size of the CDR. Those skilled in the art can routinely determine which residues comprise a particular hypervariable region or CDR of the human IgG subtype of antibody given the variable region amino acid sequence of the antibody.

TABLE 1

CDR Definitions[1]

| | Kabat | Chothia |
|---|---|---|
| VH CDR1 | 31-35 | 26-32 |
| VH CDR2 | 50-65 | 52-58 |
| VH CDR3 | 95-102 | 95-102 |
| VL CDR1 | 24-34 | 26-32 |
| VL CDR2 | 50-56 | 50-52 |
| VL CDR3 | 89-97 | 91-96 |

[1]Numbering of all CDR definitions in TABLE 1 is according to the numbering conventions set forth by Kabat et al. (see below).

Kabat et al. also defined a numbering system for variable domain sequences that is applicable to any antibody. One of ordinary skill in the art can unambiguously-assign this system of "Kabat numbering" to any variable domain sequence, without reliance on any experimental data beyond the sequence itself. As used herein, "Kabat numbering" refers to the numbering system set forth by Kabat et al., U.S. Dept. of Health and Human Services, "Sequence of Proteins of Immunological Interest" (1983). Unless otherwise specified, references to the numbering of specific amino acid residue positions in an antibody or antigen-binding fragment, variant, or derivative thereof of the present invention are according to the Kabat numbering system.

Antibodies or antigen-binding fragments, immunospecific fragments, variants, fusion proteins, or derivatives thereof of the invention include, but are not limited to, polyclonal, monoclonal, multispecific, human, porcinized, humanized, primatized, murinized or chimeric antibodies, single chain antibodies, epitope-binding fragments, e.g., Fab, Fab' and F(ab')$_2$, Fd, Fvs, single-chain Fvs (scFvs), single-chain antibodies, disulfide-linked Fvs (sdFv), fragments comprising either a $V_L$ or $V_H$ domain, fragments produced by a Fab expression library, and anti-idiotypic (anti-Id) antibodies (including, e.g., anti-Id antibodies to antibodies disclosed herein). ScFv molecules are known in the art and are described, e.g., in U.S. Pat. No. 5,892,019. Immunoglobulin or antibody molecules of the invention can be of any type (e.g., IgG, IgE, IgM, IgD, IgA, and IgY), class (e.g., IgG1, IgG2, IgG3, IgG4, IgA1 and IgA2) or subclass of immunoglobulin molecule.

In a particularly preferred embodiment, the antibody of the present invention is not a polyclonal antibody, i.e. it substantially consists of one particular antibody species rather than being a mixture obtained froth a plasma immunoglobulin sample.

Antibody fragments, including single-chain antibodies, may comprise the variable region(s) alone or in combination with the entirety or a portion of the following: hinge region, CH1, CH2, and CH3 domains. Also included in the invention are Mycoplasma surface protein-binding fragments also comprising any combination of variable region(s) with a hinge region, CH1, CH2, and CH3 domains. Antibodies or immunospecific fragments thereof of the present invention may be from any animal origin including birds and mammals. Preferably, the antibodies are human, murine, donkey, rabbit, goat, guinea pig, camel, llama, horse, or chicken antibodies. In another embodiment, the variable region may be condricthoid in origin (e.g., from sharks).

In one aspect, the antibody of the present invention is a human monoclonal antibody isolated from a human. Optionally, the framework region of the human antibody is aligned and adopted in accordance with the pertinent human germ line variable region sequences in the database; see, e.g., Vbase (http://vbase.mrc-cpe.cam.ac.uk/) hosted by the MRC Centre for Protein Engineering (Cambridge, UK). For example, amino acids considered to potentially deviate from the true germ line sequence could be due to the PCR primer sequences incorporated during the cloning process. Compared to artificially generated human-like antibodies such as single chain antibody fragments (scFvs) from a phage displayed antibody library or xenogeneic mice the human monoclonal antibody of the present invention is characterized by (i) being obtained using the human immune response rather than that of animal surrogates, i.e. the antibody has been generated in response to natural Mycoplasma surface protein in its relevant conformation in a subject, (ii) having protected the individual or is at least significant for the presence of Mycoplasma surface proteins, and (iii) the risks of cross-reactivity against self-antigens is minimized. Thus, in accordance with the present invention the terms "human monoclonal antibody", "human monoclonal autoantibody", "human antibody" and the like are used to denote an Mycoplasma surface protein binding molecule which is of human origin, i.e. which has been isolated from a human cell such as a B cell or hybridoma thereof or the cDNA of which has been directly cloned from mRNA of a human cell, for example a human memory B cell. A human antibody is still "human" even if amino acid substitutions are made in the antibody, e.g., to improve binding characteristics. Similar terminology is used for any other species.

Antibodies derived from human immunoglobulin libraries or from animals transgenic for one or more human immunoglobulins and that do not express endogenous immunoglobulins, as described infra and, for example in, U.S. Pat. No. 5,939,598 by Kucherlapati et al., are denoted human-like antibodies in order distinguish them from truly human antibodies of the present invention.

In other aspects of the invention, an antibody may be raised in a first organism then be modified to be more similar to a different organism, such as a porcinized, murinized or humanized antibody. For example, and as used herein, the term "murinized antibody" or "murinized immunoglobulin"

refers to an antibody comprising one or more CDRs from a human antibody of the present invention; and a human framework region that contains amino acid substitutions and/or deletions and/or insertions that are based on a mouse antibody sequence. The human immunoglobulin providing the CDRs is called the "parent" or "acceptor" and the mouse antibody providing the framework changes is called the "donor". Constant regions need not be present, but if they are, they are usually substantially identical to mouse antibody constant regions, i.e. at least about 85-90%, preferably about 95% or more identical. Hence, in some embodiments, a full length murinized human heavy or light chain immunoglobulin contains a mouse constant region, human CDRs, and a substantially human framework that has a number of "murinizing" amino acid substitutions. Typically, a "murinized antibody" is an antibody comprising a murinized variable light chain and/or a murinized variable heavy chain. For example, a murinized antibody would not encompass a typical chimeric antibody, e.g., because the entire variable region of a chimeric antibody is non-mouse. A modified antibody that has been "murinized" by the process of "murinization" binds to the same antigen as the parent antibody that provides the CDRs and is usually less immunogenic in mice, as compared to the parent antibody. Conversely, a "porcinized antibody" is an antibody comprising a porcinized variable light change and/or a porcinized variable heavy chain, with a substantially murine framework.

As used herein, the term "heavy chain portion" includes amino acid sequences derived from an immunoglobulin heavy chain. A polypeptide comprising a heavy chain portion comprises at least one of: a CH1 domain, a hinge (e.g., upper, middle, and/or lower hinge region) domain, a CH2 domain, a CH3 domain, or a variant or fragment thereof. For example, a binding polypeptide for use in the invention may comprise a polypeptide chain comprising a CH1 domain; a polypeptide chain comprising a CH1 domain, at least a portion of a hinge domain, and a CH2 domain; a polypeptide chain comprising a CH1 domain and a CH3 domain; a polypeptide chain comprising a CH1 domain, at least a portion of a hinge domain, and a CH3 domain, or a polypeptide chain comprising a CH1 domain, at least a portion of a hinge domain, a CH2 domain, and a CH3 domain. In another embodiment, a polypeptide of the invention comprises a polypeptide chain comprising a CH3 domain. Further, a binding polypeptide for use in the invention may lack at least a portion of a CH2 domain (e.g., all or part of a CH2 domain). As set forth above, it will be understood by one of ordinary skill in the art that these domains (e.g., the heavy chain portions) may be modified such that they vary in amino acid sequence from the naturally occurring immunoglobulin molecule.

In certain antibodies, or antigen-binding fragments, variants, or derivatives thereof disclosed herein, the heavy chain portions of one polypeptide chain of a multimer are identical to those on a second polypeptide chain of the multimer. Alternatively, heavy chain portion-containing monomers of the invention are not identical. For example, each monomer may comprise a different target binding site, forming, for example, a bispecific antibody or diabody.

In another embodiment, the antibodies, or antigen-binding fragments, variants, or derivatives thereof disclosed herein are composed of a single polypeptide chain such as scFvs and are to be expressed intracellularly (intrabodies) for in vivo therapeutic and diagnostic applications.

The heavy chain portions of a binding polypeptide for use in the diagnostic and treatment methods disclosed herein may be derived from different immunoglobulin molecules.

For example, a heavy chain portion of a polypeptide may comprise a CH1 domain derived from an IgG1 molecule and a hinge region derived from an IgG3 molecule. In another example, a heavy chain portion can comprise a hinge region derived, in part, from an IgG1 molecule and, in part, from an IgG3 molecule. In another example, a heavy chain portion can comprise a chimeric hinge derived, in part, from an IgG1 molecule and, in part, from an IgG4 molecule.

As used herein, the term "light chain portion" includes amino acid sequences derived from an immunoglobulin light chain. Preferably, the light chain portion comprises at least one of a $V_L$ or CL domain.

The minimum size of a peptide or polypeptide epitope for an antibody is thought to be about four to five amino acids. Peptide or polypeptide epitopes preferably contain at least seven, more preferably at least nine and most preferably between at least about 15 to about 30 amino acids. Since a CDR can recognize an antigenic peptide or polypeptide in its tertiary form, the amino acids comprising an epitope need not be contiguous, and in some cases, may not even be on the same peptide chain. In the present invention, a peptide or polypeptide epitope recognized by antibodies of the present invention contains a sequence of at least 4, at least 5, at least 6, at least 7, more preferably at least 8, at least 9, at least 10, at least 15, at least 20, at least 25, or between about 15 to about 30 contiguous or non-contiguous amino acids of Mycoplasma surface proteins.

By "specifically binding", or "specifically recognizing", used interchangeably herein, it is generally meant that a binding molecule, e.g., an antibody binds to an epitope via its antigen-binding domain, and that the binding entails some complementarity between the antigen-binding domain and the epitope. According to this definition, an antibody is said to "specifically bind" to an epitope when it binds to that epitope, via its antigen-binding domain more readily than it would bind to a random, unrelated epitope. The term "specificity" is used herein to qualify the relative affinity by which a certain antibody binds to a certain epitope. For example, antibody "A" may be deemed to have a higher specificity for a given epitope than antibody "B," or antibody "A" may be said to bind to epitope "C" with a higher specificity than it has for related epitope "D".

Where present, the term "immunological binding characteristics," or other binding characteristics of an antibody with an antigen, in all of its grammatical forms, refers to the specificity, affinity, cross-reactivity, and other binding characteristics of an antibody.

By "preferentially binding", it is meant that the binding molecule, e.g., antibody specifically binds to an epitope more readily than it would bind to a related, similar, homologous, or analogous epitope. Thus, an antibody which "preferentially binds" to a given epitope would more likely bind to that epitope than to a related epitope, even though such an antibody may cross-react with the related epitope.

By way of non-limiting example, a binding molecule, e.g., an antibody may be considered to bind a first epitope preferentially if it binds said first epitope with a dissociation constant ($K_D$) that is less than the antibody's $K_D$ for the second epitope. In another non-limiting example, an antibody may be considered to bind a first antigen preferentially if it binds the first epitope with an affinity that is at least one order of magnitude less than the antibody's $K_D$ for the second epitope. In another non-limiting example, an antibody may be considered to bind a first epitope preferentially if it binds the first epitope with an affinity that is at least two orders of magnitude less than the antibody's $K_D$ for the second epitope.

In another non-limiting example, a binding molecule, e.g., an antibody may be considered to bind a first epitope preferentially if it binds the first epitope with an off rate (k(off)) that is less than the antibody's k(off) for the second epitope. In another non-limiting example, an antibody may be considered to bind a first epitope preferentially if it binds the first epitope with an affinity that is at least one order of magnitude less than the antibody's k(off) for the second epitope. In another non-limiting example, an antibody may be considered to bind a first epitope preferentially if it binds the first epitope with an affinity that is at least two orders of magnitude less than the antibody's k(off) for the second epitope. A binding molecule, e.g., an antibody or antigen-binding fragment, variant, or derivative disclosed herein may be said to hind a Mycoplasma surface protein or a fragment or variant thereof with an off rate (k(off)) of less than or equal to $5 \times 10^{-2}$ sec$^{-1}$, $10^{-2}$ sec$^{-1}$, $5 \times 10^{-3}$ sec$^{-1}$, or $10^{-3}$ sec$^{-1}$. More preferably, an antibody of the invention may be said to bind Mycoplasma surface protein or a fragment or variant thereof with an off rate (k(off)) less than or equal to $5 \times 10^{-4}$ sec$^{-1}$, $10^{-4}$ sec$^{-1}$, $5 \times 10^{-5}$ sec$^{-1}$, or $10^{-5}$ sec$^{-1}$, $5 \times 10^{-6}$ sec$^{-1}$, $10^{-6}$ sec$^{-1}$, $5 \times 10^{-7}$ sec$^{-1}$ or $10^{-7}$ sec$^{-1}$.

A binding molecule, e.g., an antibody or antigen-binding fragment, variant, or derivative disclosed herein may be said to bind Mycoplasma surface protein or a fragment or variant thereof with an on rate (k(on)) of greater than or equal to $10^3$ M$^{-1}$ sec$^{-1}$, $5 \times 10^3$ M$^{-1}$ sec$^{-1}$, $10^4$ M$^{-1}$ sec$^{-1}$ or $5 \times 10^4$ M$^{-1}$ sec$^{-1}$. More preferably, an antibody of the invention may be said Mycoplasma surface protein or a fragment or variant thereof with an on rate (k(on)) greater than or equal to $10^5$ sec$^{-1}$, $5 \times 10^5$ M$^{-1}$ sec$^{-1}$, $10^6$ M$^{-1}$ sec$^{-1}$, or $5 \times 10^6$ M$^{-1}$ sec$^{-1}$ or $10^7$ M$^{-1}$ sec$^{-1}$.

A binding molecule, e.g., an antibody is said to competitively inhibit binding of a reference antibody to a given epitope if it preferentially binds to that epitope to the extent that it blocks, to some degree, binding of the reference antibody to the epitope. Competitive inhibition may be determined by any method known in the art, for example, competition ELISA assays. An antibody may be said to competitively inhibit binding of the reference antibody to a given epitope by at least 90%, at least 80%, at least 70%, at least 60%, or at least 50%.

As used herein, the term "affinity" refers to a measure of the strength of the binding of an individual epitope with the CDR of a binding molecule, e.g., an immunoglobulin molecule; see, e.g., Harlow et al., Antibodies: A Laboratory Manual, Cold Spring Harbor Laboratory Press, 2nd ed. (1988) at pages 27-28. As used herein, the term "avidity" refers to the overall stability of the complex between a population of immunoglobulins and an antigen, that is, the functional combining strength of an immunoglobulin mixture with the antigen; see, e.g., Harlow at pages 29-34. Avidity is related to both the affinity of individual immunoglobulin molecules in the population with specific epitopes, and also the valencies of the immunoglobulins and the antigen. For example, the interaction between a bivalent monoclonal antibody and an antigen with a highly repeating epitope structure, such as a polymer, would be one of high avidity. The affinity or avidity of an antibody for an antigen can be determined experimentally using any suitable method; see, for example, Berzofsky et al., "Antibody-Antigen Interactions" In Fundamental Immunology, Paul, W. E., Ed., Raven Press New York, N.Y. (1984), Kuby, Janis Immunology, W. H. Freeman and Company New York, N.Y. (1992), and methods described herein. General techniques for measuring the affinity of an antibody for an antigen include ELISA, RIA, and surface plasmon resonance. The measured affinity of a particular antibody-antigen interaction can vary if measured under different conditions, e.g., salt concentration, pH. Thus, measurements of affinity and other antigen-binding parameters, e.g., $K_D$, IC$_{50}$, are preferably made with standardized solutions of antibody and antigen, and a standardized buffer.

Binding molecules, e.g., antibodies or antigen-binding fragments, variants or derivatives thereof of the invention may also be described or specified in terms of their cross-reactivity. As used herein, the term "cross-reactivity" refers to the ability of an antibody, specific for one antigen, to react with a second antigen; a measure of relatedness between two different antigenic substances. Thus, an antibody is cross reactive if it binds to an epitope other than the one that induced its formation. The cross-reactive epitope generally contains many of the same complementary structural features as the inducing epitope, and in some cases, may actually fit better than the original.

For example, certain antibodies have some degree of cross-reactivity, in that they bind related, but non-identical epitopes, e.g., epitopes with at least 95%, at least 90%, at least 85%, at least 80%, at least 75%, at least 70%, at least 65%, at least 60%, at least 55%, and at least 50% identity (as calculated using methods known in the art and described herein) to a reference epitope. An antibody may be said to have little or no cross-reactivity if it does not bind epitopes with less than 95%, less than 90%, less than 85%, less than 80%, less than 75%, less than 70%, less than 65%, less than 60%, less than 55%, and less than 50% identity (as calculated using methods known in the art and described herein) to a reference epitope. An antibody may be deemed "highly specific" for a certain epitope, if it does not bind any other analog, ortholog, or homolog of that epitope.

Binding molecules, e.g., antibodies or antigen-binding fragments, variants or derivatives thereof of the invention may also be described or specified in terms of their binding affinity to Mycoplasma surface protein. Preferred binding affinities include those with a dissociation constant or $K_d$ less than $5 \times 10^{-2}$ M, $10^{-2}$ M, $5 \times 10^{-3}$ M, $10^{-3}$ M, $5 \times 10^{-4}$ M, $10^{-4}$ M, $5 \times 10^{-5}$ M, $10^{-5}$ M, $5 \times 10^{-6}$ M, $10^{-6}$ M, $5 \times 10^{-7}$ M, $10^{-8}$ M, $5 \times 10^{-8}$ M, $10^{-8}$M, $5 \times 10^{-9}$ M, $10^{-9}$M, $5 \times 10^{-10}$ M, $10^{-10}$ M, $5 \times 10^{-11}$ M, $10^{-11}$ M, $5 \times 10^{-12}$ M, $10^{-12}$ M, $5 \times 10^{-13}$ M, $10^{-13}$ M, $5 \times 10^{-14}$ M, $10^{-14}$ M, $5 \times 10^{-15}$ M, or $10^{-15}$M.

As previously indicated, the subunit structures and three-dimensional configuration of the constant regions of the various immunoglobulin classes are well known. As used herein, the term "$V_H$ domain" includes the amino terminal variable domain of an immunoglobulin heavy chain and the term "CH1 domain" includes the first (most amino terminal) constant region domain of an immunoglobulin heavy chain. The CH1 domain is adjacent to the $V_H$ domain and is amino terminal to the hinge region of an immunoglobulin heavy chain molecule.

As used herein the term "CH2 domain" includes the portion of a heavy chain molecule that extends, e.g., from about residue 244 to residue 360 of an antibody using conventional numbering schemes (residues 244 to 360, Kabat numbering system; and residues 231-340, EU numbering system; see Kabat E A et al. op. cit). The CH2 domain is unique in that it is not closely paired with another domain. Rather, two N-linked branched carbohydrate chains are interposed between the two CH2 domains of an intact native IgG molecule. It is also well documented that the CH3 domain extends from the CH2 domain to the C-terminal of the IgG molecule and comprises approximately 108 residues.

As used herein, the term "hinge region" includes the portion of a heavy chain molecule that joins the CH1 domain to the CH2 domain. This hinge region comprises approximately 25 residues and is flexible, thus allowing the two N-terminal antigen-binding regions to move independently. Hinge regions can be subdivided into three distinct domains: upper, middle, and lower hinge domains; see Roux et al., J. Immunol. 161 (1998), 4083.

As used herein the term "disulfide bond" includes the covalent bond formed between two sulfur atoms. The amino acid cysteine comprises a thiol group that can form a disulfide bond or bridge with a second thiol group. In most naturally occurring IgG molecules, the CH1 and CL regions are linked by a disulfide bond and the two heavy chains are linked by two disulfide bonds at positions corresponding to 239 and 242 using the Kabat numbering system (position 226 or 229, EU numbering system). In IgM molecules, the various heavy chains making up different subunits use disulfide bonds to the other heavy chains to form an inner ring surrounded by the Y shape epitope binding regions.

As used herein, the terms "linked," "fused" or "fusion" are used interchangeably. These terms refer to the joining together of two or more elements or components; by whatever means including chemical conjugation or recombinant means. Art "in-frame fusion" refers to the joining of two or more polynucleotide open reading frames (ORFs) to form a continuous longer ORF, in a manner that maintains the correct translational reading frame of the original ORFs. Thus, a recombinant fusion protein is a single protein containing two or more segments that correspond to polypeptides encoded by the original ORFs (which segments are not normally so joined in nature). Although the reading frame is thus made continuous throughout the fused segments, the segments may be physically or spatially separated by, for example, in-frame linker sequence. For example, polynucleotides encoding the CDRs of an immunoglobulin variable region may be fused, in-frame, but be separated by a polynucleotide encoding at least one immunoglobulin framework region or additional CDR regions, as long as the "fused" CDRs are co-translated as part of a continuous polypeptide.

The term "expression" as used herein refers to a process by which a gene produces a biochemical, for example, an RNA or polypeptide. The process includes any manifestation of the functional presence of the gene within the cell including, without limitation, gene knockdown as well as both transient expression and stable expression. It includes without limitation transcription of the gene into messenger RNA (mRNA), transfer RNA (tRNA), small hairpin RNA (shRNA), small interfering RNA (siRNA) or any other RNA product, and the translation of such mRNA into polypeptide(s). If the final desired product is a biochemical, expression includes the creation of that biochemical and any precursors. Expression of a gene produces a "gene product." As used herein, a gene product can be either a nucleic acid, e.g., a messenger RNA produced by transcription of a gene, or a polypeptide which is translated from a transcript. Gene products described herein further include nucleic acids with post transcriptional modifications, e.g., polyadenylation, or polypeptides with post translational modifications, e.g., methylation, glycosylation, the addition of lipids, association with other protein subunits, proteolytic cleavage, and the like.

An "epitope" is an antigenic determinant that is immunologically active in the sense that once administered to the host, it is able to evoke an immune response of the humoral (B cells) and/or cellular type (T cells). These are particular chemical groups or peptide sequences on a molecule that are antigenic. An antibody specifically binds a particular antigenic epitope on a polypeptide. In the animal most antigens will present several or even many antigenic determinants simultaneously. Such a polypeptide may also be qualified as an immunogenic polypeptide and the epitope may be identified as described further.

The term "immunogenic fragment" as used herein refers to a polyprotein, a polypeptide, or a fragment of a polypeptide, or a nucleotide sequence encoding the same which comprises an allele-specific motif, an epitope or other sequence such that the polypeptide or the fragment will bind a major histocompatibility complex (MHC) molecule and induce a cytotoxic T lymphocyte ("CTL") response, and/or a B cell response (for example, antibody production), and/or T-helper lymphocyte response, and/or a delayed type hypersensitivity (DTH) response against the antigen from which the immunogenic polypeptide or the immunogenic fragment is derived. A DTH response is an immune reaction in which T cell-dependent macrophage activation and inflammation cause tissue injury. A DTH reaction to the subcutaneous injection of antigen is often used as an assay for cell-mediated immunity.

With the term "induction of an immunoprotective response" is meant a (humoral and/or cellular) immune response that reduces or eliminates one or more of the symptoms of disease, i.e. clinical signs, lesions, bacterial excretion and bacterial replication in tissues in the infected subject compared to a healthy control. Preferably said reduction in symptoms is statistically significant when compared to a control.

The term "polypeptide" is also intended to refer to the products of post-expression modifications of the polypeptide, including without limitation glycosylation, acetylation, phosphorylation, amidation, derivatization by known protecting/blocking groups, proteolytic cleavage, or modification by non-naturally occurring amino acids. A polypeptide may be derived from a natural biological source or produced by recombinant technology but is not necessarily translated from a designated nucleic acid sequence. It may be generated in any manner, including by chemical synthesis.

A polypeptide of the invention may be of a size of about 3 or more, 5 or more, 10 or more, 20 or more, 25 or more, 50 or more, 75 or more, 100 or more, 200 or more, 500 or more, 1,000 or more, or 2,000 or more amino acids. Polypeptides may have a defined three-dimensional structure, although they do not necessarily have such structure. Polypeptides with a defined three-dimensional structure are referred to as folded, and polypeptides which do not possess a defined three-dimensional structure, but rather can adopt a large number of different conformations and are referred to as unfolded. As used herein, the term glycoprotein refers to a protein coupled to at least one carbohydrate moiety that is attached to the protein via an oxygen-containing or a nitrogen-containing side chain of an amino acid residue, e.g., a serine residue or an asparagine residue.

By an "isolated" polypeptide or a fragment, variant, or derivative thereof is intended a polypeptide that is not in its natural milieu. No particular level of purification is required. For example, an isolated polypeptide can be removed from its native or natural environment. Recombinantly produced polypeptides and proteins expressed in host cells are considered isolated for purposed of the invention, as are native or recombinant polypeptides which have been separated, fractionated, or partially or substantially purified by any suitable technique. Also included as polypeptides of the present invention are fragments, derivatives, analogs, or variants of the foregoing polypeptides, and any combination thereof. The terms "fragment," "variant," "derivative," and "analog" when referring to antibodies or antibody polypeptides of the present invention include any polypeptides which retain at least some of the antigen-binding properties of the corresponding native binding molecule, antibody, or polypeptide. Fragments of polypeptides of the present invention include proteolytic fragments, as well as deletion fragments, in addition to specific antibody fragments discussed elsewhere herein. Variants of antibodies and antibody polypeptides of the present invention include fragments as described above, and also polypeptides with altered amino acid sequences due to amino acid substitutions, deletions, or insertions. Variants may occur naturally or be non-naturally occurring. Non-naturally occurring variants may be produced using art-known mutagenesis techniques. Variant polypeptides may comprise conservative or non-conservative amino acid substitutions, deletions or additions. Derivatives of Mycoplasma surface protein specific binding molecules, e.g., antibodies and antibody polypeptides of the present invention, are polypeptides which have been altered so as to exhibit additional features not found on the native polypeptide. Examples include fusion proteins. Variant polypeptides may also be referred to herein as "polypeptide analogs". As used herein a "derivative" of a binding molecule or fragment thereof, an antibody, or an antibody polypeptide refers to a subject polypeptide having one or more residues chemically derivatized by reaction of a functional side group. Also included as "derivatives" are those peptides which contain one or more naturally occurring amino acid derivatives of the twenty standard amino acids. For example, 4-hydroxyproline may be substituted for proline; 5-hydroxylysine may be substituted for lysine; 3-methylhistidine may be substituted for histidine; homoserine may be substituted for serine; and ornithine may be substituted for lysine.

The term "polynucleotide" is intended to encompass a singular nucleic acid as well as plural nucleic acids and refers to an isolated nucleic acid molecule or construct, e.g., messenger RNA (mRNA) or plasmid DNA (pDNA). A polynucleotide may comprise a conventional phosphodiester bond or a non-conventional bond (e.g., an amide bond, such as found in peptide nucleic acids (PNA)). The term "nucleic acid" refers to any one or more nucleic acid segments, e.g., DNA or RNA fragments, present in a polynucleotide. By "isolated" nucleic acid or polynucleotide is intended a nucleic acid molecule, DNA or RNA, which has been removed from its native environment. For example, a recombinant polynucleotide encoding an antibody contained in a vector is considered isolated for the purposes of the present invention. Further examples of an isolated polynucleotide include recombinant polynucleotides maintained in heterologous host cells or purified (partially or substantially) polynucleotides in solution. Isolated RNA molecules include in vivo or in vitro RNA transcripts of polynucleotides of the present invention. Isolated polynucleotides or nucleic acids according to the present invention further include such molecules produced synthetically. In addition, polynucleotide or a nucleic acid may be or may include a regulatory element such as a promoter, ribosome binding site, or a transcription terminator.

As used herein, a "coding region" is a portion of nucleic acid which consists of codons translated into amino acids. Although a "stop codon" (TAG, TGA, or TAA) is not translated into an amino acid, it may be considered to be part of a coding region, but any flanking sequences, for example promoters, ribosome binding sites, transcriptional terminators, introns, and the like, are not part of a coding region. Two or more coding regions of the present invention can be present in a single polynucleotide construct, e.g., on a single vector, or in separate polynucleotide constructs, e.g., on separate (different) vectors. Furthermore, any vector may contain a single coding region, or may comprise two or more coding regions, e.g., a single vector may separately encode an immunoglobulin heavy chain variable region and an immunoglobulin light chain variable region. In addition, a vector, polynucleotide, or nucleic acid of the invention may encode heterologous coding regions, either fused or unfused to a nucleic acid encoding a binding molecule, an antibody, or fragment, variant, or derivative thereof. Heterologous coding regions include without limitation specialized elements or motifs, such as a secretory signal peptide or a heterologous functional domain.

In certain embodiments, the polynucleotide or nucleic acid is DNA. In the case of DNA, a polynucleotide comprising a nucleic acid which encodes a polypeptide normally may include a promoter and/or other transcription or translation control elements operably associated with one or more coding regions. An operable association is when a coding region for a gene product, e.g., a polypeptide, is associated with one or more regulatory sequences in such a way as to place expression of the gene product under the influence or control of the regulatory sequence(s). Two DNA fragments (such as a polypeptide coding region and a promoter associated therewith) are "operably associated" or "operably linked" if induction of promoter function results in the transcription of mRNA encoding the desired gene product and if the nature of the linkage between the two DNA fragments does not interfere with the ability of the expression regulatory sequences to direct the expression of the gene product or interfere with the ability of the DNA template to be transcribed. Thus, a promoter region would be operably associated with a nucleic acid encoding a polypeptide if the promoter was capable of effecting transcription of that nucleic acid. The promoter may be a cell-specific promoter that directs substantial transcription of the DNA only in predetermined cells. Other transcription control elements, besides a promoter, for example enhancers, operators, repressors, and transcription termination signals, can be operably associated with the polynucleotide to direct cell-specific transcription. Suitable promoters and other transcription control regions are disclosed herein.

A variety of transcription control regions are known to those skilled in the art. These include, without limitation, transcription control regions which function in vertebrate cells, such as, but not limited to, promoter and enhancer segments from cytomegaloviruses (the immediate early promoter, in conjunction with intron-A), simian virus 40 (the early promoter), and retroviruses (such as Rous sarcoma virus). Other transcription control regions include those derived from vertebrate genes such as actin, heat shock protein, bovine growth hormone and rabbit β-globin, as well as other sequences capable of controlling gene expression in eukaryotic cells. Additional suitable transcription control regions include tissue-specific promoters and enhancers as well as lymphokine-inducible promoters (e.g., promoters inducible by interferons or interleukins).

Similarly, a variety of translation control elements are known to those of ordinary skill in the art. These include, but are not limited to ribosome binding sites, translation initiation and termination codons, and elements derived from picornaviruses (particularly an internal ribosome entry site, or IRES, also referred to as a CITE sequence).

In other embodiments, a polynucleotide of the present invention is RNA, for example, in the form of messenger RNA (mRNA).

Polynucleotide and nucleic acid coding regions of the present invention may be associated with additional coding regions which encode secretory or signal peptides, which direct the secretion of a polypeptide encoded by a polynucleotide of the present invention. According to the signal hypothesis, proteins secreted by mammalian cells have a signal peptide or secretory leader sequence which is cleaved from the mature protein once export of the growing protein chain across the rough endoplasmic reticulum has been initiated. Those of ordinary skill in the art are aware that polypeptides secreted by vertebrate cells generally have a signal peptide fused to the N-terminus of the polypeptide, which is cleaved from the complete or "full length" polypeptide to produce a secreted or "mature" form of the polypeptide. In certain embodiments, the native signal peptide, e.g., an immunoglobulin heavy chain or light chain signal peptide is used, or a functional derivative of that sequence that retains the ability to direct the secretion of the polypeptide that is operably associated with it. Alternatively, a heterologous mammalian signal peptide, or a functional derivative thereof, may be used. For example, the wild-type leader sequence may be substituted with the leader sequence of human tissue plasminogen activator (TPA) or mouse β-glucuronidase.

For purposes of the present invention, the nucleotide sequence of a second polynucleotide molecule (either RNA or DNA) is "homologous" to the nucleotide sequence of a first polynucleotide molecule, or has "identity" to said first polynucleotide molecule, where the nucleotide sequence of the second polynucleotide molecule encodes the same polyaminoacid as the nucleotide sequence of the first polynucleotide molecule as based on the degeneracy of the genetic code, or when it encodes a polyaminoacid that is sufficiently similar to the polyaminoacid encoded by the nucleotide sequence of the first polynucleotide molecule so as to be useful in practicing the present invention. Homologous polynucleotide sequences also refer to sense and anti-sense strands, and in all cases to the complement of any such strands. Generally, the nucleotide sequence of a second polynucleotide molecule is homologous to the nucleotide sequence of a first polynucleotide molecule if it has at least about 70% nucleotide sequence identity to the nucleotide sequence of the first polynucleotide molecule as based on the BLASTN algorithm (National Center for Biotechnology Information, otherwise known as NCBI, (Bethesda, Md., USA) of the United States National Institute of Health). In a specific example for calculations according to the practice of the present invention, reference is made to BLASTP 2.2.6 [Tatusova TA and TL Madden, "BLAST 2 sequences—a new tool for comparing protein and nucleotide sequences." (1999) FEMS Microbiol Lett. 174:247-250.]. Briefly, two amino acid sequences are aligned to optimize the alignment scores using a gap opening penalty of 10, a gap extension penalty of 0.1, and the "blosum62" scoring matrix of Henikoff and Henikoff (Proc. Nat. Acad. Sci. USA 325 89:10915-10919. 1992). The percent identity is then calculated as: Total number of identical matches X 100/divided by the length of the longer sequence+number of gaps introduced into the longer sequence to align the two sequences.

Preferably, a homologous nucleotide sequence has at least about 70% nucleotide sequence identity, even more preferably at least about 80%, 85%, 90% and 95% nucleotide sequence identity. Since the genetic code is degenerate, a homologous nucleotide sequence can include any number of "silent" base changes, i.e. nucleotide substitutions that nonetheless encode the same amino acid.

A homologous nucleotide sequence can further contain non-silent mutations, i.e. base substitutions, deletions, or additions resulting in amino acid differences in the encoded polyaminoacid, so long as the sequence remains at least about 70% identical to the polyaminoacid encoded by the first nucleotide sequence or otherwise is useful for practicing the present invention. In this regard, certain conservative amino acid substitutions may be made which are generally recognized not to inactivate overall protein function: such as in regard of positively charged amino acids (and vice versa), lysine, arginine and histidine; in regard of negatively charged amino acids (and vice versa), aspartic acid and glutamic acid; and in regard of certain groups of neutrally charged amino acids (and in all cases, also vice versa), (1) alanine and serine, (2) asparagine, glutamine, and histidine, (3) cysteine and serine, (4) glycine and proline, (5) isoleucine, leucine and valine, (6) methionine, leucine and isoleucine, (7) phenylalanine, methionine, leucine, and tyrosine, (8) serine and threonine, (9) tryptophan and tyrosine, (10) and for example tyrosine, tryptophan and phenylalanine. Amino acids can be classified according to physical properties and contribution to secondary and tertiary protein structure. A conservative substitution is thus recognized in the art as a substitution of one amino acid for another amino acid that has similar properties, and exemplary conservative substitutions may be found in WO 97/09433, page 10, published Mar. 13. 1997 (PCT/GB96/02197, filed Sep. 6, 1996. Alternatively, conservative amino acids can be grouped as described in Lehninger, (Biochemistry, Second Edition; Worth Publishers, Inc. NY:NY (1975), pp. 71-77). Protein sequences can be aligned using both Vector NTI Advance 11.5 and CLUSTAL 2.1 multiple sequence alignment. As used herein the recitation of a particular amino acid or nucleotide sequence shall include all silent mutations with respect to nucleic acid sequence and any and all conservatively modified variants with respect to amino acid sequences.

Homologous nucleotide sequences can be determined by comparison of nucleotide sequences, for example by using BLASTN, above. Alternatively, homologous nucleotide sequences can be determined by hybridization under selected conditions. For example, the nucleotide sequence of a second polynucleotide molecule is homologous to any particular polynucleotide sequence if it hybridizes to the complement of a polynucleotide under moderately stringent conditions, e.g., hybridization to filter-bound DNA in 0.5 M NaHPO$_4$, 7% sodium dodecyl sulfate (SDS), 1 mM EDTA at 65° C., and washing in 0.2×SSC/0.1% SDS at 42° C. (see Ausubel et al editors, Protocols in Molecular Biology, Wiley and Sons, 1994, pp. 6.0.3 to 6.4.10), or conditions which will otherwise result in hybridization of sequences that encode a Mycoplasma surface protein as defined below. Modifications in hybridization conditions can be empirically determined or precisely calculated based on the length and percentage of guanosine/cytosine (GC) base pairing of the probe. The hybridization conditions can be calculated as described in Sambrook, et al., (Eds.), Molecular Cloning: A Laboratory Manual, Cold Spring Harbor Laboratory Press: Cold Spring Harbor, N.Y. (1989), pp. 9.47 to 9.51.

In another embodiment, a second nucleotide sequence is homologous to any sequence of the invention if it hybridizes to the complement of any polynucleotide under highly stringent conditions, e.g. hybridization to filter-bound DNA in 0.5 M NaHPO$_4$, 7% SDS, 1 mM EDTA at 65° C., and washing in 0.1×SSC/0.1% SDS at 68° C., as is known in the art.

It is furthermore to be understood that the isolated polynucleotide molecules and the isolated RNA molecules of the present invention include both synthetic molecules and molecules obtained through recombinant techniques, such as by in vitro cloning and transcription.

As used herein, the term "polyprotein" means a polypeptide which is comprised of a series of one or more discrete subunits, wherein each subunit encodes a protein and are typically in frame along the series. The proteins may be the same or one or more of the subunits may code for a different protein. The subunits may be joined together using a linker.

"Mammals" include any warm-blooded vertebrates of the Mammalia class, including humans.

A "pharmaceutically acceptable carrier" means any conventional pharmaceutically acceptable carrier, vehicle, or excipient that is used in the art for production and administration of vaccines. Pharmaceutically acceptable carriers are typically non-toxic, inert, solid or liquid carriers.

The terms "porcine" and "swine" are used interchangeably herein and refer to any animal that is a member of the family Suidae such as, for example, a pig.

A "susceptible" host as used herein refers to a cell or an animal that can be infected by a Mycoplasma bacterium. When introduced to a susceptible animal, Mycoplasma bacterium may also induce an immunological response against the Mycoplasma bacterium or its antigen, and thereby render the animal immunity against Mycoplasma bacterium infection.

The term "vaccine" refers to an antigenic preparation used to produce immunity to a disease, in order to prevent or ameliorate the effects of infection. Vaccines are typically prepared using a combination of an immunologically effective amount of an immunogen together with an adjuvant effective for enhancing the immune response of the vaccinated subject against the immunogen.

Vaccine formulations will contain a "therapeutically effective amount" of the active ingredient, that is, an amount capable of eliciting an induction of an immunoprotective response in a subject to which the composition is administered. In the treatment and prevention of Mycoplasma bacterium disease, for example, a "therapeutically effective amount" would preferably be an amount that enhances resistance of the vaccinated subject to new infection and/or reduces the clinical severity of the disease. Such protection will be demonstrated by either a reduction or lack of symptoms normally displayed by a subject infected with Mycoplasma bacterium, a quicker recovery time and/or a lowered count of virus particles. Vaccines can be administered prior to infection, as a preventative measure against Mycoplasma bacterium. Alternatively, vaccines can be administered after the subject already has contracted a disease. Vaccines given after exposure to Mycoplasma bacterium may be able to attenuate the disease, triggering a superior immune response than the natural infection itself.

As used herein, "substantially free" may refer to any component that the composition of the invention lacks or mostly lacks. When referring to "substantially free" it is intended that the component is not intentionally added to compositions of the invention. Use of the term "substantially free" of a component allows for trace amounts of that component to be included in compositions of the invention because they are present in another component. However, it is recognized that only trace or de minimus amounts of a component will be allowed when the compositions is said to be "substantially free" of that component. Moreover, the term if a composition is said to be "substantially free" of a component, if the component is present in trace or de minimus amounts it is understood that it will not affect the effectiveness of the compositions. It is understood that if an ingredient is not expressly included herein or its possible inclusion is not stated herein, the invention composition may be substantially free of that ingredient. Likewise, the express inclusion of an ingredient allows for its express exclusion thereby allowing a composition to be substantially free of that expressly stated ingredient. For the purpose of the practice of all aspects of the invention, it is well known to those skilled in the art that there is no absolute immunological boundary in immunological assays in regard of animals that are seronegative for exposure to a particular antigen or pathogen, and those that are seropositive (having been exposed to a vaccine or pathogen). Nonetheless, those skilled in the art would recognize that in serum neutralization assays, seropositive animals would generally be detected at least up to a 1:1000 serum dilution, whereas a seronegative animal would be expected not to neutralize at a higher dilution than about 1:20 or 1:10.

Vaccine Formulations/Immunogenic Compositions

The invention also relates to an immunogenic composition, suitable to be used as a vaccine, which comprises one or more surface proteins or a chimeric polypeptide according to the invention. The immunogenic compositions according to the invention elicit a specific humoral immune response toward the surface protein, surface protein compositions, or chimeric polypeptide comprising neutralizing antibodies.

The preferred immunogenic compositions based upon the surface protein, surface protein compositions, or chimeric polypeptide disclosed herein can provide epitopes which exhibit high immunogenicity while at the same time not producing dangerous pathogenic or lethal effects.

The immunogenic compositions of this invention are not, however, restricted to any particular type or method of preparation. These include, but are not limited to, infectious DNA vaccines (i.e., using plasmids, vectors or other conventional carriers to directly inject DNA into a subject, such as a pig), subunit vaccines, genetically engineered vaccines, etc. These vaccines are prepared by standard methods known in the art.

Additional genetically engineered vaccines, which are desirable in the present invention, are produced by techniques known in the art. Such techniques involve, but are not limited to, further manipulation of recombinant DNA, modification of or substitutions to the amino acid sequences of the recombinant proteins and the like.

Genetically engineered vaccines based on recombinant DNA technology are made, for instance, by identifying alternative portions of the Mycoplasma genes encoding proteins, such as surface proteins, responsible for inducing a stronger immune or protective response in a subject (e.g., proteins derived from VlpA, VlpB, VlpC, VlpD, etc.). Various subtypes or isolates of the Mycoplasma protein genes can be subjected to the DNA-shuffling method. The resulting heterogeneous chimeric viral proteins can be used as broad protecting subunit vaccines.

Alternatively, such chimeric Mycoplasma genes or immuno-dominant fragments can be cloned into standard protein expression vectors, such as the baculovirus vector, and used to infect appropriate host cells (see, for example, O'Reilly et al., "Baculovirus Expression Vectors: A Lab Manual," Freeman & Co., 1992). The host cells are cultured, thus expressing the desired vaccine antigen proteins, which can be purified to the desired extent and formulated into a suitable vaccine product.

If the surface proteins, surface protein compositions, or chimeric polypeptides retain any undesirable natural abilities of causing disease, it is also possible to pinpoint the nucleotide sequences in the Mycoplasma gene responsible for any residual virulence, and genetically engineer the Mycoplasma avirulent through, for example, site-directed mutagenesis or homologous recombination, such as CRISPR, TALEN, or Zinc fingers. Genetic engineering is able to add, delete or change one or more nucleotides (see, for instance, Zoller et al., DNA 3:479-488, 1984). An oligonucleotide is synthesized containing the desired mutation and annealed to a portion of single stranded DNA. The hybrid molecule, which results from that procedure, is employed to transform bacteria. Then double-stranded DNA, which is isolated containing the appropriate mutation, is used to produce full-length DNA by ligation to a restriction fragment of the latter that is subsequently transfected into a suitable cell culture. Ligation of the genes into the suitable vector for transfer may be accomplished through any standard technique known to those of ordinary skill in the art. Transfection of the vector into host cells for the production of the antigen may be done using any of the conventional methods such as calcium-phosphate or DEAE-dextran mediated transfection, electroporation, protoplast fusion and other well-known techniques (e.g., Sambrook et al., "Molecular Cloning: A Laboratory Manual," Cold Spring Harbor Laboratory Press, 1989). The cloned antigen then exhibits the desired mutation. Alternatively, two oligonucleotides can be synthesized which contain the appropriate mutation. These may be annealed to form double-stranded DNA that can be inserted in the vector to produce the antigen.

An immunologically effective amount of the vaccines of the present invention is administered to a pig in need of protection against viral infection. The immunologically effective amount or the immunogenic amount that inoculates the pig can be easily determined or readily titrated by routine testing. An effective amount is one in which a sufficient immunological response to the vaccine is attained to protect the pig exposed to a Mycoplasma bacterium. Preferably, the pig is protected to an extent in which one to all of the adverse physiological symptoms or effects of the viral disease are significantly reduced, ameliorated or totally prevented.

Vaccines of the present invention can be formulated following accepted convention to include acceptable carriers for animals, such as standard buffers, stabilizers, diluents, preservatives, and/or solubilizers, and can also be formulated to facilitate sustained release. Diluents include water, saline, dextrose, ethanol, glycerol, and the like. Additives for isotonicity include sodium chloride, dextrose, mannitol, sorbitol, and lactose, among others. Stabilizers include albumin, among others. Other suitable vaccine vehicles and additives, including those that are particularly useful in formulating modified live vaccines, are known or will be apparent to those skilled in the art. See, e.g., Remington's Pharmaceutical Science, 18th ed., 1990, Mack Publishing, which is incorporated herein by reference.

Vaccines of the present invention may further comprise one or more additional immunomodulatory components such as, e.g., an adjuvant or cytokine, among others. Non-limiting examples of adjuvants that can be used in the vaccine of the present invention include the RIBI adjuvant system (Ribi Inc., Hamilton, Mont.), alum, mineral gels such as aluminum hydroxide gel, oil-in-water emulsions, water-in-oil emulsions such as, e.g., Freund's complete and incomplete adjuvants, Block copolymer (CytRx, Atlanta Ga.), QS-21 (Cambridge Biotech Inc., Cambridge Mass.), SAF-M (Chiron, Emeryville Calif), AMPHIGEN® adjuvant, saponin, Quil A or other saponin fraction, monophosphoryl lipid A, ionic polysaccharides, and Avridine lipid-amine adjuvant. Non-limiting examples of oil-in-water emulsions useful in the vaccine of the invention include modified SEAM62 and SEAM 1/2 formulations. Modified SEAM62 is an oil-in-water emulsion containing 5% (v/v) squalene (Sigma), 1% (v/v) SPAN® 85 detergent (ICI Surfactants), 0.7% (v/v) TWEEN® 80 detergent (ICI Surfactants), 2.5% (v/v) ethanol, 200 µg/ml Quil A, 100 µg/ml cholesterol, and 0.5% (v/v) lecithin. Modified SEAM ½ is an oil-in-water emulsion comprising 5% (v/v) squalene, 1% (v/v) SPAN® 85 detergent, 0.7% (v/v) Tween 80 detergent, 2.5% (v/v) ethanol, 100 µg/ml Quil A, and 50 µg/ml cholesterol. Other immunomodulatory agents that can be included in the vaccine include, e.g., one or more interleukins, interferons, or other known cytokines.

Additional adjuvant systems permit for the combination of both T-helper and B-cell epitopes, resulting in one or more types of covalent T-B epitope linked structures, with may be additionally lipidated, such as those described in WO2006/084319, WO2004/014957, and WO2004/014956.

Adjuvant Components

The vaccine compositions of the invention may or may not include adjuvants. Adjuvants that may be used for oral administration include those based on CT-like immune modulators (rmLT, CT-B, i.e. recombinant-mutant heat labile toxin of *Escherichia coli*, Cholera toxin-B subunit); or via encapsulation with polymers and alginates, or with mucoadhesives such as chitosan, or via liposomes. Adjuvants, if present, may be provided as emulsions, more commonly if non-oral administration is selected.

In one example, adjuvant components are provided from a combination of lecithin in light mineral oil, and also an aluminum hydroxide component.

As is understood in the art, the order of addition of components can be varied to provide the equivalent final vaccine composition. The vaccinate compositions of the invention permit variation in all of the ingredients, such that the total dose of antigen may be varied by a factor of 100 (up or down), and most preferably by a factor of 10 or less (up or down). Similarly, surfactant concentrations (such as Tween or Span) may be varied by up to a factor of 10, independently of each other, or they may be deleted entirely, with replacement by appropriate concentrations of similar materials, as is well understood in the art.

According to the practice of the invention, the oil used in the adjuvant formulations of the instant invention is preferably a mineral oil. As used herein, the term "mineral oil" refers to a mixture of liquid hydrocarbons obtained from petrolatum via a distillation technique. The term is synonymous with "liquefied paraffin", "liquid petrolatum" and "white mineral oil." The term is also intended to include "light mineral oil," i.e., oil which is similarly obtained by distillation of petrolatum, but which has a slightly lower specific gravity than white mineral oil. See, e.g., Remington's Pharmaceutical Sciences, 18th Edition (Easton, Pa.: Mack Publishing Company, 1990, at pages 788 and 1323). Mineral oil can be obtained from various commercial sources, for example, J. T. Baker (Phillipsburg, Pa.), USB Corporation (Cleveland, Ohio). Preferred mineral oil is light mineral oil commercially available under the name DRAKEOL®.

Typically, the oily phase is present in an amount from 50% to 95% by volume; preferably, in an amount of greater than 50% to 85%; more preferably, in an amount from greater than 50% to 60%, and more preferably in the amount of greater than 50-52% v/v of the vaccine composition. The oily phase includes oil and emulsifiers (e.g., SPAN® 80, TWEEN® 80 etc), if any such emulsifiers are present.

Non-natural, synthetic emulsifiers suitable for use in the adjuvant formulations of the present invention also include sorbitan-based non-ionic surfactants, e.g. fatty-acid-substituted sorbitan surfactants (commercially available under the name SPAN® or ARLACEL®), fatty acid esters of polyethoxylated sorbitol (TWEEN®), polyethylene glycol esters of fatty acids from sources such as castor oil (EMULFOR®); polyethoxylated fatty acid (e.g., stearic acid available under the name SIMULSOL® M-53), polyethoxylated isooctylphenol/formaldehyde polymer (TYLOXAPOL®), polyoxyethylene fatty alcohol ethers (BRIJ®); polyoxyethylene nonphenyl ethers (TRITON® N), polyoxyethylene isooctylphenyl ethers (TRITON® X). Preferred synthetic surfactants are the surfactants available under the name SPAN® and TWEEN®, such as TWEEN®-80 (Polyoxyethylene (20) sorbitan monooleate) and SPAN®-80 (sorbitan monooleate). Generally speaking, the emulsifier(s) may be present in the vaccine composition in an amount of 0.01% to 40% by volume, preferably, 0.1% to 15%, more preferably 2% to 10%.

In an alternative embodiment of the invention, the final vaccine composition contains SP-Oil® and Rehydragel® LV as adjuvants (or other Rehydragel® or Alhydrogel® products), with preferable amounts being about 5-20% SP-Oil (v/v) and about 5-15% Rehydragel LV (v/v), and with 5% and 12%, respectively, being most preferred amounts. In this regard it is understood that % Rehydragel refers to percent dilution from the stock commercial product. (SP-Oil® is a fluidized oil emulsion with includes a polyoxyethylene-polyoxypropylene block copolymer (Pluronic® L121, BASF Corporation, squalene, polyoxyethylene sorbitan monooleate (Tween®80, ICI Americas) and a buffered salt solution.)

It should be noted that the present invention may also be successfully practiced using wherein the adjuvant component is only Amphigen®.

In another embodiment of the invention, the final vaccine composition contains TXO as an adjuvant; TXO is generally described in WO 2015/042369. All TXO compositions disclosed therein are useful in the preparation of vaccines of the invention. In TXO, the immunostimulatory oligonucleotide ("T"), preferably an ODN, preferably containing a palindromic sequence, and optionally with a modified backbone, is present in the amount of 0.1 to 5 ug per 50 ul of the vaccine composition (e.g., 0.5-3 ug per 50 ul of the composition, or more preferably 0.09-0.11 ug per 50 ul of the composition). A preferred species thereof is SEQ ID NO: 8 as listed (page 17) in the WO2015/042369 publication (PCT/US2014/056512). The polycationic carrier ("X") is present in the amount of 1-20 ug per 50 ul (e.g., 3-10 ug per 50 ul, or about 5 ug per 50 ul). Light mineral oil ("O") is also a component of the TXO adjuvant.

In certain embodiments, TXO adjuvants are prepared as follows:
a) Sorbitan monooleate, MPL-A and cholesterol are dissolved in light mineral oil. The resulting oil solution is sterile filtered;
b) The immunostimulatory oligonucleotide, Dextran DEAE and Polyoxyethylene (20) sorbitan monooleate are dissolved in aqueous phase, thus forming the aqueous solution; and
c) The aqueous solution is added to the oil solution under continuous homogenization thus forming the adjuvant formulation TXO.

All the adjuvant compositions of the invention can be used with any of the Mycoplasma polypeptides covered by the present Specification.

Additional adjuvants useful in the practice of the invention include Prezent-A (see generally United States published patent application US20070298053; and "QCDCRT" or "QCDC"-type adjuvants (see generally United States published patent application US20090324641.

Excipients

The immunogenic and vaccine compositions of the invention can further comprise pharmaceutically acceptable carriers, excipients and/or stabilizers (see e.g. Remington: The Science and practice of Pharmacy, 2005, Lippincott Williams), in the form of lyophilized formulations or aqueous solutions. Acceptable carriers, excipients, or stabilizers are nontoxic to recipients at the dosages and concentrations, and may comprise buffers such as phosphate, citrate, and other organic acids; antioxidants including ascorbic acid and methionine; preservatives (such as Mercury((o-carboxyphenyl)thio)ethyl sodium salt (THIOMERSAL), octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrans; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG), TWEEN or PLURONICS.

Vaccines of the present invention can optionally be formulated for sustained release of the proteins, infectious DNA molecule, plasmid, or viral vector of the present invention. Examples of such sustained release formulations include virus, infectious DNA molecule, plasmid, or viral vector in combination with composites of biocompatible polymers, such as, e.g., poly (lactic acid), poly (lactic-co-glycolic acid), methylcellulose, hyaluronic acid, collagen and the like. The structure, selection and use of degradable polymers in drug delivery vehicles have been reviewed in several publications, including A. Domb et al., 1992, Polymers for Advanced Technologies 3: 279-292, which is incorporated herein by reference. Additional guidance in selecting and using polymers in pharmaceutical formulations can be found in texts known in the art, for example M. Chasin and R. Langer (eds), 1990, "Biodegradable Polymers as Drug Delivery Systems" in: Drugs and the Pharmaceutical Sciences, Vol. 45, M. Dekker, N.Y., which is also incorporated herein by reference. Alternatively, or additionally, the virus, plasmid, or viral vector can be microencapsulated to improve administration and efficacy. Methods for microencapsulating antigens are well-known in the art, and include techniques described, e.g., in U.S. Pat. Nos. 3,137, 631; 3,959,457; 4,205,060; 4,606,940; 4,744,933; 5,132, 117; and International Patent Publication WO 95/28227, all of which are incorporated herein by reference.

Liposomes can also be used to provide for the sustained release of virus, plasmid, viral protein, or viral vector. Details concerning how to make and use liposomal formulations can be found in, among other places, U.S. Pat. Nos. 4,016,100; 4,452,747; 4,921,706; 4,927,637; 4,944,948; 5,008,050; and U.S. Pat. No. 5,009,956, all of which are incorporated herein by reference.

An effective amount of any of the above-described vaccines can be determined by conventional means, starting with a low dose of protein, viral protein plasmid, or viral vector, and then increasing the dosage while monitoring the effects. An effective amount may be obtained after a single administration of a vaccine or after multiple administrations of a vaccine. Known factors can be taken into consideration when determining an optimal dose per animal. These include the species, size, age and general condition of the animal, the presence of other drugs in the animal, and the like. The actual dosage is preferably chosen after consideration of the results from other animal studies.

One method of detecting whether an adequate immune response has been achieved is to determine seroconversion and antibody titer in the animal after vaccination. The timing of vaccination and the number of boosters, if any, will preferably be determined by a doctor or veterinarian based on analysis of all relevant factors, some of which are described above. The effective dose amount of virus, protein, infectious nucleotide molecule, plasmid, or viral vector, of the present invention can be determined using known techniques, taking into account factors that can be determined by one of ordinary skill in the art such as the weight of the animal to be vaccinated. For example, the dose amount of virus of the present invention in a vaccine of the present invention preferably ranges from about $10^1$ to about $10^9$ pfu (plaque forming units), more preferably from about $10^2$ to about $10^8$ pfu, and most preferably from about $10^3$ to about $10^7$ pfu. The dose amount of a plasmid of the present invention in a vaccine of the present invention preferably ranges from about 0.1 μg to about 100 mg, more preferably from about 1 μg to about 10 mg, even more preferably from about 10 μg to about 1 mg. The dose amount of an infectious DNA molecule of the present invention in a vaccine of the present invention preferably ranges from about 0.1 μg to about 100 mg, more preferably from about 1 μg to about 10 mg, even more preferably from about 10 μg to about 1 mg. The dose amount of a viral vector of the present invention in a vaccine of the present invention preferably ranges from about $10^1$ pfu to about $10^9$ pfu, more preferably from about $10^2$ pfu to about $10^8$ pfu, and even more preferably from about $10^3$ to about $10^7$ pfu. A suitable dosage size ranges from about 0.5 ml to about 10 ml, and more preferably from about 1 ml to about 5 ml.

Suitable doses for bacterial protein or peptide vaccines according to the practice of the present invention range generally from 1 to 50 micrograms per dose, or higher amounts as may be determined by standard methods, with the amount of adjuvant to be determined by recognized methods in regard of each such substance. In a preferred example of the invention relating to vaccination of swine, an optimum age target for the animals is between about 1 and 21 days, which at pre-weening, may also correspond with other scheduled vaccinations such as against *Mycoplasma hyopneumoniae*. Additionally, a preferred schedule of vaccination for breeding sows would include similar doses, with an annual revaccination schedule.

Dosing

A preferred clinical indication is for treatment, control and prevention in both breeding sows and gilts pre-farrowing, followed by vaccination of piglets. In a representative example (applicable to both sows and gilts), two 2-ML doses of vaccine will be used, although of course, actual volume of the dose is a function of how the vaccine is formulated, with actual dosing amounts ranging from 0.1 to 5ML, taking also into account the size of the animals. Single dose vaccination is also appropriate.

The first dose may be administered as early as pre-breeding to 5-weeks pre-farrowing, with the second dose administered preferably at about 1-3 weeks pre-farrowing. Booster doses can be given two to four weeks prior to any subsequent farrowings. Intramuscular vaccination (all doses) is preferred, although one or more of the doses could be given subcutaneously. Oral administration is also preferred. Vaccination may also be effective in naive animals, and non-naive animals as accomplished by planned or natural infections.

In a further preferred example, the sow or gilt is vaccinated intramuscularly or orally at 5-weeks pre-farrowing and then 2-weeks pre-farrowing. Under these conditions, a protective immune response can be demonstrated in Mycoplasma-negative vaccinated sows in that they developed antibodies (measured via fluorescent focal neutralization titer from serum samples) with neutralizing activity, and these antibodies were passively transferred to their piglets. The protocols of the invention are also applicable to the treatment of already seropositive sows and gilts, and also piglets and boars. Booster vaccinations can also be given, and these may be via a different route of administration. Although it is preferred to re-vaccinate a mother sow prior to any subsequent farrowings, the vaccine compositions of the invention nonetheless can still provide protection to piglets via ongoing passive transfer of antibodies, even if the mother sow was only vaccinated in association with a previous farrowing.

It should be noted that piglets may then be vaccinated as early as Day 1 of life. For example, piglets can be vaccinated at Day 1, with or without a booster dose at 3 weeks of age, particularly if the parent sow, although vaccinated pre-breeding, was not vaccinated pre-farrowing. Piglet vaccination may also be effective if the parent sow was previously not naive either due to natural or planned infection. Vaccination of piglets when the mother has neither been previously exposed to the virus, nor vaccinated pre-farrowing may also effective. Boars (typically kept for breeding purposes) should be vaccinated once every 6 months. Variation of the dose amounts is well within the practice of the art. It should be noted that the vaccines of the present invention are safe for use in pregnant animals (all trimesters) and neonatal swine. The vaccines of the invention are attenuated to a level of safety (i.e. no mortality, only transient mild clinical signs or signs normal to neonatal swine) that is acceptable for even the most sensitive animals again including neonatal pigs. Of course, from a standpoint of protecting swine herds both from Mycoplasma epidemics and persistent low-level Mycoplasma occurrence, programs of sustained sow vaccination are of great importance. It will be appreciated that sows or gilts immunized with Mycoplasma surface proteins, surface protein compositions, or chimeric polypeptides will passively transfer immunity to piglets, including Mycoplasma-specific IgA, which will protect piglets from Mycoplasma-associated disease and mortality. Generally, pigs that are immunized with Mycoplasma surface proteins, surface protein compositions, or chimeric polypeptides will aid in stopping or controlling the Mycoplasma transmission cycle.

It should also be noted that animals vaccinated with the vaccines of the invention are also immediately safe for human consumption, without any significant slaughter withhold, such as 21 days or less.

When provided therapeutically, the vaccine is provided in an effective amount upon the detection of a sign of actual infection. A composition is said to be "pharmacologically acceptable" if its administration can be tolerated by a recipient. Such a composition is said to be administered in a "therapeutically or prophylactically effective amount" if the amount administered is physiologically significant.

At least one vaccine or immunogenic composition of the present invention can be administered by any means that achieve the intended purpose, using a pharmaceutical composition as described herein. For example, route of administration of such a composition can be by parenteral, oral, oronasal, intranasal, intratracheal, topical, subcutaneous, intramuscular, transcutaneous, intradermal, intraperitoneal, intraocular, and intravenous administration. In one embodiment of the present invention, the composition is administered by intramuscularly. Parenteral administration can be by bolus injection or by gradual perfusion over time. Any suitable device may be used to administer the compositions, including syringes, droppers, needleless injection devices, patches, and the like. The route and device selected for use will depend on the composition of the adjuvant, the antigen, and the subject, and such are well known to the skilled artisan. Administration that is oral, or alternatively, subcutaneous, is preferred. Oral administration may be direct, via water, or via feed (solid or liquid feed). When provided in liquid form, the vaccine may be lyophilized with reconstitution, provided as a paste, for direct addition to feed (mix in or top dress) or otherwise added to water or liquid feed.

Polypeptides, Polynucleotides, and Polyproteins of the Invention

Individual or multiple surface proteins of *Mycoplasma* species may be used to present antigens for the various embodiments herein. For example, one or more surface proteins from a single *Mycoplasma* species may be used to present antigens, or one or more surface proteins from multiple *Mycoplasma* species may be used to present antigens. The one or more surface proteins may be used individually, as a mixture, or as a single chimeric polypeptide. If the one or more surface proteins are made into a chimeric polypeptide, they may be separated by a linker. A polynucleotide encoding the chimeric polypeptide will preferably have the individual proteins encoded in frame.

Polynucleotides can be composed of any polyribonucleotide or polydeoxyribonucleotide, which may be unmodified RNA or DNA or modified RNA or DNA. For example, a polynucleotide encoding an antibody, or antigen-binding fragment, variant, or derivative thereof can be composed of single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, a polynucleotide encoding an antibody, or antigen-binding fragment, variant, or derivative thereof can be composed of triple-stranded regions comprising RNA or DNA or both RNA and DNA. A polynucleotide encoding an antibody, or antigen-binding fragment, variant, or derivative thereof may also contain one or more modified bases or DNA or RNA backbones modified for stability or for other reasons. "Modified" bases include, for example, tritylated bases and unusual bases such as inosine. A variety of modifications can be made to DNA and RNA; thus, "polynucleotide" embraces chemically, enzymatically, or metabolically modified forms.

Representative embodiments of the invention include an isolated polynucleotide sequence that comprises a polynucleotide selected from the group consisting of: (a) the sequence as depicted in FIG. 1; or a fragment thereof; (b) the complement of any sequence in (a); (c) a polynucleotide that hybridizes with a sequence of (a) or (b) under stringent conditions defined as hybridizing to filter bound DNA in 0.5M $NaHPO_4$, 7% SDS, 1 mM EDTA at 65° C., and washing in 0.1×SSC/0.1% SDS at 68° C.; (d) a polynucleotide that is at least 70% identical to the polynucleotide of (a) or (b); (e) a polynucleotide that is at least 80% identical to the polynucleotide of (a) or (b); (f) a polynucleotide that is at least 90% identical to the polynucleotide of (a) or (b); and (g) a polynucleotide that is at least 95% identical to the polynucleotide of (a) or (b). In a preferred embodiment the polynucleotide includes a second heterologous polynucleotide sequence.

The invention also provides a polypeptide encoded by one or more of the surface proteins of Mycoplasma, combinations thereof, or a polypeptide that is at least 90% identical thereto, domains thereof, or to a fragment thereof, including the option that additional otherwise identical amino acids are replaced by conservative substitutions. The polypeptides may also be isolated from Mycoplasma bacterium from Mycoplasma infected animals or isolated from Mycoplasma grown in vitro.

The invention also provides a polypeptide encoded by one or more of the surface proteins of Mycoplasma, combinations thereof of the invention or a polypeptide that is at least 90% identical thereto, or to a fragment thereof, including the option that additional otherwise identical amino acids are replaced by conservative substitutions.

The invention also provides for polynucleotides encoding antibodies, or antigen-binding fragments, variants, or derivatives thereof.

An isolated polynucleotide encoding a non-natural variant of a polypeptide can be created by introducing one or more nucleotide substitutions, additions or deletions into the nucleotide sequence of the original polypeptide such that one or more amino acid substitutions, additions or deletions are introduced into the encoded protein. Mutations may be introduced by standard techniques, such as site-directed mutagenesis and PCR-mediated mutagenesis. Preferably, conservative amino acid substitutions are made at one or more non-essential amino acid residues.

As is well known, RNA may be isolated from the original cells or from transformed cells by standard techniques, such as guanidinium isothiocyanate extraction and precipitation followed by centrifugation or chromatography. Where desirable, mRNA may be isolated from total RNA by standard techniques such as chromatography on oligo dT cellulose. Suitable techniques are familiar in the art. In one embodiment, cDNAs that encode the light and the heavy chains of the antibody may be made, either simultaneously or separately, using reverse transcriptase and DNA polymerase in accordance with well-known methods. PCR may be initiated by consensus constant region primers or by more specific primers based on the published heavy and light chain DNA and amino acid sequences. As discussed above, PCR also may be used to isolate DNA clones encoding surface proteins or antibody light and heavy chains. In this case the libraries may be screened by consensus primers or larger homologous probes, such as porcine constant region probes.

DNA, typically plasmid DNA, may be isolated from the cells using techniques known in the art, restriction mapped and sequenced in accordance with standard, well known techniques set forth in detail, e.g., in the foregoing references relating to recombinant DNA techniques. Of course, the DNA may be synthetic according to the present invention at any point during the isolation process or subsequent analysis.

In one embodiment, the present invention provides an isolated polynucleotide comprising, consisting essentially of, or consisting of a nucleic acid encoding one or more Mycoplasma surface proteins. In another embodiment, the isolated polynucleotide encodes a recombinant chimeric surface protein polyprotein. In a further embodiment, the polyprotein encodes for one or more Vlp family members.

In one embodiment, the present invention provides an isolated polynucleotide comprising, consisting essentially of, or consisting of a nucleic acid encoding an immunoglobulin heavy chain variable region ($V_H$), where at least one of the CDRs of the heavy chain variable region or at least two of the $V_H$-CDRs of the heavy chain variable region are at least 80%, 85%, 90% or 95% identical to reference heavy chain $V_H$-CDR1, $V_H$-CDR2, or $V_H$-CDR3 amino acid sequences from the antibodies disclosed herein. Alternatively, the $V_H$-CDR1, $V_H$-CDR2, or $V_H$-CDR3 regions of the $V_H$ are at least 80%, 85%, 90% or 95% identical to reference heavy chain $V_H$-CDR1, $V_H$-CDR2, and $V_H$-CDR3 amino acid sequences from the antibodies disclosed herein. Thus, according to this embodiment a heavy chain variable region of the invention has $V_H$-CDR1, $V_H$-CDR2, or $V_H$-CDR3 polypeptide sequences related to the polypeptide sequences of the antibodies illustrated in the Examples.

In another embodiment, the present invention provides an isolated polynucleotide comprising, consisting essentially of, or consisting of a nucleic acid encoding an immunoglobulin light chain variable region ($V_L$), where at least one of the $V_L$-CDRs of the light chain variable region or at least two of the $V_L$-CDRs of the light chain variable region are at least 80%, 85%, 90% or 95% identical to reference light chain $V_L$-CDR1, $V_L$-CDR2, or $V_L$-CDR3 amino acid sequences from the antibodies disclosed herein. Alternatively, the $V_L$-CDR1, $V_L$-CDR2, or $V_L$-CDR3 regions of the $V_L$ are at least 80%, 85%, 90% or 95% identical to reference light chain $V_L$-CDR1, $V_L$-CDR2, and $V_L$-CDR3 amino acid sequences from the antibodies disclosed herein. Thus, according to this embodiment a light chain variable region of the invention has $V_L$-CDR1, $V_L$-CDR2, or $V_L$-CDR3 polypeptide sequences related to the polypeptide sequences of the antibodies illustrated in the Examples.

The present invention also includes fragments of the polynucleotides of the invention, as described elsewhere. Additionally, polynucleotides which encode fusion polynucleotides, Fab fragments, scFvs fragments, and other derivatives, as described herein, are also contemplated by the invention.

The polynucleotides may be produced or manufactured by any method known in the art. For example, if the nucleotide sequence of the antibody is known, a polynucleotide encoding the recombinant polyprotein or antibody may be assembled from chemically synthesized oligonucleotides, e.g., as described in Kutmeier et al., BioTechniques 17 (1994), 242, which, briefly, involves the synthesis of overlapping oligonucleotides containing portions of the sequence encoding the antibody, annealing and ligating of those oligonucleotides, and then amplification of the ligated oligonucleotides by PCR.

Alternatively, a polynucleotide encoding a Mycoplasma surface protein, an antibody, or antigen-binding fragment, variant, or derivative thereof may be generated from nucleic acid from a suitable source. If a clone containing a nucleic acid encoding a particular surface protein or antibody is not available, but the sequence of the antibody molecule is known, a nucleic acid encoding the antibody may be chemically synthesized or obtained from a suitable source (e.g., an antibody cDNA library, or a cDNA library generated from, or nucleic acid, preferably polyA$^+$ RNA, isolated from a sample of Mycoplasma) by PCR amplification using synthetic primers hybridizable to the 3' and 5' ends of the sequence or by cloning using an oligonucleotide probe specific for the particular gene sequence to identify, e.g., a cDNA clone from a cDNA library that encodes the antibody. Amplified nucleic acids generated by PCR may then be cloned into replicable cloning vectors using any method well known in the art.

Once the nucleotide sequence and corresponding amino acid sequence of the antibody, or antigen-binding fragment, variant, or derivative thereof is determined, its nucleotide sequence may be manipulated using methods well known in the art for the manipulation of nucleotide sequences, e.g., recombinant DNA techniques, site directed mutagenesis, PCR, etc. (see, for example, the techniques described in Sambrook et al., Molecular Cloning, A Laboratory Manual, 2d Ed., Cold Spring Harbor Laboratory, Cold Spring Harbor, N.Y. (1990) and Ausubel et al., eds., Current Protocols in Molecular Biology, John Wiley & Sons, N.Y. (1998), which are both incorporated by reference herein in their entireties), to generate antibodies having a different amino acid sequence, for example to create amino acid substitutions, deletions, and/or insertions.

Further Genetic Manipulations

The polynucleotide and amino acid sequence information provided by the present invention also makes possible the systematic analysis of the structure and function of the Mycoplasma genes and their encoded gene products. Knowledge of a polynucleotide encoding a gene product of the invention also makes available anti-sense polynucleotides which recognize and hybridize to polynucleotides encoding a polypeptide of the invention, or a fragment thereof. Full length and fragment anti-sense polynucleotides are useful in this respect. The worker of ordinary skill will appreciate that fragment anti-sense molecules of the invention include (i) those which specifically recognize and hybridize to a specific RNA (as determined by sequence comparison of DNA encoding a viral polypeptide of the invention as well as (ii) those which recognize and hybridize to RNA encoding variants of the encoded proteins. Anti-sense polynucleotides that hybridize to RNA/DNA encoding other Mycoplasma peptides are also identifiable through sequence comparison to identify characteristic, or signature sequences for the family of molecules, further of use in the study of antigenic domains in Mycoplasma polypeptides and may also be used to distinguish between infection of a host animal with remotely related Mycoplasma members.

Guidance for effective codon optimization for enhanced expression in yeast and E. coli for the constructs of the invention is generally known to those of skill in the art.

Expression of Polypeptides

Following manipulation of the isolated genetic material to provide surface proteins, recombinant chimeric polypeptide, antibodies, or antigen-binding fragments, variants, or derivatives thereof of the invention, the polynucleotides encoding the antibodies are typically inserted in an expression vector for introduction into host cells that may be used to produce the desired quantity of polypeptide. Recombinant expression of surface proteins, recombinant chimeric polypeptides, an antibody, or fragment, derivative or analog thereof, e.g., a heavy or light chain of an antibody which binds to a target molecule is described herein. Once a polynucleotide encoding a desired molecule of the invention has been obtained, the vector for the production of the antibody molecule may be produced by recombinant DNA technology using techniques well known in the art. Thus, methods for preparing a protein by expressing a polynucleotide containing an antibody encoding nucleotide sequence are described herein. Methods which are well known to those skilled in the art can be used to construct expression vectors containing antibody coding sequences and appropriate transcriptional and translational control signals. These methods include, for example, in vitro recombinant DNA techniques, synthetic techniques, and in vivo genetic recombination. The invention, thus, provides replicable vectors comprising a nucleotide sequence encoding an antibody molecule of the invention, or a heavy or light chain thereof, or a heavy or light chain variable domain, operably linked to a promoter. Such vectors may include the nucleotide sequence encoding the constant region of the antibody molecule (see, e.g., international applications WO 86/05807 and WO 89/01036; and U.S. Pat. No. 5,122,464) and the variable domain of the antibody may be cloned into such a vector for expression of the entire heavy or light chain.

The term "vector" or "expression vector" is used herein to mean vectors used in accordance with the present invention as a vehicle for introducing into and expressing a desired gene in a host cell. As known to those skilled in the art, such vectors may easily be selected from the group consisting of plasmids, phages, viruses and retroviruses. In general, vectors compatible with the instant invention will comprise a selection marker, appropriate restriction sites to facilitate cloning of the desired gene and the ability to enter and/or replicate in eukaryotic or prokaryotic cells. For the purposes of this invention, numerous expression vector systems may be employed. For example, one class of vector utilizes DNA elements which are derived from animal viruses such as bovine papilloma virus, polyoma virus, adenovirus, vaccinia virus, baculovirus, retroviruses (RSV, MMTV or MOMLV) or SV40 virus. Others involve the use of polycistronic systems with internal ribosome binding sites. Additionally, cells which have integrated the DNA into their chromosomes may be selected by introducing one or more markers which allow selection of transfected host cells. The marker may provide for prototrophy to an auxotrophic host, biocide resistance (e.g., antibiotics) or resistance to heavy metals such as copper. The selectable marker gene can either be directly linked to the DNA sequences to be expressed or introduced into the same cell by co-transformation. Additional elements may also be needed for optimal synthesis of mRNA. These elements may include signal sequences, splice signals, as well as transcriptional promoters, enhancers, and termination signals.

In some embodiments the cloned antibody variable region genes are inserted into an expression vector along with the heavy and light chain constant region genes as discussed above. In one embodiment, this is affected using a proprietary expression vector of Biogen IDEC, Inc., referred to as NEOSPLA, disclosed in U.S. Pat. No. 6,159,730. This vector contains the cytomegalovirus promoter/enhancer, the mouse beta globin major promoter, the SV40 origin of replication, the bovine growth hormone polyadenylation sequence, neomycin phosphotransferase exon 1 and exon 2, the dihydrofolate reductase gene and leader sequence. This vector has been found to result in very high-level expression of antibodies upon incorporation of variable and constant region genes, transfection in CHO cells, followed by selection in G418 containing medium and methotrexate amplification.

In other embodiments, any expression vector which is capable of eliciting expression in eukaryotic cells may be used in the present invention. Examples of suitable vectors include, but are not limited to plasmids pcDNA3, pHCMV/Zeo, pCR3.1, pEF1/His, pIND/GS, pRc/HCMV2, pSV40/Zeo2, pTRACER-HCMV, pUB6/V5-His, pVAX1, and pZeoSV2 (available from Invitrogen, San Diego, Calif.), plasmid pCI (available from Promega, Madison, Wis.). In general, screening large numbers of transformed cells for those which express suitably high levels if immunoglobulin heavy and light chains is routine experimentation which can be carried out, for example, by robotic systems. Vector systems are also taught in U.S. Pat. Nos. 5,736,137 and 5,658,570, each of which is incorporated by reference in its entirety herein. This system provides for high expression levels, e.g., >30 pg/cell/day. Other exemplary vector systems are disclosed e.g., in U.S. Pat. No. 6,413,777.

In other embodiments the polypeptides of the invention may be expressed using polycistronic constructs such as those disclosed in US patent application publication no. 2003-0157641 A1 and incorporated herein in its entirety. In these expression systems, multiple gene products of interest such as Vlp family members or heavy and light chains of antibodies may be produced from a single polycistronic construct. These systems advantageously use an internal ribosome entry site (IRES) to provide relatively high levels of antibodies. Compatible IRES sequences are disclosed in U.S. Pat. No. 6,193,980 which is also incorporated herein. Those skilled in the art will appreciate that such expression systems may be used to effectively produce the full range of antibodies disclosed in the instant application.

More generally, once the vector or DNA sequence encoding a nucleotide has been prepared, the expression vector may be introduced into an appropriate host cell. Introduction of the plasmid into the host cell can be accomplished by various techniques well known to those of skill in the art. These include, but are not limited to, transfection including lipotransfection using, e.g., Fugene or lipofectamine, protoplast fusion, calcium phosphate precipitation, cell fusion with enveloped DNA, microinjection, and infection with intact virus. Typically, plasmid introduction into the host is via standard calcium phosphate co-precipitation method. The host cells harboring the expression construct are grown under conditions appropriate to the production of the light chains and heavy chains and assayed for heavy and/or light chain protein synthesis. Exemplary assay techniques include enzyme-linked immunosorbent assay (ELISA), radioimmunoassay (MA), enzyme immuno assay (EIA) or fluorescence-activated cell sorter analysis (FACS), microbead-based immunoassay, proximity assay (e.g., AlphaLISA), immunohistochemistry and the like.

The expression vector is transferred to a host cell by conventional techniques and the transfected cells are then cultured by conventional techniques to produce a polypeptide for use in the methods described herein. Thus, the invention includes host cells containing a polynucleotide encoding a polypeptide of the invention operably linked to a heterologous promoter.

As used herein, "host cells" refers to cells which harbor vectors constructed using recombinant DNA techniques and encoding at least one heterologous gene. In descriptions of processes for isolation of polypeptides from recombinant hosts, the terms "cell" and "cell culture" are used interchangeably to denote the source of polypeptide unless it is clearly specified otherwise. In other words, recovery of polypeptide from the "cells" may mean either from spun down whole cells, or from the cell culture containing both the medium and the suspended cells.

A variety of host-expression vector systems may be utilized to express polypeptides for use in the methods described herein. Such host-expression systems represent vehicles by which the coding sequences of interest may be produced and subsequently purified, but also represent cells which may, when transformed or transfected with the appropriate nucleotide coding sequences, express an antibody molecule of the invention in situ. These include but are not limited to microorganisms such as bacteria (e.g., *E. coli, B. subtilis*) transformed with recombinant bacteriophage DNA, plasmid DNA or cosmid DNA expression vectors containing antibody coding sequences; yeast (e.g., Saccharomyces, Pichia) transformed with recombinant yeast expression vectors containing antibody coding sequences; insect cell systems infected with recombinant virus expression vectors (e.g., baculovirus) containing antibody coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing antibody coding sequences; or mammalian cell systems (e.g., COS, CHO, NSO, BLK, 293, 3T3 cells) harboring recombinant expression constructs containing promoters derived from the genome of mammalian cells (e.g., metallothionein promoter) or from mammalian viruses (e.g., the adenovirus late promoter; the vaccinia virus 7.5K promoter). Preferably, bacterial cells such as *Escherichia coli*, and more preferably, eukaryotic cells, especially for the expression of whole recombinant antibody molecule, are used for the expression of a recombinant antibody molecule. For example, mammalian cells such as Chinese Hamster Ovary (CHO) cells, in conjunction with a vector such as the major intermediate early gene promoter element from human cytomegalovirus is an effective expression system for antibodies; see, e.g., Foecking et al., Gene 45 (1986), 101; Cockett et al., Bio/Technology 8 (1990), 2.

The host cell line used for protein expression may be of mammalian origin; those skilled in the art are credited with ability to preferentially determine particular host cell lines which are best suited for the desired gene product to be expressed therein. Exemplary host cell lines include, but are not limited to, CHO (Chinese Hamster Ovary), DG44 and DUXB11 (Chinese Hamster Ovary lines, DHFR minus), HELA (human cervical carcinoma), CVI (monkey kidney line), COS (a derivative of CVI with SV40 T antigen), VERY, BHK (baby hamster kidney), MDCK, WI38, R1610 (Chinese hamster fibroblast) BALBC/3T3 (mouse fibroblast), HAK (hamster kidney line), SP2/O (mouse myeloma), P3x63-Ag3.653 (mouse myeloma), BFA-1c1BPT (bovine endothelial cells), RAJI (human lymphocyte) and 293 (human kidney). CHO and 293 cells are particularly preferred. Host cell lines are typically available from commercial services, the American Tissue Culture Collection or from published literature.

In addition, a host cell strain may be chosen which modulates the expression of the inserted sequences or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used.

For long-term, high-yield production of recombinant proteins, stable expression is preferred. For example, cell lines which stably express the antibody molecule may be engineered. Rather than using expression vectors which contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells may be allowed to grow for 1-2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which stably express the antibody molecule.

A number of selection systems may be used, including but not limited to the herpes simplex virus thymidine kinase (Wigler et al., Cell 11 (1977), 223), hypoxanthine-guanine phosphoribosyltransferase (Szybalska & Szybalski, Proc. Natl. Acad. Sci. USA 48 (1992), 202), and adenine phosphoribosyltransferase (Lowy et al., Cell 22 (1980), 817) genes can be employed in tk-, hgprt- or aprt-cells, respectively. Also, anti-metabolite resistance can be used as the basis of selection for the following genes: dhfr, which confers resistance to methotrexate (Wigler et al., Natl. Acad. Sci. USA 77 (1980), 357; O'Hare et al., Proc. Natl. Acad. Sci. USA 78 (1981), 1527); gpt, which confers resistance to mycophenolic acid (Mulligan & Berg, Proc. Natl. Acad. Sci. USA 78 (1981), 2072); neo, which confers resistance to the aminoglycoside G-418 Goldspiel et al., Clinical Pharmacy 12 (1993), 488-505; Wu and Wu, Biotherapy 3 (1991), 87-95; Tolstoshev, Ann. Rev. Pharmacol. Toxicol. 32 (1993), 573-596; Mulligan, Science 260 (1993), 926-932; and Morgan and Anderson, Ann. Rev. Biochem. 62 (1993), 191-217; TIB TECH 11 (1993), 155-215; and hygro, which confers resistance to hygromycin (Santerre et al., Gene 30 (1984), 147. Methods commonly known in the art of recombinant DNA technology which can be used are described in Ausubel et al. (eds.), Current Protocols in Molecular Biology, John Wiley & Sons, NY (1993); Kriegler, Gene Transfer and Expression, A Laboratory Manual, Stockton Press, NY (1990); and in Chapters 12 and 13, Dracopoli et al. (eds), Current Protocols in Human Genetics, John Wiley & Sons, NY (1994); Colberre-Garapin et al., J. Mol. Biol. 150:1 (1981), which are incorporated by reference herein in their entireties.

The expression levels of a polypeptide can be increased by vector amplification, for a review, see Bebbington and Hentschel. The use of vectors based on gene amplification for the expression of cloned genes in mammalian cells in DNA cloning, Academic Press, New York, Vol. 3. (1987). When a marker in the vector system expressing polypeptide is amplifiable, increase in the level of inhibitor present in culture of host cell will increase the number of copies of the marker gene. Since the amplified region is associated with the polypeptide gene, production of the polypeptide will also increase; see Crouse et al., Mol. Cell. Biol. 3 (1983), 257.

In vitro production allows scale-up to give large amounts of the desired polypeptides. Techniques for mammalian cell cultivation under tissue culture conditions are known in the art and include homogeneous suspension culture, e.g. in an airlift reactor or in a continuous stirrer reactor, or immobilized or entrapped cell culture, e.g. in hollow fibers, microcapsules, on agarose microbeads or ceramic cartridges. If necessary and/or desired, the solutions of polypeptides can be purified by the customary chromatography methods, for example gel filtration, ion-exchange chromatography, chromatography over DEAE-cellulose or (immuno-)affinity chromatography, e.g., after preferential biosynthesis of a synthetic hinge region polypeptide or prior to or subsequent to the HIC chromatography step described herein.

Genes encoding surface proteins, recombinant chimeric polypeptides, antibodies, or antigen-binding fragments, variants, or derivatives thereof of the invention can also be expressed in non-mammalian cells such as bacteria or insect or yeast or plant cells. Bacteria which readily take up nucleic acids include members of the enterobacteriaceae, such as strains of *Escherichia coli* or *Salmonella; Bacillaceae*, such as *Bacillus subtilis; Pneumococcus; Streptococcus*, and *Haemophilus influenzae*. It will further be appreciated that, when expressed in bacteria, the heterologous polypeptides typically become part of inclusion bodies. The heterologous polypeptides must be isolated, purified and then assembled into functional molecules. Where tetravalent forms of antibodies are desired, the subunits will then self-assemble into tetravalent antibodies; see, e.g., international application WO02/096948.

In bacterial systems, a number of expression vectors may be advantageously selected depending upon the use intended for the antibody molecule being expressed. For example, when a large quantity of such a protein is to be produced, for the generation of pharmaceutical compositions of an antibody molecule, vectors which direct the expression of high levels of fusion protein products that are readily purified may be desirable. Such vectors include, but are not limited, to the *E. coli* expression vector pUR278 (Ruther et al., EMBO J. 2 (1983), 1791), in which the antibody coding sequence may be ligated individually into the vector in frame with the lacZ coding region so that a fusion protein is produced; pIN vectors (Inouye & Inouye, Nucleic Acids Res. 13 (1985), 3101-3109; Van Heeke & Schuster, J. Biol. Chem. 24 (1989), 5503-5509); and the like. pGEX vectors may also be used to express foreign polypeptides as fusion proteins with glutathione S-transferase (GST). In general, such fusion proteins are soluble and can easily be purified from lysed cells by adsorption and binding to a matrix of glutathione-agarose beads followed by elution in the presence of free glutathione. The pGEX vectors are designed to include thrombin or factor Xa protease cleavage sites so that the cloned target gene product can be released from the GST moiety.

In addition to prokaryotes, eukaryotic microbes may also be used. *Saccharomyces cerevisiae*, or common baker's yeast, is the most commonly used among eukaryotic microorganisms although a number of other strains are commonly available, e.g., Pichia pastoris. For expression in Saccharomyces, the plasmid YRp7, for example, (Stinchcomb et al., Nature 282 (1979), 39; Kingsman et al., Gene 7 (1979), 141; Tschemper et al., Gene 10 (1980), 157) is commonly used. This plasmid already contains the TRP1 gene which provides a selection marker for a mutant strain of yeast lacking the ability to grow in tryptophan, for example ATCC No. 44076 or PEP4-1 (Jones, Genetics 85 (1977), 12). The presence of the trp1 lesion as a characteristic of the yeast host cell genome then provides an effective environment for detecting transformation by growth in the absence of tryptophan.

In an insect system, *Autographa californica* nuclear polyhedrosis virus (AcNPV) is typically used as a vector to express foreign genes. The virus grows in *Spodoptera frupperda* cells. The antibody coding sequence may be cloned individually into non-essential regions (for example the polyhedrin gene) of the virus and placed under control of an AcNPV promoter (for example the polyhedrin promoter).

Once an antibody molecule of the invention has been recombinantly expressed, the whole antibodies, their dimers, individual light and heavy chains, or other immunoglobulin forms of the present invention, can be purified according to standard procedures of the art, including for example, by chromatography (e.g., ion exchange, affinity, particularly by affinity for the specific antigen after Protein A, and sizing column chromatography), centrifugation, differential solubility, e.g. ammonium sulfate precipitation, or by any other standard technique for the purification of proteins; see, e.g., Scopes, "Protein Purification", Springer Verlag, N.Y. (1982). Alternatively, a preferred method for increasing the affinity of antibodies of the invention is disclosed in US patent publication 2002-0123057 A1.

Fusion Proteins and Conjugates

In certain embodiments, the chimeric polypeptide or antibody polypeptide comprises an amino acid sequence or one or more moieties not normally associated with a single surface protein or antibody. Exemplary modifications are described in more detail below. For example, a single-chain Fv antibody fragment of the invention may comprise a flexible linker sequence, or may be modified to add a functional moiety (e.g., PEG, a drug, a toxin, or a label such as a fluorescent, radioactive, enzyme, nuclear magnetic, heavy metal and the like)

An antibody polypeptide of the invention may comprise, consist essentially of, or consist of a fusion protein. Fusion proteins are chimeric molecules which comprise, for example, an immunoglobulin Mycoplasma surface protein-binding domain with at least one target binding site, and at least one heterologous portion, i.e., a portion with which it is not naturally linked in nature. The amino acid sequences may normally exist in separate proteins that are brought together in the fusion polypeptide or they may normally exist in the same protein but are placed in a new arrangement in the fusion polypeptide. Fusion proteins may be created, for example, by chemical synthesis, or by creating and translating a polynucleotide in which the peptide regions are encoded in the desired relationship.

The term "heterologous" as applied to a polynucleotide or a polypeptide, means that the polynucleotide or polypeptide is derived from a distinct entity from that of the rest of the entity to which it is being compared. For instance, as used herein, a "heterologous polypeptide" to be fused to surface protein or to an antibody, or an antigen-binding fragment, variant, or analog thereof is derived from a non-immunoglobulin polypeptide of the same species, or an immunoglobulin or non-immunoglobulin polypeptide of a different species. For example, a polypeptide comprising of surface proteins from multiple species of Mycoplasma.

As discussed in more detail elsewhere herein, surface proteins, antibodies, or antigen-binding fragments, variants, or derivatives thereof of the invention may further be recombinantly fused to a heterologous polypeptide at the N- or C-terminus or chemically conjugated (including covalent and non-covalent conjugations) to polypeptides or other compositions. For example, antibodies may be recombinantly fused or conjugated to molecules useful as labels in detection assays and effector molecules such as heterologous polypeptides, drugs, radionuclides, or toxins; see, e.g., international applications WO92/08495; WO91/14438; WO89/12624; U.S. Pat. No. 5,314,995; and European patent application EP 0 396 387.

Surface proteins, antibodies, or antigen-binding fragments, variants, or derivatives thereof of the invention can be composed of amino acids joined to each other by peptide bonds or modified peptide bonds, i.e., peptide isosteres, and may contain amino acids other than the 20 gene-encoded amino acids. Polypeptides may be modified by natural processes, such as posttranslational processing, or by chemical modification techniques which are well known in the art. Such modifications are well described in basic texts and in more detailed monographs, as well as in a voluminous research literature. Modifications can occur anywhere in the polypeptide, including the peptide backbone, the amino acid side-chains and the amino or carboxyl termini, or on moieties such as carbohydrates. It will be appreciated that the same type of modification may be present in the same or varying degrees at several sites in a given antibody. Also, a given antibody may contain many types of modifications. Polypeptides may be branched, for example, as a result of ubiquitination, and they may be cyclic, with or without branching. Cyclic, branched, and branched cyclic polypeptides may result from post-translation natural processes or may be made by synthetic methods. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristoylation, oxidation, pegylation, proteolytic processing, phosphorylation, prenylation, racemization, selenoylation, sulfation, transfer-RNA mediated addition of amino acids to proteins such as arginylation, and ubiquitination; see, e.g., Proteins—Structure And Molecular Properties, T. E. Creighton, W. H. Freeman and Company, New York 2nd Ed., (1993); Posttranslational Covalent Modification Of Proteins, B. C. Johnson, Ed., Academic Press, New York, pgs. 1-12 (1983); Seifter et al., Meth. Enzymol. 182 (1990), 626-646; Rattan et al., Ann. NY Acad. Sci. 663 (1992), 48-62).

The present invention also provides for fusion proteins comprising an antibody, or antigen-binding fragment, variant, or derivative thereof, and a heterologous polypeptide. In one embodiment, a fusion protein of the invention comprises, consists essentially of or consists of, a polypeptide having the amino acid sequence of any one or more of the $V_H$ regions of an antibody of the invention or the amino acid sequence of any one or more of the $V_L$ regions of an antibody of the invention or fragments or variants thereof, and a heterologous polypeptide sequence. In another embodiment, a fusion protein for use in the diagnostic and treatment methods disclosed herein comprises, consists essentially of, or consists of a polypeptide having the amino acid sequence of any one, two, three of the $V_H$-CDRs of an antibody, or fragments, variants, or derivatives thereof, or the amino acid sequence of any one, two, three of the $V_L$-CDRs of an antibody, or fragments, variants, or derivatives thereof, and a heterologous polypeptide sequence. In one embodiment, the fusion protein comprises a polypeptide having the amino acid sequence of a $V_H$-CDR3 of an antibody of the present invention, or fragment, derivative, or variant thereof, and a heterologous polypeptide sequence, which fusion protein specifically binds to Mycoplasma surface protein. In another embodiment, a fusion protein comprises a polypeptide having the amino acid sequence of at least one $V_H$ region of an antibody of the invention and the amino acid sequence of at least one $V_L$ region of an antibody of the invention or fragments, derivatives or variants thereof, and a heterologous polypeptide sequence. Preferably, the $V_H$ and $V_L$ regions of the fusion protein correspond to a single source antibody (or scFv or Fab fragment) which specifically binds Mycoplasma surface protein. In yet another embodiment, a fusion protein for use in the diagnostic and treatment methods disclosed herein comprises a polypeptide having the amino acid sequence of any one, two, three or more of the $V_H$ CDRs of an antibody and the amino acid sequence of any one, two, three or more of the $V_L$ CDRs of an antibody, or fragments or variants thereof, and a heterologous polypeptide sequence. Preferably, two, three, four, five, six, or more of the $V_H$-CDR(s) or $V_L$-CDR(s) correspond to single source antibody (or scFv or Fab fragment) of the invention. Nucleic acid molecules encoding these fusion proteins are also encompassed by the invention.

Exemplary fusion proteins reported in the literature include fusions of the T cell receptor (Gascoigne et al., Proc. Natl. Acad. Sci. USA 84 (1987), 2936-2940; CD4 (Capon et al., Nature 337 (1989), 525-531; Traunecker et al., Nature 339 (1989), 68-70; Zettmeissl et al., DNA Cell Biol. USA 9 (1990), 347-353; and Byrn et al., Nature 344 (1990), 667-670); L-selectin (homing receptor) (Watson et al., J. Cell. Biol. 110 (1990), 2221-2229; and Watson et al., Nature 349 (1991), 164-167); CD44 (Aruffo et al., Cell 61 (1990), 1303-1313); CD28 and B7 (Linsley et al., J. Exp. Med. 173 (1991), 721-730); CTLA-4 (Lisley et al., J. Exp. Med. 174 (1991), 561-569); CD22 (Stamenkovic et al., Cell 66 (1991), 1133-1144); TNF receptor (Ashkenazi et al., Proc. Natl. Acad. Sci. USA 88 (1991), 10535-10539; Lesslauer et al., Eur. J. Immunol. 27 (1991), 2883-2886; and Peppel et al., J. Exp. Med. 174 (1991), 1483-1489 (1991); and IgE receptor a (Ridgway and Gorman, J. Cell. Biol. 115 (1991), Abstract No. 1448).

As discussed elsewhere herein, surface proteins, chimeric polypeptides, antibodies, or antigen-binding fragments, variants, or derivatives thereof of the invention may be fused to heterologous polypeptides to increase the in vivo half-life of the polypeptides or for use in immunoassays using methods known in the art. For example, in one embodiment, PEG can be conjugated to the antibodies of the invention to increase their half-life in vivo; see, e.g., Leong et al., Cytokine 16 (2001), 106-119; Adv. in Drug Deliv. Rev. 54 (2002), 531; or Weir et al., Biochem. Soc. Transactions 30 (2002), 512.

Moreover, surface proteins, chimeric polypeptides, antibodies, or antigen-binding fragments, variants, or derivatives thereof of the invention can be fused to marker sequences, such as a peptide to facilitate their purification or detection. In preferred embodiments, the marker amino acid sequence is a hexa-histidine peptide (HIS), such as the tag provided in a pQE vector (QIAGEN, Inc., 9259 Eton Avenue, Chatsworth, Calif., 91311), among others, many of which are commercially available. As described in Gentz et al., Proc. Natl. Acad. Sci. USA 86 (1989), 821-824, for instance, hexa-histidine provides for convenient purification of the fusion protein. Other peptide tags useful for purification include, but are not limited to, the "HA" tag, which corresponds to an epitope derived from the influenza hemagglutinin protein (Wilson et al., Cell 37 (1984), 767) and the "flag" tag.

Fusion proteins can be prepared using methods that are well known in the art; see for example U.S. Pat. Nos. 5,116,964 and 5,225,538. The precise site at which the fusion is made may be selected empirically to optimize the secretion or binding characteristics of the fusion protein. DNA encoding the fusion protein is then transfected into a host cell for expression.

Antibodies of the present invention may be used in non-conjugated form or may be conjugated to at least one of a variety of molecules, e.g., to improve the therapeutic properties of the molecule, to facilitate target detection, or for imaging or therapy of the patient. Antibodies, or antigen-binding fragments, variants, or derivatives thereof of the invention can be labeled or conjugated either before or after purification, when purification is performed. In particular, antibodies, or antigen-binding fragments, variants, or derivatives thereof of the invention may be conjugated to therapeutic agents, prodrugs, peptides, proteins, enzymes, viruses, lipids, biological response modifiers, pharmaceutical agents, or PEG.

Conjugates that are immunotoxins including conventional antibodies have been widely described in the art. The toxins may be coupled to the antibodies by conventional coupling techniques or immunotoxins containing protein toxin portions can be produced as fusion proteins. The antibodies of the present invention can be used in a corresponding way to obtain such immunotoxins. Illustrative of such immunotoxins are those described by Byers, Seminars Cell. Biol. 2 (1991), 59-70 and by Fanger, Immunol. Today 12 (1991), 51-54. Those skilled in the art will appreciate that conjugates may also be assembled using a variety of techniques depending on the selected agent to be conjugated. For example, conjugates with biotin are prepared e.g. by reacting a surface protein binding polypeptide with an activated ester of biotin such as the biotin N-hydroxysuccinimide ester. Similarly, conjugates with a fluorescent marker may be prepared in the presence of a coupling agent, e.g. those listed herein, or by reaction with an isothiocyanate, preferably fluorescein-isothiocyanate. Conjugates of the antibodies, or antigen-binding fragments, variants, or derivatives thereof of the invention are prepared in an analogous manner.

The present invention further encompasses surface proteins, chimeric polypeptides, antibodies, or antigen-binding fragments, variants, or derivatives thereof of the invention conjugated to a diagnostic or therapeutic agent. The antibodies can be used diagnostically to, for example, demonstrate presence of a Mycoplasma disease. Detection can be facilitated by coupling the antibody, or antigen-binding fragment, variant, or derivative thereof to a detectable substance. Examples of detectable substances include various enzymes, prosthetic groups, fluorescent materials, luminescent materials, bioluminescent materials, radioactive materials, positron emitting metals using various positron emission tomographies, and nonradioactive paramagnetic metal ions; see, e.g., U.S. Pat. No. 4,741,900 for metal ions which can be conjugated to antibodies for use as diagnostics according to the present invention. Examples of suitable enzymes include horseradish peroxidase, alkaline phosphatase, beta.-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin; and examples of suitable radioactive material include. $^{125}$I, $^{131}$I, $^{111}$In or $^{99}$Tc.

A polypeptide of the invention also can be detectably labeled by coupling it to a chemiluminescent compound. The presence of the chemiluminescent-tagged polypeptide is then determined by detecting the presence of luminescence that arises during the course of a chemical reaction. Examples of particularly useful chemiluminescent labeling compounds are luminol, isoluminol, theromatic acridinium ester, imidazole, acridinium salt and oxalate ester.

One of the ways in which a polypeptide of the invention can be detectably labeled is by linking the same to an enzyme and using the linked product in an enzyme immuno assay (EIA) (Voller, A., "The Enzyme Linked Immunosorbent Assay (ELISA)" Microbiological Associates Quarterly Publication, Walkersville, Md., Diagnostic Horizons 2 (1978), 1-7); Voller et al., J. Clin. Pathol. 31 (1978), 507-520; Butler, Meth. Enzymol. 73 (1981), 482-523; Maggio, E. (ed.), Enzyme Immunoassay, CRC Press, Boca Raton, Fla., (1980); Ishikawa, E. et al., (eds.), Enzyme Immunoassay, Kgaku Shoin, Tokyo (1981). The enzyme, which is bound to the antibody will react with an appropriate substrate, preferably a chromogenic substrate, in such a manner as to produce a chemical moiety which can be detected, for example, by spectrophotometric, fluorometric or by visual means. Enzymes which can be used to detectably label the antibody include, but are not limited to, malate dehydrogenase, staphylococcal nuclease, delta-5-steroid isomerase, yeast alcohol dehydrogenase, alpha-glycerophosphate, dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase and acetylcholinesterase. Additionally, the detection can be accomplished by colorimetric methods which employ a chromogenic substrate for the enzyme. Detection may also be accomplished by visual comparison of the extent of enzymatic reaction of a substrate in comparison with similarly prepared standards.

Detection may also be accomplished using any of a variety of other immunoassays. For example, by radioactively labeling the antibody, or antigen-binding fragment, variant, or derivative thereof, it is possible to detect the antibody through the use of a radioimmunoassay (MA) (see, for example, Weintraub, B., Principles of Radioimmunoassays, Seventh Training Course on Radioligand Assay Techniques, The Endocrine Society, (March, 1986)), which is incorporated by reference herein). The radioactive isotope can be detected by means including, but not limited to, a gamma counter, a scintillation counter, or autoradiography.

A polypeptide of the invention can also be detectably labeled using fluorescence emitting metals such as $^{152}$Eu, or others of the lanthanide series. These metals can be attached to the antibody using such metal chelating groups as diethylenetriaminepentacetic acid (DTPA) or ethylenediaminetetraacetic acid (EDTA).

Techniques for conjugating various moieties to polypeptides are well known, see, e.g., Arnon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. (1985); Hellstrom et al., "Antibodies For Drug Delivery", in Controlled Drug Delivery (2nd Ed.), Robinson et al. (eds.), Marcel Dekker, Inc., pp. 623-53 (1987); Thorpe, "Antibody Carriers Of Cytotoxic Agents In Cancer Therapy: A Review", in Monoclonal Antibodies '84: Biological And Clinical Applications, Pinchera et al. (eds.), pp. 475-506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), Academic Press pp. 303-16 (1985), and Thorpe et al., "The Preparation And Cytotoxic Properties Of Antibody-Toxin Conjugates", Immunol. Rev. 62 (1982), 119-158.

As mentioned, in certain embodiments, a moiety that enhances the stability or efficacy of a binding molecule, e.g., a binding polypeptide, e.g., an antibody or immunospecific fragment thereof can be conjugated. For example, in one embodiment, PEG can be conjugated to the binding molecules of the invention to increase their half-life in vivo. Leong et al., Cytokine 16 (2001), 106; Adv. in Drug Deliv. Rev. 54 (2002), 531; or Weir et al., Biochem. Soc. Transactions 30 (2002), 512.

Antibodies

The present invention also relates to anti Mycoplasma surface protein antibodies and antigen-binding fragments thereof, which preferably demonstrate the immunological binding characteristics and/or biological properties as outlined for the antibodies illustrated in the Examples.

In one embodiment, the present invention is directed to an anti-MHR chimeric VlpA-G polyprotein antibody, or antigen-binding fragment, variant or derivatives thereof, where the antibody specifically binds to the same epitope of Mycoplasma surface protein as natural antibodies. Selection can be done using any method known in the art, such as, but not limited to, column purification. For the monoclonal antibodies, hybridomas may be created. The hybridomas may then assayed for specific binding to MEM chimeric VlpA-G polyprotein and not having cross-binding to other surface proteins of MHR or other Mycoplasma species.

The present invention further exemplifies several such binding molecules, e.g. antibodies and binding fragments thereof which may be characterized by comprising in their variable region, e.g. binding domain at least one complementarity determining region (CDR) of the $V_H$ and/or $V_L$ variable region able to bind Mycoplasma surface proteins or a chimeric polypeptide of surface proteins.

Alternatively, the antibody of the present invention is an antibody or antigen-binding fragment, derivative or variant thereof, which competes for binding to Mycoplasma surface proteins or a chimeric polypeptide of surface proteins. Those antibodies may be porcinized murine or porcine-murine chimeric antibodies, in particular for therapeutic applications. Alternatively, the antibody is a murine, murinized and chimeric murine-human antibody, which are particularly useful for diagnostic methods and studies in animals.

As mentioned above, due to its specificity the polyclonal and monoclonal antibodies of the present invention will recognize epitopes which are of particular physiological relevance and show a specificity not found in commercially available antibodies. Accordingly, it is prudent to stipulate that the epitope of the human anti-Mycoplasma surface protein or chimeric polypeptide antibody of the present invention is unique and no other antibody which is capable of binding to the epitope recognized by the polyclonal or monoclonal antibody of the present invention exists. Therefore, the present invention also extends generally to anti Mycoplasma surface protein or chimeric polypeptide antibodies and Mycoplasma surface protein or chimeric polypeptide binding molecules which compete with the polyclonal and monoclonal antibody of the present invention for specific binding to Mycoplasma surface protein or chimeric polypeptide.

Competition between antibodies may be determined, for examples, by an assay in which the immunoglobulin under test inhibits specific binding of a reference antibody to a common antigen, such as Mycoplasma surface protein or chimeric polypeptide. Numerous types of competitive binding assays are known, for example: solid phase direct or indirect radioimmunoassay (MA), solid phase direct or indirect enzyme immunoassay (ETA), sandwich competition assay, enzyme immuno assay (EIA); see Stahli et al., Methods in Enzymology 9 (1983), 242-253; solid phase direct biotin-avidin EIA; see Kirkland et al., J. Immunol. 137 (1986), 3614-3619 and Cheung et al., Virology 176 (1990), 546-552; solid phase direct labeled assay, solid phase direct labeled sandwich assay; see Harlow and Lane, Antibodies, A Laboratory Manual, Cold Spring Harbor Press (1988); solid phase direct label RIA using $^{1125}$ label; see Morel et al, Molec. Immunol. 25 (1988), 7-15 and Moldenhauer et al., Scand. J. Immunol. 32 (1990), 77-82. Typically, such an assay involves the use of purified Mycoplasma surface protein or chimeric polypeptide or aggregates thereof bound to a solid surface or cells bearing either of these, an unlabeled test immunoglobulin and a labeled reference immunoglobulin, i.e. the monoclonal antibody of the present invention. Competitive inhibition is measured by determining the amount of label bound to the solid surface or cells in the presence of the test immunoglobulin. Usually the test immunoglobulin is present in excess. Antibodies identified by competition assay (competing antibodies) include antibodies binding to the same epitope as the reference antibody and antibodies binding to an adjacent epitope sufficiently proximal to the epitope bound by the reference antibody for steric hindrance to occur. Usually, when a competing antibody is present in excess, it will inhibit specific binding of a reference antibody to a common antigen by at least 50% or 75%. Hence, the present invention is further drawn to an antibody, or antigen-binding fragment, variant or derivatives thereof, where the antibody competitively inhibits a reference antibody selected from the antibodies illustrated in the Examples from binding to Mycoplasma surface protein.

In another embodiment, the present invention provides an isolated polypeptide comprising, consisting essentially of or consisting of an immunoglobulin heavy chain variable region ($V_H$) or light chain variable region ($V_L$, together V), where at least one of V-CDRs of the heavy or light chain variable region or at least two of the V-CDRs of the heavy or light chain variable region are at least 80%, 85%, 90% or 95% identical to reference heavy or light chain V-CDR1, V-CDR2 or V-CDR3 amino acid sequences from the antibodies disclosed herein. Alternatively, the V-CDR1, V-CDR2 and V-CDR3 regions of the V are at least 80%, 85%, 90% or 95% identical to reference heavy chain V-CDR1, V-CDR2 and V-CDR3 amino acid sequences from the antibodies disclosed herein.

In another embodiment, the present invention provides an isolated polypeptide comprising, consisting essentially of, or consisting of an immunoglobulin variable region (V) of the light and/or heavy chain in which the V-CDR1, V-CDR2 and V-CDR3 regions have polypeptide sequences which are identical to the V-CDR1, V-CDR2 and V-CDR3 groups of the antibodies disclosed herein.

In another embodiment, the present invention provides an isolated polypeptide comprising, consisting essentially of, or consisting of an immunoglobulin variable region (V) of the heavy or light chain in which the V-CDR1, V-CDR2 and V-CDR3 regions have polypeptide sequences which are identical to the V-CDR1, V-CDR2 and V-CDR3 groups of the antibodies disclosed herein, except for one, two, three, four, five, or six amino acid substitutions in any one V-CDR. In certain embodiments the amino acid substitutions are conservative.

An immunoglobulin or its encoding cDNA may be further modified. Thus, in a further embodiment the method of the present invention comprises any one of the step(s) of producing, for example, a chimeric antibody, porcinized, murinized, or humanized antibody, single-chain antibody, Fab-fragment, bispecific antibody, fusion antibody, labeled antibody or an analog of any one of those. Corresponding methods are known to the person skilled in the art and are described, e.g., in Harlow and Lane "Antibodies, A Laboratory Manual", CSH Press, Cold Spring Harbor (1988). When derivatives of said antibodies are obtained by the phage display technique, surface plasmon resonance as employed in the BlAcore system can be used to increase the efficiency of phage antibodies which bind to the same epitope as that of any one of the antibodies described herein (Schier, Human Antibodies Hybridomas 7 (1996), 97-105; Malmborg, J. Immunol. Methods 183 (1995), 7-13). The production of chimeric antibodies is described, for example, in international application WO89/09622. Methods for the production of humanized antibodies are described in, e.g., European application EP-Al 0 239 400 and international application WO90/07861. A further source of antibodies to be utilized in accordance with the present invention are so-called xenogeneic antibodies. The general principle for the production of xenogeneic antibodies such as human-like antibodies in mice is described in, e.g., international applications WO91/10741, WO94/02602, WO96/34096 and WO 96/33735. As discussed above, the antibody of the invention may exist in a variety of forms besides complete antibodies; including, for example, Fv, Fab and F(ab)$_2$, as well as in single chains, for example scFv; see e.g. international application WO88/09344.

The antibodies of the present invention or their corresponding immunoglobulin chain(s) can be further modified using conventional techniques known in the art, for example, by using amino acid deletion(s), insertion(s), substitution(s), addition(s), and/or recombination(s) and/or any other modification(s) known in the art either alone or in combination. Methods for introducing such modifications in the DNA sequence underlying the amino acid sequence of an immunoglobulin chain are well known to the person skilled in the art; see, e.g., Sambrook, Molecular Cloning A Laboratory Manual, Cold Spring Harbor Laboratory (1989) N.Y. and Ausubel, Current Protocols in Molecular Biology, Green Publishing Associates and Wiley Interscience, N.Y. (1994). Modifications of the antibody of the invention include chemical and/or enzymatic derivatizations at one or more constituent amino acids, including side chain modifications, backbone modifications, and N- and C-terminal modifications including acetylation, hydroxylation, methylation, amidation, and the attachment of carbohydrate or lipid moieties, cofactors, and the like. Likewise, the present invention encompasses the production of chimeric proteins which comprise the described antibody or some fragment thereof at the amino terminus fused to heterologous molecule such as an immunostimulatory ligand at the carboxyl terminus; see, e.g., international application WO00/30680 for corresponding technical details.

Additionally, the present invention encompasses peptides including those containing a binding molecule as described above, for example containing the CDR3 region of the variable region of any one of the mentioned antibodies, in particular CDR3 of the heavy chain since it has frequently been observed that heavy chain CDR3 (HCDR3) is the region having a greater degree of variability and a predominant participation in antigen-antibody interaction. Such peptides may easily be synthesized or produced by recombinant means to produce a binding agent useful according to the invention. Such methods are well known to those of ordinary skill in the art. Peptides can be synthesized for example, using automated peptide synthesizers which are commercially available. The peptides can also be produced by recombinant techniques by incorporating the DNA expressing the peptide into an expression vector and transforming cells with the expression vector to produce the peptide.

Hence, the present invention relates to any binding molecule, e.g., an antibody or binding fragment thereof which is oriented towards the porcine anti-Mycoplasma surface protein or chimeric polypeptide antibodies of the present invention and display the mentioned properties, i.e. which specifically recognize recombinant VlpA-G. Such antibodies and binding molecules can be tested for their binding specificity and affinity by methods known in the art such as, but not limited to, ELISA and Western Blot and immunohistochemistry.

As an alternative to obtaining immunoglobulins directly from serum, the culture of immortalized B cells, B memory cells, or hybridomas, the immortalized cells can be used as a source of rearranged heavy chain and light chain loci for subsequent expression and/or genetic manipulation. Rearranged antibody genes can be reverse transcribed from appropriate mRNAs to produce cDNA. If desired, the heavy chain constant region can be exchanged for that of a different isotype or eliminated altogether. The variable regions can be linked to encode single chain Fv regions. Multiple Fv regions can be linked to confer binding ability to more than one target or chimeric heavy and light chain combinations can be employed. Once the genetic material is available, design of analogs as described above which retain both their ability to bind the desired target is straightforward. Methods for the cloning of antibody variable regions and generation of recombinant antibodies are known to the person skilled in the art and are described, for example, Gilliland et al., Tissue Antigens 47 (1996), 1-20; Doenecke et al., Leukemia 11 (1997), 1787-1792.

Once the appropriate genetic material is obtained and, if desired, modified to encode an analog, the coding sequences, including those that encode, at a minimum, the variable regions of the heavy and light chain, can be inserted into expression systems contained on vectors which can be transfected into standard recombinant host cells. A variety of such host cells may be used; for efficient processing, for example mammalian or bacterial cells. Typical mammalian cell lines useful for this purpose include, but are not limited to, CHO cells, HEK 293 cells, or NSO cells.

The production of the antibody or analog is then undertaken by culturing the modified recombinant host under culture conditions appropriate for the growth of the host cells and the expression of the coding sequences. The antibodies are then recovered by isolating them from the culture. The expression systems are preferably designed to include signal peptides so that the resulting antibodies are secreted into the medium; however, intracellular production is also possible.

In accordance with the above, the present invention also relates to a polynucleotide encoding the antibody or equivalent binding molecule of the present invention, in case of the antibody preferably at least a variable region of an immunoglobulin chain of the antibody described above. Typically, said variable region encoded by the polynucleotide comprises at least one complementarity determining region (CDR) of the $V_H$ and/or $V_L$ of the variable region of the said antibody.

The person skilled in the art will readily appreciate that the variable domain of the antibody having the above-described variable domain can be used for the construction of other polypeptides or antibodies of desired specificity and biological function. Thus, the present invention also encompasses polypeptides and antibodies comprising at least one CDR of the above-described variable domain and which advantageously have substantially the same or similar binding properties as the antibody described in the appended examples. The person skilled in the art knows that binding affinity may be enhanced by making amino acid substitutions within the CDRs or within the hypervariable loops (Chothia and Lesk, J. Mol. Biol. 196 (1987), 901-917) which partially overlap with the CDRs as defined by Kabat; see, e.g., Riechmann, et al, Nature 332 (1988), 323-327. Thus, the present invention also relates to antibodies wherein one or more of the mentioned CDRs comprise one or more, preferably not more than two amino acid substitutions. Preferably, the antibody of the invention comprises in one or both of its immunoglobulin chains two or all three CDRs of the variable regions of the antibodies illustrated in the Examples.

Binding molecules, e.g., antibodies, or antigen-binding fragments, variants, or derivatives thereof of the invention, as known by those of ordinary skill in the art, can comprise a constant region which mediates one or more effector functions. For example, binding of the C1 component of complement to an antibody constant region may activate the complement system.

Activation of complement is important in the opsonization and lysis of cell pathogens. The activation of complement also stimulates the inflammatory response and may also be involved in autoimmune hypersensitivity. Further, antibodies bind to receptors on various cells via the Fc region, with a Fc receptor binding site on the antibody Fc region binding to a Fc receptor (FcR) on a cell. There are a number of Fc receptors which are specific for different classes of antibody, including IgG (gamma receptors), IgE (epsilon receptors), IgA (alpha receptors) and IgM (mu receptors). Binding of antibody to Fc receptors on cell surfaces triggers a number of important and diverse biological responses including engulfment and destruction of antibody-coated particles, clearance of immune complexes, lysis of antibody-coated target cells by killer cells (called antibody-dependent cell-mediated cytotoxicity, or ADCC), release of inflammatory mediators, placental transfer and control of immunoglobulin production.

Accordingly, certain embodiments of the present invention include an antibody, or antigen-binding fragment, variant, or derivative thereof, in which at least a fraction of one or more of the constant region domains has been deleted or otherwise altered so as to provide desired biochemical characteristics such as reduced effector functions, the ability to non-covalently dimerize, increased ability to localize at the site of Mycoplasma surface protein and deposition, reduced serum half-life, or increased serum half-life when compared with a whole, unaltered antibody of approximately the same immunogenicity. For example, certain antibodies for use in the diagnostic and treatment methods described herein are domain deleted antibodies which comprise a polypeptide chain similar to an immunoglobulin heavy chain, but which lack at least a portion of one or more heavy chain domains. For instance, in certain antibodies, one entire domain of the constant region of the modified antibody will be deleted, for example, all or part of the CH2 domain will be deleted. In other embodiments, certain antibodies for use in the diagnostic and treatment methods described herein have a constant region, e.g., an IgG heavy chain constant region, which is altered to eliminate glycosylation, referred to elsewhere herein as aglycosylated or "agly" antibodies. Such "agly" antibodies may be prepared enzymatically as well as by engineering the consensus glycosylation site(s) in the constant region. While not being bound by theory, it is believed that "agly" antibodies may have an improved safety and stability profile in vivo. Methods of producing aglycosylated antibodies, having desired effector function are found for example in international application WO2005/018572, which is incorporated by reference in its entirety.

In certain antibodies, or antigen-binding fragments, variants, or derivatives thereof described herein, the Fc portion may be mutated to decrease effector function using techniques known in the art. In other cases, it may be that constant region modifications consistent with the instant invention moderate complement binding and thus reduce the serum half-life and nonspecific association of a conjugated cytotoxin. Yet other modifications of the constant region may be used to modify disulfide linkages or oligosaccharide moieties that allow for enhanced localization due to increased antigen specificity or antibody flexibility. The resulting physiological profile, bioavailability and other biochemical effects of the modifications, such as Mycoplasma localization, biodistribution and serum or joint half-life, may easily be measured and quantified using well know immunological techniques without undue experimentation.

In certain antibodies, or antigen-binding fragments, variants, or derivatives thereof described herein, the Fc portion may be mutated or exchanged for alternative protein sequences to increase the cellular uptake of antibodies by way of example by enhancing receptor-mediated endocytosis of antibodies via Fcγ receptors, Fcμ receptors, LRP, or Thy1 receptors or by 'SuperAntibody Technology', which is said to enable antibodies to be shuttled into living cells without harming them (Expert Opin. Biol. Ther. (2005), 237-241). For example, the generation of fusion proteins of the antibody binding region and the cognate protein ligands of cell surface receptors or bi- or multi-specific antibodies with specific sequences biding to Mycoplasma surface protein or chimeric polypeptide as well as a cell surface receptor may be engineered using techniques known in the art. In certain antibodies, or antigen-binding fragments, variants, or derivatives thereof described herein, the Fc portion may be mutated or exchanged for alternative protein sequences or the antibody may be chemically modified to increase its blood brain barrier penetration.

Modified forms of antibodies, or antigen-binding fragments, variants, or derivatives thereof of the invention can be made from whole precursor or parent antibodies using techniques known in the art. Exemplary techniques are discussed in more detail herein. Antibodies, or antigen-binding fragments, variants, or derivatives thereof of the invention can be made or manufactured using techniques that are known in the art. In certain embodiments, antibody molecules or fragments thereof are "recombinantly produced," i.e., are produced using recombinant DNA technology. Exemplary techniques for making antibody molecules or fragments thereof are discussed in more detail elsewhere herein.

Antibodies, or antigen-binding fragments, variants, or derivatives thereof of the invention also include derivatives that are modified, e.g., by the covalent attachment of any type of molecule to the antibody such that covalent attachment does not prevent the antibody from specifically binding to its cognate epitope. For example, but not by way of limitation, the antibody derivatives include antibodies that have been modified, e.g., by glycosylation, acetylation, pegylation, phosphorylation, amidation, derivatization by known protecting/blocking groups, proteolytic cleavage, linkage to a cellular ligand or other protein, etc. Any of numerous chemical modifications may be carried out by known techniques, including, but not limited to specific chemical cleavage, acetylation, formylation, metabolic synthesis of tunicamycin, etc. Additionally, the derivative may contain one or more non-classical amino acids.

In particular preferred embodiments, antibodies, or antigen-binding fragments, variants, or derivatives thereof of the invention will not elicit a deleterious immune response in the animal to be treated, e.g., in a human.

De-immunization can also be used to decrease the immunogenicity of an antibody. As used herein, the term "de-immunization" includes alteration of an antibody to modify T cell epitopes; see, e.g., international applications WO98/52976 and WO00/34317. For example, $V_H$ and $V_L$ sequences from the starting antibody are analyzed and a human T cell epitope "map" from each V region showing the location of epitopes in relation to complementarity determining regions (CDRs) and other key residues within the sequence. Individual T cell epitopes from the T cell epitope map are analyzed in order to identify alternative amino acid substitutions with a low risk of altering activity of the final antibody. A range of alternative $V_H$ and $V_L$ sequences are designed comprising combinations of amino acid substitutions and these sequences are subsequently incorporated into a range of binding polypeptides, e.g., Mycoplasma surface protein or chimeric polypeptide-specific antibodies or immunospecific fragments thereof for use in the diagnostic and treatment methods disclosed herein, which are then tested for function. Typically, between 12 and 24 variant antibodies are generated and tested. Complete heavy and light chain genes comprising modified V and human C regions are then cloned into expression vectors and the subsequent plasmids introduced into cell lines for the production of whole antibody. The antibodies are then compared in appropriate biochemical and biological assays, and the optimal variant is identified.

Monoclonal antibodies can be prepared using a wide variety of techniques known in the art including the use of hybridoma, recombinant, and phage display technologies, or a combination thereof. For example, monoclonal antibodies can be produced using hybridoma techniques including those known in the art and taught, for example, in Harlow et al., Antibodies: A Laboratory Manual, Cold Spring Harbor Laboratory Press, 2nd ed. (1988); Hammerling et al., in: Monoclonal Antibodies and T-Cell Hybridomas Elsevier, N.Y., 563-681 (1981), said references incorporated by reference in their entireties. The term "monoclonal antibody" as used herein is not limited to antibodies produced through hybridoma technology. The term "monoclonal antibody" refers to an antibody that is derived from a single clone, including any eukaryotic, prokaryotic, or phage clone, and not the method by which it is produced. Thus, the term "monoclonal antibody" is not limited to antibodies produced through hybridoma technology. In certain embodiments, antibodies of the present invention are derived from human B cells which have been immortalized via transformation with Epstein-Barr virus, as described herein.

In the well-known hybridoma process (Kohler et al., Nature 256 (1975), 495) the relatively short-lived, or mortal, lymphocytes from a mammal, e.g., spleen cells derived from a mouse, are fused with an immortal tumor cell line (e.g., a myeloma cell line), thus, producing hybrid cells or "hybridomas" which are both immortal and capable of producing the genetically coded antibody of the B cell. The resulting hybrids are segregated into single genetic strains by selection, dilution, and re-growth with each individual strain comprising specific genes for the formation of a single antibody. They produce antibodies, which are homogeneous against a desired antigen and, in reference to their pure genetic parentage, are termed "monoclonal".

Hybridoma cells thus prepared are seeded and grown in a suitable culture medium that preferably contains one or more substances that inhibit the growth or survival of the unfused, parental myeloma cells. Those skilled in the art will appreciate that reagents, cell lines and media for the formation, selection and growth of hybridomas are commercially available from a number of sources and standardized protocols are well established. Generally, culture medium in which the hybridoma cells are growing is assayed for production of monoclonal antibodies against the desired antigen. The binding specificity of the monoclonal antibodies produced by hybridoma cells is determined by in vitro assays such as immunoprecipitation, radioimmunoassay (RIA) or enzyme-linked immunoabsorbent assay (such as an ELISA). After hybridoma cells are identified that produce antibodies of the desired specificity, affinity and/or activity, the clones may be subcloned by limiting dilution procedures and grown by standard methods; see, e.g., Goding, Monoclonal Antibodies: Principles and Practice, Academic Press, pp 59-103 (1986). It will further be appreciated that the monoclonal antibodies secreted by the subclones may be separated from culture medium, ascites fluid or serum by conventional purification procedures such as, for example, protein-A, hydroxylapatite chromatography, gel electrophoresis, dialysis or affinity chromatography.

In another embodiment, lymphocytes can be selected by micromanipulation and the variable genes isolated. For example, peripheral blood mononuclear cells can be isolated from an immunized or naturally immune mammal, e.g., a human, and cultured for about 7 days in vitro. The cultures can be screened for specific immunoglobins, such as IgAs, IgGs or IgMs, that meet the screening criteria. Cells from positive wells can be isolated. Individual Ig-producing B cells can be isolated by FACS or by identifying them in a complement-mediated hemolytic plaque assay. Ig-producing B cells can be micromanipulated into a tube and the $V_H$ and $V_L$ genes can be amplified using, e.g., RT-PCR. The $V_H$ and $V_L$ genes can be cloned into an antibody expression vector and transfected into cells (e.g., eukaryotic or prokaryotic cells) for expression.

Alternatively, antibody-producing cell lines may be selected and cultured using techniques well known to the skilled artisan. Such techniques are described in a variety of laboratory manuals and primary publications. In this respect, techniques suitable for use in the invention as described below are described in Current Protocols in Immunology, Coligan et al., Eds., Green Publishing Associates and Wiley-Interscience, John Wiley and Sons, New York (1991) which is herein incorporated by reference in its entirety, including supplements.

Antibody fragments that recognize specific epitopes may be generated by known techniques. For example, Fab and F(ab')₂ fragments may be produced recombinantly or by proteolytic cleavage of immunoglobulin molecules, using enzymes such as papain (to produce Fab fragments) or pepsin (to produce F(ab')₂ fragments). F(ab')₂ fragments contain the variable region, the light chain constant region and the CH1 domain of the heavy chain. Such fragments are sufficient for use, for example, in immunodiagnostic procedures involving coupling the immunospecific portions of immunoglobulins to detecting reagents such as radioisotopes.

In one embodiment, an antibody of the invention comprises at least one heavy or light chain CDR of an antibody molecule. In another embodiment, an antibody of the invention comprises at least two CDRs from one or more antibody molecules. In another embodiment, an antibody of the invention comprises at least three CDRs from one or more antibody molecules. In another embodiment, an antibody of the invention comprises at least four CDRs from one or more antibody molecules. In another embodiment, an antibody of the invention comprises at least five CDRs from one or more antibody molecules. In another embodiment, an antibody of the invention comprises at least six CDRs from one or more antibody molecules. Exemplary antibody molecules comprising at least one CDR that can be included in the subject antibodies are described herein.

Antibodies of the present invention can be produced by any method known in the art for the synthesis of antibodies, in particular, by chemical synthesis or preferably by recombinant expression techniques as described herein.

In one embodiment, an antibody, or antigen-binding fragment, variant, or derivative thereof of the invention comprises a synthetic constant region wherein one or more domains are partially or entirely deleted ("domain-deleted antibodies"). In certain embodiments compatible modified antibodies will comprise domain deleted constructs or variants wherein the entire CH2 domain has been removed (ΔCH2 constructs). For other embodiments a short connecting peptide may be substituted for the deleted domain to provide flexibility and freedom of movement for the variable region. Those skilled in the art will appreciate that such constructs are particularly preferred due to the regulatory properties of the CH2 domain on the catabolic rate of the antibody. Domain deleted constructs can be derived using a vector encoding an IgG₁ human constant domain, see, e.g., international applications WO02/060955 and WO02/096948A2. This vector is engineered to delete the CH2 domain and provide a synthetic vector expressing a domain deleted IgG₁ constant region.

In certain embodiments, antibodies, or antigen-binding fragments, variants, or derivatives thereof of the present invention are minibodies. Minibodies can be made using methods described in the art, see, e.g., U.S. Pat. No. 5,837,821 or international application WO 94/09817.

In one embodiment, an antibody, or antigen-binding fragment, variant, or derivative thereof of the invention comprises an immunoglobulin heavy chain having deletion or substitution of a few or even a single amino acid as long as it permits association between the monomeric subunits. For example, the mutation of a single amino acid in selected areas of the CH2 domain may be enough to substantially reduce Fc binding and thereby increase Mycoplasma surface protein or chimeric polypeptide localization. Similarly, it may be desirable to simply delete that part of one or more constant region domains that control the effector function (e.g. complement binding) to be modulated. Such partial deletions of the constant regions may improve selected characteristics of the antibody (serum half-life) while leaving other desirable functions associated with the subject constant region domain intact. Moreover, as alluded to above, the constant regions of the disclosed antibodies may be synthetic through the mutation or substitution of one or more amino acids that enhances the profile of the resulting construct. In this respect it may be possible to disrupt the activity provided by a conserved binding site (e.g. Fc binding) while substantially maintaining the configuration and immunogenic profile of the modified antibody. Yet other embodiments comprise the addition of one or more amino acids to the constant region to enhance desirable characteristics such as effector function or provide for more cytotoxin or carbohydrate attachment. In such embodiments it may be desirable to insert or replicate specific sequences derived from selected constant region domains.

The present invention also provides antibodies that comprise, consist essentially of, or consist of, variants (including derivatives) of antibody molecules (e.g., the $V_H$ regions and/or $V_L$ regions) described herein, which antibodies or fragments thereof immunospecifically bind to Mycoplasma surface protein. Standard techniques known to those of skill in the art can be used to introduce mutations in the nucleotide sequence encoding an antibody, including, but not limited to, site-directed mutagenesis and PCR-mediated mutagenesis which result in amino acid substitutions. Preferably, the variants (including derivatives) encode less than 50 amino acid substitutions, less than 40 amino acid substitutions, less than 30 amino acid substitutions, less than 25 amino acid substitutions, less than 20 amino acid substitutions, less than 15 amino acid substitutions, less than 10 amino acid substitutions, less than 5 amino acid substitutions, less than 4 amino acid substitutions, less than 3 amino acid substitutions, or less than 2 amino acid substitutions relative to the reference $V_H$ region, $V_H$-CDR1, $V_H$-CDR2, $V_H$-CDR3, $V_L$ region, $V_L$-CDR1, $V_L$-CDR2, or $V_L$-CDR3. A "conservative amino acid substitution" is one in which the amino acid residue is replaced with an amino acid residue having a side chain with a similar charge. Families of amino acid residues having side chains with similar charges have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Alternatively, mutations can be introduced randomly along all or part of the coding sequence, such as by saturation mutagenesis, and the resultant mutants can be screened for biological activity to identify mutants that retain activity (e.g., the ability to bind Mycoplasma surface protein or chimeric polypeptide).

For example, it is possible to introduce mutations only in framework regions or only in CDR regions of an antibody molecule. Introduced mutations may be silent or neutral missense mutations, e.g., have no, or little, effect on an antibody's ability to bind antigen, indeed some such mutations do not alter the amino acid sequence whatsoever. These types of mutations may be useful to optimize codon usage or improve a hybridoma's antibody production. Alternatively, non-neutral missense mutations may alter an antibody's ability to bind antigen. The location of most silent and neutral missense mutations is likely to be in the framework regions, while the location of most non-neutral missense mutations is likely to be in CDR, though this is not an absolute requirement. One of skill in the art would be able to design and test mutant molecules with desired properties such as no alteration in antigen-binding activity or alteration in binding activity (e.g., improvements in antigen-binding activity or change in antibody specificity). Following mutagenesis, the encoded protein may routinely be expressed and the functional and/or biological activity of the encoded protein, (e.g., ability to immunospecifically bind at least one epitope of Mycoplasma surface protein) can be determined using techniques described herein or by routinely modifying techniques known in the art.

Compositions and Methods of Use

The present invention also provides a pharmaceutical and diagnostic, respectively, pack or kit comprising one or more containers filled with one or more of the above described ingredients, e.g. recombinant chimeric VlpA-G polypeptide, anti-Mycoplasma surface protein antibody, binding fragment, derivative or variant thereof, polynucleotide, vector or cell of the present invention. Associated with such container(s) can be a notice in the form prescribed by a governmental agency regulating the manufacture, use or sale of pharmaceuticals or biological products, which notice reflects approval by the agency of manufacture, use or sale for human administration. In addition, or alternatively, the kit comprises reagents and/or instructions for use in appropriate diagnostic assays. The composition, e.g. kit of the present invention is of course particularly suitable for the risk assessment, diagnosis, prevention and treatment of a disorder which is accompanied with the presence of Mycoplasma.

In further embodiment, the composition further includes loading the one or more of the above described ingredients, e.g. recombinant chimeric VlpA-G polypeptide, anti-Mycoplasma surface protein antibody, binding fragment, derivative or variant thereof, polynucleotide, vector or cell of the present invention, into a nanoparticle. The nanoparticle may be any known in the art, for example polyanhydride nanoparticles. The nanoparticles may help to increase the half-life of the compositions from preventing them leaking out of the vasculature or being taken up into off site targets. Using nanoparticles may allow a lower dosage of the ingredients due to these benefits provided by an increased half-life and better targeting. The nanoparticles may further be functionalized by conjugating with various materials, such as PEG.

In one embodiment, it may be beneficial to use recombinant Fab (rFab) and single chain fragments (scFvs) of the antibody of the present invention, which might more readily penetrate a cell membrane. For example, Robert et al., Protein Eng. Des. Sel. (2008) October 16; S1741-0134, published online ahead, describe the use of chimeric recombinant Fab (rFab) and single chain fragments (scFvs) of monoclonal antibody WO-2 which recognizes an epitope in the N-terminal region of Aβ. The engineered fragments were able to (i) prevent amyloid fibrillization, (ii) disaggregate preformed Aβ1-42 fibrils and (iii) inhibit Aβ1-42 oligomer-mediated neurotoxicity in vitro as efficiently as the whole IgG molecule. The perceived advantages of using small Fab and scFv engineered antibody formats which lack the effector function include more efficient passage across the blood-brain barrier and minimizing the risk of triggering inflammatory side reactions. Furthermore, besides scFv and single-domain antibodies retain the binding specificity of full-length antibodies, they can be expressed as single genes and intracellularly in mammalian cells as intrabodies, with the potential for alteration of the folding, interactions, modifications, or subcellular localization of their targets; see for review, e.g., Miller and Messer, Molecular Therapy 12 (2005), 394-401. In other embodiments, small antibodies may be derived from llamas.

In a further embodiment, co-administration or sequential administration of other protective agents useful for treating an infection or arthritis may be desirable.

A therapeutically effective dose or amount refers to that amount of the active ingredient sufficient to ameliorate the symptoms or condition. Therapeutic efficacy and toxicity of such compounds can be determined by standard pharmaceutical procedures in cell cultures or experimental animals, e.g., $ED_{50}$ (the dose therapeutically effective in 50% of the population) and $LD_{50}$ (the dose lethal to 50% of the population). The dose ratio between therapeutic and toxic effects is the therapeutic index, and it can be expressed as the ratio, $LD_{50}/ED_{50}$.

From the foregoing, it is evident that the present invention encompasses any use of a Mycoplasma surface protein binding molecule comprising at least one CDR of the above described antibody. Preferably, said binding molecule is an antibody of the present invention or an immunoglobulin chain thereof. In addition, the present invention relates to anti-idiotypic antibodies of any one of the mentioned antibodies described hereinbefore. These are antibodies or other binding molecules which bind to the unique antigenic peptide sequence located on an antibody's variable region near the antigen-binding site and are useful, e.g., for the detection of anti-Mycoplasma surface protein antibodies in sample of a subject.

In another embodiment the present invention relates to a diagnostic composition comprising any one of the above described polypeptides, polynucleotides, vectors or cells of the invention and optionally suitable means for detection such as reagents conventionally used in immuno or nucleic acid based diagnostic methods. The antibodies of the invention are, for example, suited for use in immunoassays in which they can be utilized in liquid phase or bound to a solid phase carrier. Examples of immunoassays which can utilize the antibody of the invention are competitive and non-competitive immunoassays in either a direct or indirect format. Examples of such immunoassays are the radioimmunoassay (RIA), the sandwich (immunometric assay), such as enzyme immuno assay (EIA), flow cytometry and the Western blot assay. The antigens and antibodies of the invention can be bound to many different carriers and used to isolate cells specifically bound thereto. Examples of well-known carriers include glass, polystyrene, polyvinyl chloride, polypropylene, polyethylene, polycarbonate, dextran, nylon, amyloses, natural and modified celluloses, polyacrylamides, agaroses, and magnetite. The nature of the carrier can be either soluble or insoluble for the purposes of the invention. There are many different labels and methods of labeling known to those of ordinary skill in the art. Examples of the types of labels which can be used in the present invention include enzymes, radioisotopes, colloidal metals, fluorescent compounds, chemiluminescent compounds, and bioluminescent compounds; see also the embodiments discussed hereinabove.

By a further embodiment, the surface protein binding molecules, in particular antibodies of the present invention may also be used in a method for the diagnosis of a disorder in an individual by obtaining a body fluid sample from the tested individual which may be a blood sample, a lymph sample or any other body fluid sample and contacting the body fluid sample with an antibody of the instant invention under conditions enabling the formation of antibody-antigen complexes. The level of such complexes is then determined by methods known in the art, a level significantly higher than that formed in a control sample indicating the disease in the tested individual. In the same manner, the specific antigen, such as one or more surface proteins or a chimeric polypeptide, bound by the antibodies of the invention may also be used. Thus, the present invention relates to an in vitro immunoassay comprising the binding molecule, e.g., antibody or antigen-binding fragment thereof of the invention.

In this context, the present invention also relates to means specifically designed for this purpose. For example, an antigen- or antibody-based array may be used, which is for example loaded with antigens of the surface proteins or antibodies or equivalent antigen-binding molecules which specifically recognize the antigens of the surface proteins. Design of microarray immunoassays is summarized in Kusnezow et al., Mol. Cell Protcomics 5 (2006), 1681-1696. Accordingly, the present invention also relates to microarrays loaded with Mycoplasma surface proteins, chimeric polypeptides, or binding molecules identified in accordance with the present invention.

The above disclosure generally describes the present invention. Unless otherwise stated, a term as used herein is given the definition as provided in the Oxford Dictionary of Biochemistry and Molecular Biology, Oxford University Press, 1997, revised 2000 and reprinted 2003, ISBN 0 19 850673 2. The contents of all cited references (including literature references, issued patents, published patent applications as cited throughout this application and manufacturer's specifications, instructions, etc) are hereby expressly incorporated by reference; however, there is no admission that any document cited is indeed prior art as to the present invention.

The following Examples are intended to illustrate the above invention and should not be construed as to narrow its scope. One skilled in the art will readily recognize that the Examples suggest many other ways in which the invention could be practiced. It should be understood that numerous variations and modifications may be made while remaining within the scope of the invention.

EXAMPLES

Example 1

In this study, we first established a panel of specimens of precise known immune status for different swine mycoplasmas (MHR, MHS, MHP, and MFLOC) using cesarean-derived, colostrum-deprived (CDCD) pigs as the animal infection model. The animal study was conducted in the Iowa State University Livestock Infectious Disease BSL-2 Isolation Facility (ISU-LIDIF) under the approval of the Iowa State University Institutional Animal Care and Use Committee. Fifty CDCD 8-week-old pigs (Struve Labs, Manning, IA, USA) were randomly allocated onto five groups of treatment housed in separate rooms. Within each group, 10 pigs were housed by 2 pigs/pen, sharing nipple drinkers and fed an antibiotic-free commercial diet twice a day. Specific information related to source of inoculum, inoculum preparation, and route/s of inoculation for each group is shown in Table 2 (Strasser et al., 1992; Kobisch, 1983; Hagedorn-Olsen et al. 1999; Gonzalez et al., 2017). Prior to the inoculation, the pig negative mycoplasma status was evaluated by pathogen-specific real-time polymerase chain reaction (qPCR) and enzyme-linked immunosorbent assay (ELISA) on serum samples, oral fluids, and tonsil scrapes (MHS group) collected at day post-inoculation (DPI) 0. All pigs were closely observed twice daily for clinical signs throughout the study.

TABLE 2

Mycoplasma strains, inoculum preparation, dose, and route of inoculation used during experimental inoculations.

| | | Inoculum | | | Inoculation | |
| --- | --- | --- | --- | --- | --- | --- |
| Group (No pigs) | Strain [a] | Passage/media [b] | Concentration [c] | Reference | Route [d] | Vol (mL) |
| M. hyorhinis (10) | 38983 | 3$^{rd}$/Friis | 3.2 × 10$^8$ CFU/ml | Friis and Feenstra (1994); Lin et al. (2006) | Tonsillar swabbing Intraperitoneal | 2 2 |
| M. hyosynoviae (10) | 34428 | 3$^{rd}$/Difco + mucin + turkey serum | 2.1 × 10$^9$ CFU/ml | Ross and Karmon (1970); Ross et al. (1971) | Tonsillar swabbing Intranasal (0.5 mL/nostril) Intravascular (ear vein) | 2 1 1 |
| M. hyopneumoniae (10) | 232 | Lung inoculum/Friis | 1.0 × 10$^6$ CCU/ml | Friis (1971) | Intratracheal | 1 |
| M. flocculare (10) | 27399 | 59$^{th}$/Friis | 1.0 × 10$^5$ CCU/ml | Friis (1971) | Tonsillar swabbing Intranasal Intratracheal | 2 1 1 |
| Negative control (10) | Friis medium | — | — | — | Intranasal (0.5 mL/nostril) | 1 |

[a] M. hyorhinis strain 38983 was originally field-isolated from a 9-week-old pig presenting pleuritic. M. hyosynoviae strain 34428 was originally field-isolated from a 15-week-old pig with arthritis. M. flocculare strain 27399 was originally isolated from a porcine pneumonic lung. M. hyopneumoniae strain 11 was passaged repeatedly in disease-free pigs resulting in strain 232.
[b] M. hyopneumoniae strain 232 infected lung tissue was homogenated, diluted 1:100 in Friis medium and used as inoculum.
[c] CFU/mL: colony-forming units per mL; CCU/mL: color-changing units per mL. The purity of original seeds and final inoculum were evaluated by qPCR and microscopy staining (×1000 magnification) to rule out bacterial contamination including other Mycoplasma spp.
[d] Routes of inoculation references: M. hyopneumoniae and M. flocculare (Strasser et al., 1992); M. hyorhinis (Kobisch, 1983); M. hyosynoviae (Hagedorn-Olsen et al., 1999); tonsillar swabbing (González et al., 2017).

Sample Collection

Blood samples (n=450) were collected from all pigs individually on DPIs −3, 0, 3, 7, 10, 14, 17, 21, 24, 28, 35, 42, 49, and 56. Blood was drawn from the jugular vein or cranial vena cava using single-use serum separation tubes. Samples were then centrifuged 1,5000×g for 15 minutes and serum stored at −80° C. until used. Pen oral fluid samples (1 rope/pen; 5 pens/group) were collected daily from each group between DPI 0 to 56 using cotton ropes as described elsewhere (Pricket et al. 2008). Tonsil scraping samples were collected from individual pigs in the MHS group on DPI 0 to verify their negative status. At 56 DPI, survival pigs were humanely euthanized by penetrating captive bolt (Accles and Shelvoke, Ltd., Sutton Coldfield, UK) followed by exsanguination, and gross lesions were observed. Histopathology was performed in a subset of pigs with gross lesions.

*Mycoplasma hyorhinis* and *Mycoplasma hyosynoviae* DNA extraction and real-time PCRs Pathogen-specific qPCRs were used to confirm infection, patterns of shedding overtime within inoculation groups, and absence of cross-contamination between groups (rooms) during the observation period (−3 to 56 DPI). Total nucleic acids in each biological sample were extracted using the MagMAXTM Pathogen RNA/DNA kit (Applied Biosystems, Life Technologies, Carlsbad, CA, USA). In brief, 100 µl of samples, 20 µl of Nucleic Acid Binding Beads, and 150 µl of lysis/binding solution in absolute isopropanol were mixed in a 96 well round bottom plate. The DNA extraction was done using an automated 96-well magnetic particle processor (Thermo Scientific Kingfisher Flex, Thermo Fisher Scientific, Pittsburg, PA, USA) as per manufacturer's instruction. Different mycoplasmas (MHR, MHS, MHP, MFLOC) were cultivated in growth culture medium, and nucleic acids-free extraction reagents were extracted together with the biological samples as positive and negative extraction controls.

Primers and procedures for MHR and MHS qPCRs have been described elsewhere (Gomes Neto et al., 2015) except that MHR primers sequences were modified (SEQ ID NO:3 MHR-F 5'-GCATGTTGAACGGGATGTAGCATT-3'; SEQ ID NO:4 MHR-R 5'-TGAAGCTGTGAAGCTCCTTTCT-ATTACTC-3'). In brief, 2.5 µl extracted DNA, 0.1 µl forward primer (0.1 mM), 0.1 µl reverse primer (0.1 mM), 12.5 µl Qiagen® quantitect SYBR Green (Qiagen®, Hilden, Germany), and 9.8 µl Qiagen nuclease free water (Qiagen). The real-time PCR reaction was conducted on an ABI 7500 Fast instrument (Applied Biosystem®, Foster city, Calif., USA) as follow: 95° C. for 15 minutes; 45 cycles of 94° C. for 15 seconds and 61° C. for 30 seconds; 95° C. for 15 seconds, and 60° C. for 1 minute. The results were analyzed using an automatic baseline setting. Quantification cycle (Cq) values <40 and melting temperatures of 75.9±1° C. and 81.5±1° C. were considered positive for MHR and MHS, respectively. 2.4. *Mycoplasma hyorhinis* chimeric VlpA-G recombinant polypeptide-based indirect ELISA ("MHR Vlp ELISA").

The MHR genes coding for the seven known variable surface lipoproteins (VlpA, VlpB, VlpC, VlpD, VlpE, VlpF, and VlpG) were in vitro synthesized (Shanghai Genery Biotech Co., Ltd., Shanghai, China) in tandem using linker space sequences with the addition of a 3' terminal thioredoxin (TRX) tag followed by a 6x histidine (His) tag (FIG. 1. (SEQ ID NO:1)). After amplification by PCR, the amplicon (1,122-nt) was cloned into a pET32a expression plasmid (FIG. 1), confirmed by sequencing (Genewiz Inc., Suzhou, China), and subsequently used to transform the *Escherichia coli* BL21(DE3) host strain (Invitrogen, Carlsbad, CA, USA). The transformants were grown in Luria-Bertani (LB) medium (Invitrogen, Thermo Fisher Scientific, Grand Island, NY, USA) containing 100 g/ml of ampicillin at 37° C. with shaking at 250 rpm. When an A600 value of 0.6 was reached, 1 mM IPTG (isopropyl-D-thiogalactopyranoside) was added to induce over-expression of chimeric VlpA-G, and cultures were grown for 3 hours at 37° C. Cells were harvested by centrifugation at 3,500 x g for 15 min, resuspended in lysis buffer (20 mM Tris-HC1 and 500 mM NaCl, pH 8.0), and disrupted by ultrasonication (Vibra-Cell sonicator; Sonics & Materials, Newtown, CT, USA). The crude extracts were centrifuged at 15,000 g for 30 min at 4° C., and the soluble expression of the histidine (His) tag-fused chimeric VlpA-G polypeptide (36.8. kDa) was confirmed by SDS-PAGE analysis. VlpA-G (374 aa) was purified from the soluble fraction by sequential use of Ni-chelating SFF affinity chromatography (GE Healthcare, Pittsburgh, PA, USA), HiTrap Phenyl High Performance (HP) (GE Healthcare) hydrophobic interaction chromatography, and HiTrap Q HP anion exchange chromatography (GE Healthcare), consecutively applied according to the manufacturer's instructions. Protein elutions were dialyzed against phosphate buffered saline (PBS, pH 8) at 4° C. Chimeric VlpA-G polypeptide had the predicted size, as determined by SDS-PAGE and Western blot. No cleaving products were detected.

Ninety-six well polystyrene ELISA plates (Nunc, Thermo Fisher Scientific, Agawam, MA, USA) were coated with 100 µl of chimeric VlpA-G recombinant polypeptide (0.8 µg/ml) in PBS (pH 7.4) and incubated at 4° C. for 16 h. Plates were washed 5 times with PBS-T (0.1% Tween 20), blocked with a 1% (w/v) bovine serum albumin (BSA, Jackson ImmunoResearch Inc., West Grove, PA, USA) solution, incubated at room temperature (RT; 20-23° C.) for 2 h, dried at 37° C. for 3 h, and stored at 4° C. in a sealed bag with desiccant packs. Serum samples, including positive and negative internal controls tested in duplicate, were diluted 1:50, incubated at 37° C. for 1 hour, and washed 5 times with PBS-T. Then, 100 µl of peroxidase (HRP)-conjugated goat anti-pig IgG (Fc) antibody (Bethyl Laboratories Inc., Montgomery, Tx., USA) diluted 1:25,000 was added to each well and the plates were incubated at 37° C. for 1 h. After a washing step, the reaction was visualized by adding 100 µl of tetramethylbenzidine-hydrogen peroxide (TMB, Surmodics IVD, Inc., Eden Prairie, MN, USA) substrate solution to each well, and at RT for 5 min. The reaction was terminated by adding 100 µl of stop solution (Surmodics IVD, Inc.) to each well. The absorbance was measured at 450 nm using an automated plate reader (Molecular Devices, Sunnyvale, CA, USA). Serum antibody responses were expressed as sample-to-positive (S/P) ratios.

*Mycoplasma hyosynoviae* Tween 20 extracted surface proteins-based indirect ELISA ("MHS T20 ELISA") A pure culture of MHS was grown in Difco medium, supplemented with mucin and turkey serum, and incubated at 37° C. as described elsewhere (Ross and Karmon, 1970; Ross et al., 1971). The cells were harvested by centrifugation and washed three times with PBS (pH 7.4). The surface proteins were extracted by mixing the bacterial pellet with a 2% Tween 20 solution (Sigma-Aldrich, St. Louis, MO USA), incubating the mix at 37° C. for 90 min, and final centrifugation at 59,573 x g for 30 min to remove cell debris. The supernatant was collected, diluted 1:100 in PBS (pH 7.4), and used as antigen to coat (2-3 µg/well) 96-wells plates (Nunc, Thermo Fisher Scientific), subsequently incubated at 4° C. for 16 hours. Plates were washed with PBS-T, blocked with 1% BSA-based blocking solution, dried, and stored at 4° C. until use. Plates were loaded with 100 µl of sera diluted 1:50, incubated at 37° C. for 1 hour, and washed 5 times with PBS-T. Then, 100 µl of HRP-conjugated goat anti-pig IgG (Fc) antibody (Bethyl Laboratories Inc.) diluted 1:17,000 was added to each well and the plates incubated at 37° C. for 1 hour. After a wash, the reaction was visualized by adding 100 µl of TMB (Surmodics IVD, Inc.) solution to each well, and incubated at RT for 5 min. The reaction was stopped by adding 100 µl of stop solution (Surmodics IVD, Inc.) and the absorbance of each well was measured at 450 nm in an ELISA plate reader (Molecular Devices). ELISA results were expressed as S/P ratios.

Data Analysis

Statistical analyses were performed using commercial statistical software (SAS® Version 9.4, SAS® Institute, Inc., Cary, NC). A Fisher Exact Test was used to evaluate differences (p<0.05) in the S/P isotype-specific (IgG, IgA) antibody responses between MHR and MHS inoculation group compared to the negative control group by day post-inoculation. Receiver operating characteristic curve (ROC) analysis was used to calculate different S/P cutoff values and associated diagnostic sensitivity, and diagnostic and analytical specificities (and 95% confidence intervals) of IgG/IgA MHR and MHS indirect ELISAs. Serum samples (n=148) collected from each group of treatment (MHR, MHS, MHP, MFLOC) before inoculation (DPI −3 and 0) plus all samples collected from the negative control group throughout the study (DPI −3 to 56) were used to estimate the diagnostic specificity. The overall diagnostic sensitivity of the MEM Vlp ELISA was evaluated on positive samples (n=68) collected from MHR inoculated pigs between DPI 17 and 56. The overall diagnostic sensitivity of the MHS T20 ELISA was evaluated on positive samples (n=63) collected from MHS inoculated pigs between DPI 21 and 56. Selected S/P cutoff values for both MHR Vlp ELISA and MHS T20 ELISA were used to determine time of detection and overtime detection through the observational period. The analytical specificity of both ELISAs were evaluated using samples (n=320; MHR) (n=318; MHS) collected between DPI 7 and 56 from animals inoculated with heterologous mycoplasma species.

Results

*Mycoplasma hyorhinis* and *Mycoplasma hyosynoviae* clinical signs

Clinical signs observed in MHR inoculated pigs including lameness, joint swelling, rough hair coat, and loss of condition were observed in eight (8/10) pigs from DPI 11 throughout the study (DPI 56). Only two pigs (2/10), housed within the same pen, never developed clinical signs. Among the clinically affected pens (4/5), rough hair coat, loss of condition, and mild front and hind limb lameness were observed in two pens by DPI 11. At DPI 13, lameness with or without joint swelling, rough hair coats, depression or reluctance to move, and loss of conditions was observed in at least one of the two pigs within each affected pen (4/5). Two animals within the same pen were euthanized at DPI 24 due to anorexia and inability to ambulate because of polyarthritis and polyserositis. Lameness, rough hair coat, joint swelling, and loss of condition in all affected pens remained relatively unchanged from initial observations through the end of the study (DPI 56).

Clinical signs consistent with MHS-arthritis were observed in seven (7/10) MHS inoculated pigs from DPI 8 until DPI 28. Clinical signs were first observed on DPI 8 in two pigs in two different pens. Clinical signs included swollen hocks, leg stiffness, and reluctance to move or altered gait. At DPI 10, seven animals (7/10) in four pens (4/5) were clinically affected. Clinical signs were not observed in three pigs, one of which died during blood collection on DPI 10.

*Mycoplasma hyorhinis* and *Mycoplasma hyosynoviae* bacteremia and bacterial shedding detected by qPCR Bacteremia was specifically detected by qPCR only in one serum sample collected from one MHR inoculated pig at DPI 10 (Cq 35.9). Likewise, MHS DNA was detected in two serum samples collected from two MHS inoculated pigs, housed in two different pens, at DPI 3 (Cq 33.3) and DPI 7 (Cq 34.4), respectively.

Figure 2:
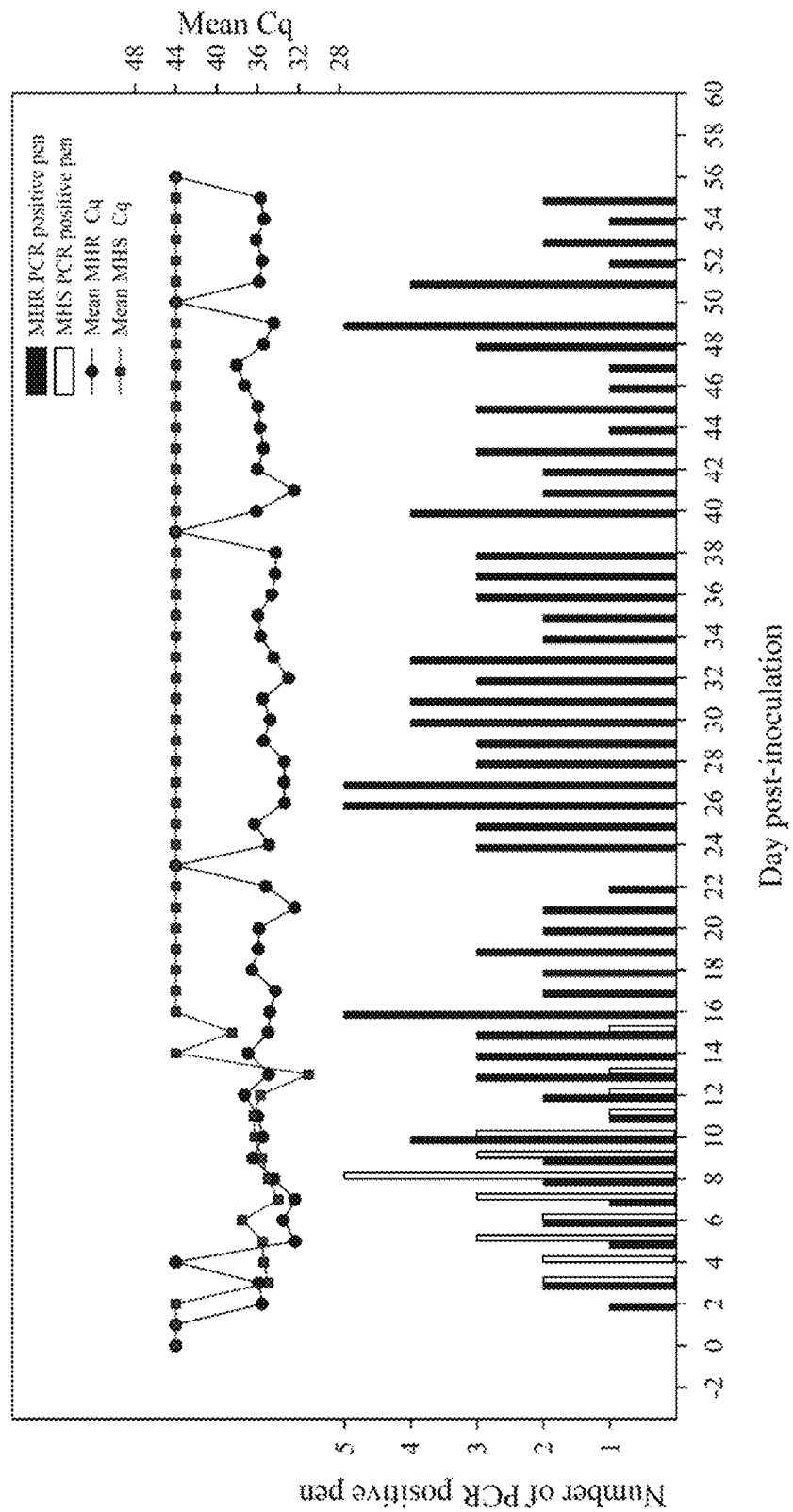
FIG. 2 is a graphical representation of the detection of *Mycoplasma hyorhinis* (MHR) and *Mycoplasma hyosynoviae* (MHS) shedding by qPCR in pen-based oral fluids collected independently from MHR- and MHS-inoculated pigs over the course of 56 days. Results are presented as mean adjusted quantification cycle (Cq) (40—sample Cq) of positive samples, and number of oral fluid PCR positive pens.

In the MHR inoculated group, bacterial shedding was detected intermittently in pen oral fluids collected from DPI 2, ten days prior to the onset of clinical signs, until the end of the study (DPI 56). In MHS inoculated pigs, bacterial shedding was detected daily in oral fluids collected from 1 or more pens from DPI 3, four days prior to the onset of the clinical signs, to DPI 15. Peak of MHS oral fluid shedding (100% pens) was detected at DPI 8. The percent of MHR and MHS real-time PCR oral fluid positive pens and the average Cq values by DPI are presented in FIG. 2.

Figure 3:
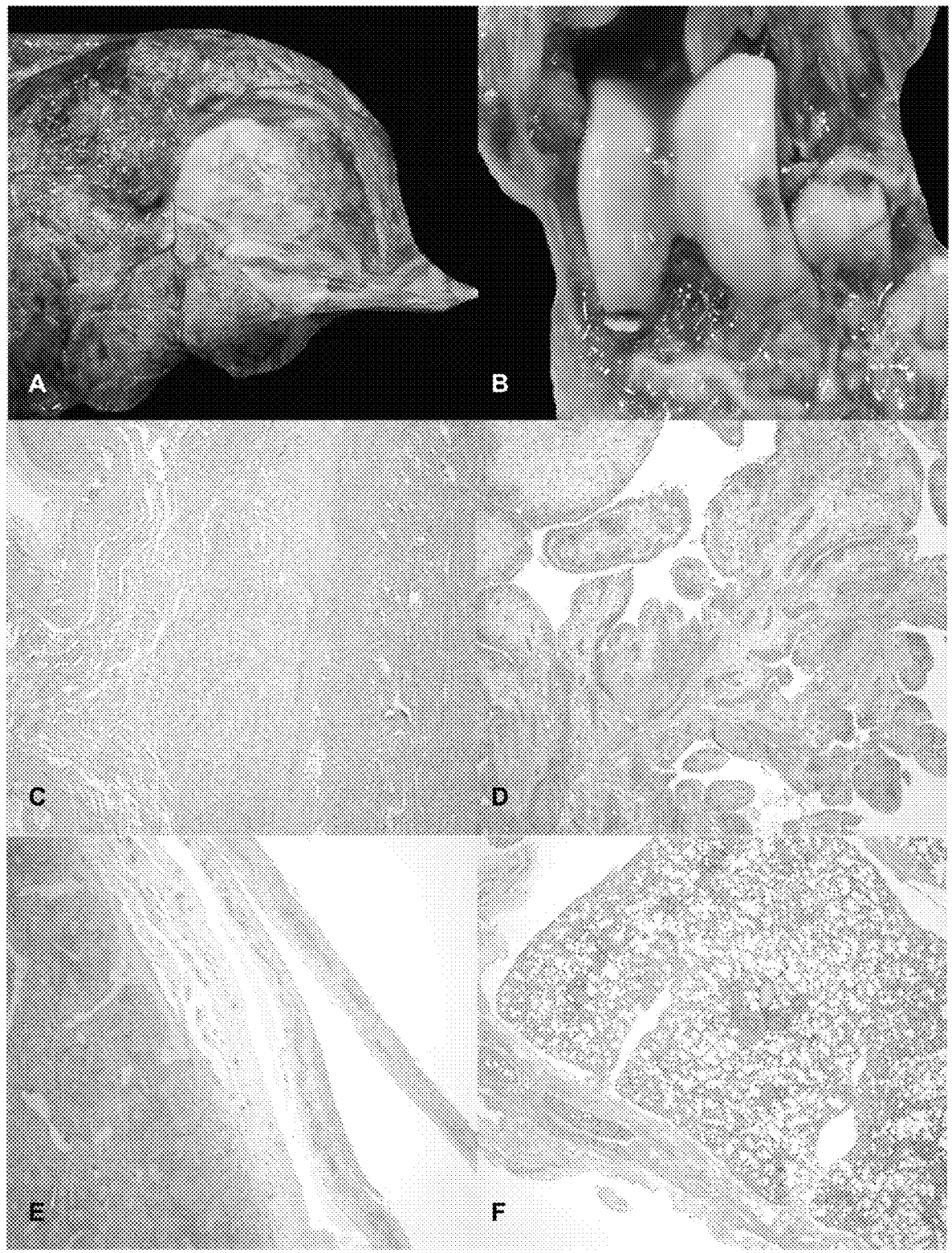
FIG. 3 shows the pathologic lesions of *Mycoplasma hyorhinis* at necropsy. Fibrosing epicarditis (A); Proliferative arthritis (B); Fibrosing epicarditis (C); Proliferative and lymphoplasmacytic synovitis (D); Fibrosing and lymphocytic serositis (spleen; E); Fibrosing pleuritic (G).

*Mycoplasma hyorhinis* and *Mycoplasma hyosynoviae* pathologic lesions at necropsy Fibrosing polyserositis lesions, i.e., fibrosing epicarditis, fibrosing pleuritis, fibrinous and fibrosing arthritis, and fibrosing peritonitis consistent with MHR infection were observed in nine (9/10) MHR inoculated pigs at necropsy (FIG. 3). Increased joint fluid volume was observed in three (3/10) MHS inoculated pigs at necropsy (FIG. 3).

Kinetics of the antibody responses to *Mycoplasma hyorhinis* and *Mycoplasma hyosynoviae*

Figure 4:
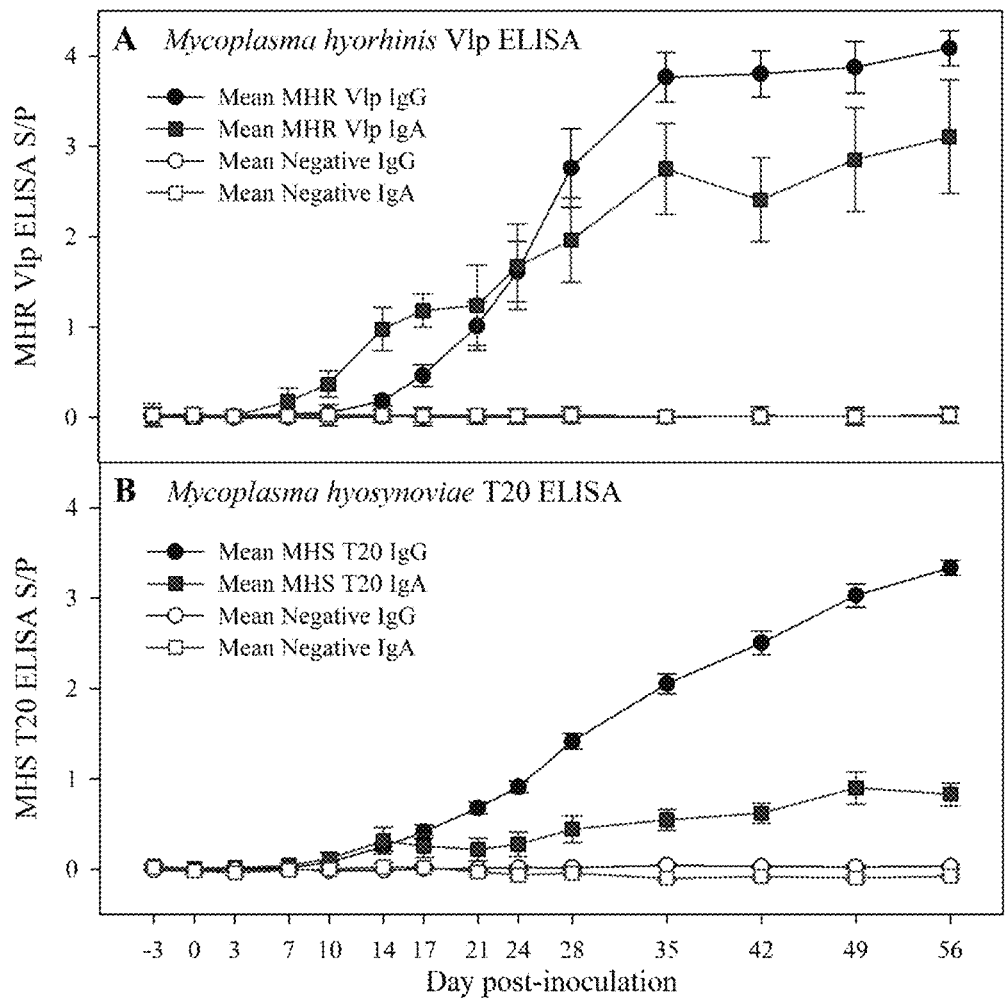
FIG. 4 is a graphical representation of the kinetics of the antibody responses to *Mycoplasma hyorhinis* (MHR) and *Mycoplasma hyosynoviae* (MHS) over the course of 59 days. Data are presented as ELISA sample-to-positive (S/P) ratios of serum IgG (blue lines) or IgA (red lines) responses (means and standard errors) over time measured by a MHR Vlp ELISA (A) or MHS T20 ELISA (B) in MHR- or MHS-inoculated pigs, respectively, and compared to the response in the negative control group.

Prior to inoculation (DPI-3 and 0), no serum antibody response was detected in any pig among the different inoculation groups. Pigs in the negative control group remained seronegative to the swine mycoplasmas used for experimental inoculation throughout this study. The IgG and IgA antibody responses (S/P ratios) to MHR and MHS in serum by time post-inoculation (DPI −3 to 56) are presented in FIG. 4A and FIG. 4B, respectively.

Compared to pigs in the negative control group, a significant (p<0.05) antibody response was first detected in MHR inoculated pigs between DPI 10 (IgA) to DPI 14 (IgG). The IgG and IgA antibody response to MHR increased with time post-exposure throughout the study. The MHR IgA antibody response was detectable earlier than the IgG response. The IgA and IgG antibody response against MHR was significantly different on DPI 10 to 17 and 35 to 42 (Fisher Exact Test, p<0.05). Likewise, for MHS inoculated pigs, the first significant (p<0.05) antibody response compared to negative control group was detected between DPI 10 (IgG) to DPI 24 (IgA), increasing thereafter until the end of the study. However, the IgG antibody response against MHS was significantly higher (p<0.05) than the IgA response from DPI 21 to 56.

Figure 5:
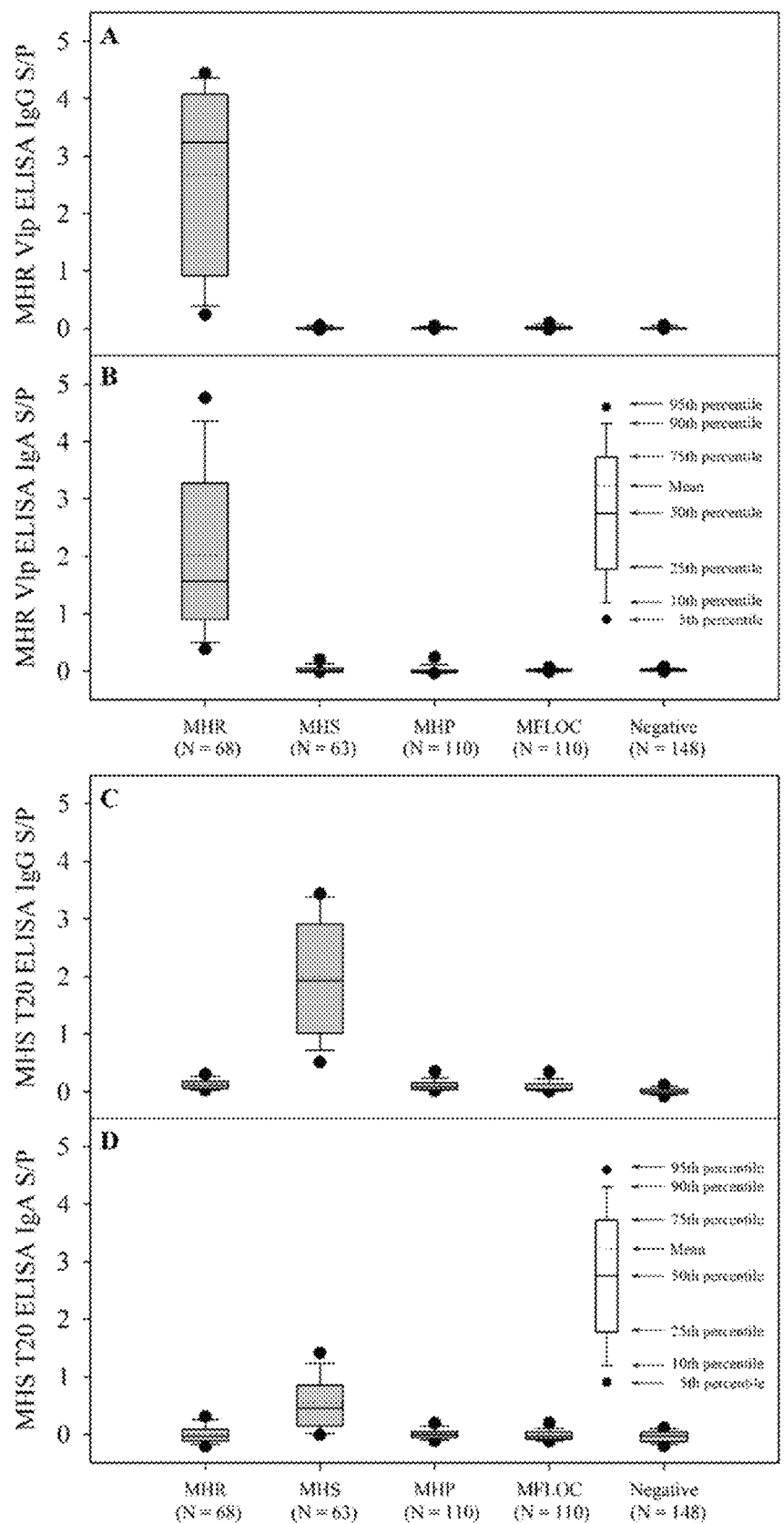
FIG. 5 is a graphical representation of the distribution of *Mycoplasma hyorhinis* (MHR) Vlp ELISA and *Mycoplasma hyosynoviae* (MHS) T20 ELISA sample-to-positive (S/P) IgG (A, C) and IgA (B, D) responses in serum samples collected from pigs inoculated with MHR, MHS, *Mycoplasma hyopeumoniae* (MHP), *Mycoplasma floculare* (MFLOC) or with culture medium (negative control).
Figure 6:
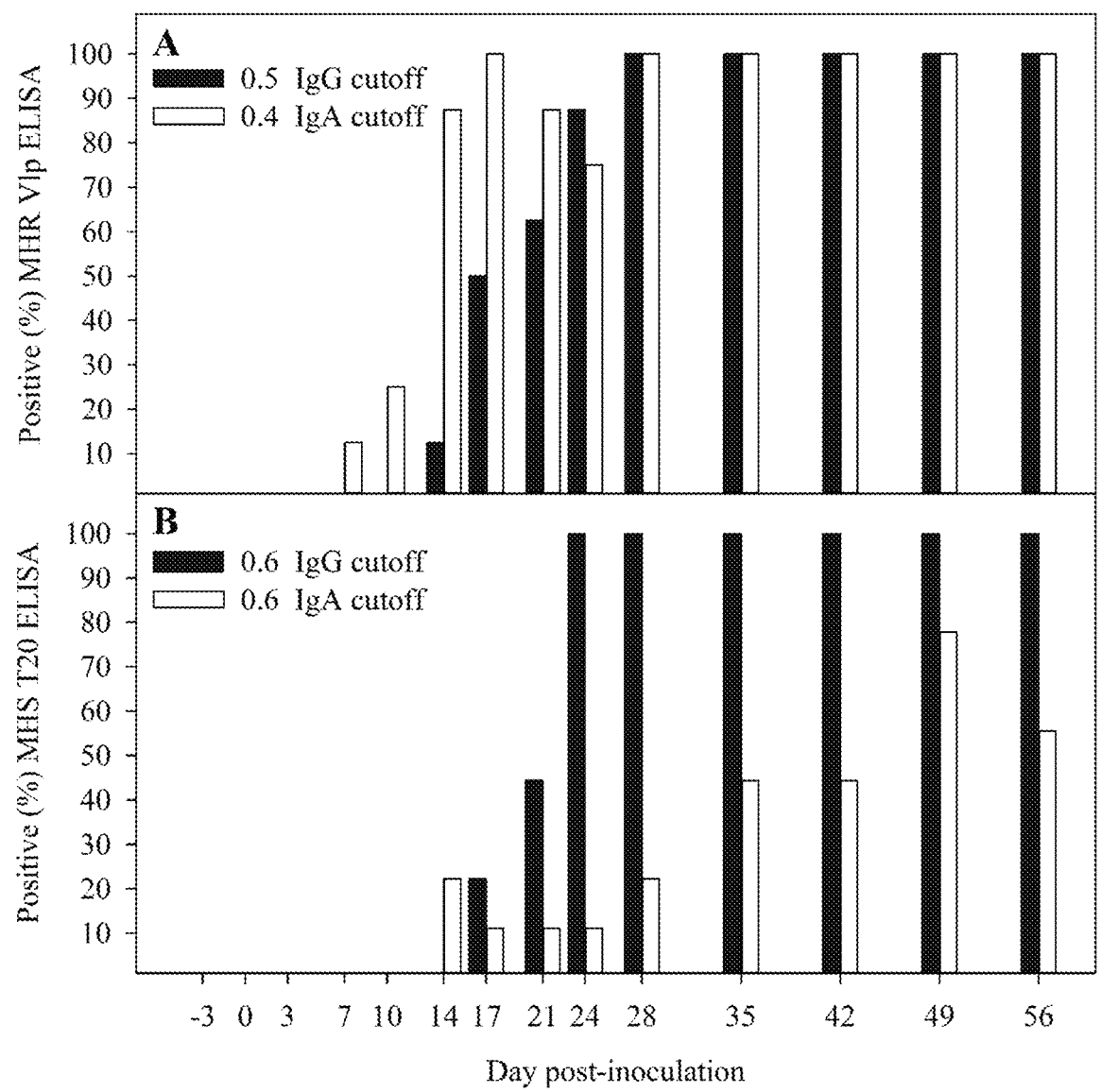
FIG. 6 is a graphical representation of the proportion of ELISA positive serum IgG (blue bars) and IgA (red bars) samples over time following exposure to *Mycoplasma hyorhinis* (MHR (A)) or *Mycoplasma hyosynoviae* (MHS (B)). A S/P≥0.50 cutoff for MHR Vlp IgG and 0.4 for MHR Vlp IgA ELISAs and S/P ≥0.6 for MHS T20 IgG and IgA ELISAs could be selected to ensure 100% diagnostic and analytical specificities

Diagnostic performance of *Mycoplasma hyorhinis* and *Mycoplasma hyosynoviae* ELISAs The diagnostic performance of the MHR Vlp and MHS T20 indirect ELISAs were assessed by analyzing the distribution of the ELISA IgG and IgA S/P values in serum samples (n=499) collected from all treatment groups (FIG. 5) using a ROC curve analyses. The MHR Vlp ELISA showed excellent diagnostic discrimination between positive and negative samples for both MHR Vlp IgG (FIG. 5A) and IgA (FIG. 5B). However, while the MHS T20 ELISA showed a good discrimination for IgG (FIG. 6A), the test performance for IgA was comparatively lower (FIG. 6B).

The diagnostic sensitivity (DxSe) and specificity (DxSp), and the analytical specificity (AnSp) of the IgG and IgA ELISAs associated to different S/P cutoff values for MHR Vlp ELISA and MHS T20 ELISA are provided in Table 3 and Table 4, respectively. FIG. 5A show the proportion of positive serum IgG and IgA samples detected overtime by the MEM Vlp ELISA using an S/P cutoff value of 0.5 for IgG and 0.4 for IgA, which provided 100% of DxSp and AnSp. Likewise, FIG. 6B show the proportion of positive samples detected overtime by the MHS T20 ELISA using a cutoff of 0.6 for both IgG and IgA to ensure 100% DxSp and AnSp.

TABLE 3

Diagnostic performance of the *Mycoplasma hyorhinis* isotype-specific Vlp ELISA based on experimental samples of known status.

| Ig | Cutoff (S/P) | Diagnostic sensitivity (95% CI) | Diagnostic specificity (95% CI) | Analytical specificity (95% CI) |
|---|---|---|---|---|
| IgG | 0.1 | 98.4 (91.6, 100) | 98.6 (96.0, 99.7) | 97.5 (95.1, 98.9) |
|  | 0.2 | 98.4 (91.6, 100) | 100 (98.3, 100) | 99.4 (97.7, 99.9) |
|  | 0.3 | 93.8 (84.8, 98.3) | 100 (98.3, 100) | 99.4 (97.7, 99.9) |
|  | 0.4 | 90.6 (80.7, 96.5) | 100 (98.3, 100) | 99.7 (98.3, 100) |
|  | 0.5 | 87.5 (76.9, 94.5) | 100 (98.3, 100) | 100 (98.8, 100) |
| IgA | 0.1 | 100 (94.4, 100) | 98.2 (95.3, 99.5) | 89.3 (85.4, 92.5) |
|  | 0.2 | 100 (94.4, 100) | 100 (97.45, 100) | 96.2 (93.5, 98.0) |
|  | 0.3 | 98.4 (91.6, 100) | 100 (98.3, 100) | 99.1 (97.3, 99.8) |
|  | 0.4 | 96.9 (89.2, 99.6) | 100 (98.3, 100) | 100 (98.9, 100) |
|  | 0.5 | 92.2 (82.7, 97.4) | 100 (98.3, 100) | 100 (98.9, 100) |

TABLE 4

Diagnostic performance of the *Mycoplasma hyosynoviae* isotype-specific T20 ELISA based on experimental samples of known status.

| Ig | Cutoff (S/P) | Diagnostic sensitivity (95% CI) | Diagnostic specificity (95% CI) | Analytical specificity (95% CI) |
|---|---|---|---|---|
| IgG | 0.1 | 100 (94.3, 100) | 88.5 (83.3, 92.6) | 55.2 (49.6, 60.8) |
|  | 0.2 | 100 (94.3, 100) | 99.0 (96.4, 99.9) | 82.5 (77.9, 86.6) |
|  | 0.4 | 100 (94.3, 100) | 99.5 (97.3, 100) | 97.1 (94.6, 98.7) |
|  | 0.5 | 96.8 (89.0, 99.6) | 100 (98.2, 100) | 99.7 (98.2, 100) |
|  | 0.6 | 93.7 (84.5, 98.2) | 100 (98.2, 100) | 100 (98.8, 100) |
| IgA | 0.1 | 81.0 (69.1, 89.8) | 88.5 (83.3, 92.6) | 84.0 (79.5, 87.9) |
|  | 0.2 | 73.0 (60.1, 83.4) | 98.5 (95.7, 99.7) | 92.7 (89.2, 95.3) |
|  | 0.4 | 57.1 (44.1, 69.5) | 100 (98.2, 100) | 98.7 (96.8, 99.7) |
|  | 0.5 | 41.3 (29.0, 54.4) | 100 (98.2, 100) | 99.7 (98.2, 100) |
|  | 0.6 | 38.1 (26.2, 51.2) | 100 (98.2, 100) | 100 (98.8, 100) |

Discussion

Over the last several years, there has been a reported increase of MHR-associated disease and MHS-associated arthritis in growing pigs resulting in significant production losses due to reduced growth rate, increased mortality or culling, and antibiotic costs (Rovira, 2009; Gomes-Neto et al., 2012). Field diagnosis is mostly based on clinical signs and gross lesions, which is complicated by the presence of other bacteria (e.g., *Haemophilus parasuis, Streptococcus suis*, and *Erysipelothrix rhusiopathiae*) causing fibrinous lesions comparable to those produced by MEM and MHS (Turner, 1982; Hariharan et al., 1992). Conventionally, the diagnosis of mycoplasma-associated arthritis is achieved by demonstration of the agent from tissue showing typical lesions, including swabs collected from serosal surfaces, join fluid or fibrin from affected locations (Hayflick and Chanock, 1965; Gois et al., 1969; Ross and Whittlestone, 1983; Friis and Feesntra, 1994; Makhanon et al., 2012). Although highly diagnostically specific, the identification of the etiologic agent by conventional methods can be difficult and time-consuming.

Despite the common occurrence and production losses attributed to MHR-associated disease and MHS-associated arthritis, the availability of well-characterized differential serologic assays and the implications that may exist between PCR results from oral fluids and clinical signs is limited. Accordingly, the objectives of this study were to 1) improve antemortem diagnostic tools for early detection and differential diagnosis of MHR and MHS infections and 2) describe the detection of either agent in oral fluids by PCR and clinical disease.

The suitability of a chimeric polypeptide based on a family of size-variant major membrane surface Vlp specific of MHR, and a cocktail of surface proteins extracted from MHS cultures as antemortem biomarkers for serodiagnosis of MHR-associated disease and MHS-associated arthritis was evaluated on serum samples of known status in an ELISA platform.

The MHR Vlp family is composed of seven known members (i.e., VlpA, VlpB, VlpC, VlpD, VlpE, VlpF, and VlpG) with a continuous hydrophilic sequence projected externally from the bacteria membrane, and containing critical regions subject to immune recognition (Rosengarten and Wise, 1990; Rosengarten and Wise, 1991; Yogev et al., 1991; Cleavinger et al., 1994). The Vlp system, unique to MHR, provides MHR with a mutational strategy based on high frequency phase variation in expression and size by intragenic recombination to generate antigenic diversity among strains, which may be involved in cytoadhesion, evasion of the host immune response, and induction of chronic infections (Rosengarten and Wise, 1990; Rosengarten and Wise, 1991; Yogev et al., 1991; Yogev et al., 1995). To overcome the divergence in the sequence among vlp genes and the variation in their expression between MHR strains (Citti et al., 2000), we designed a chimeric VlpA-G broad-spectrum MHR antigen derived from the seven known vlp genes ligated in-frame with an intervening linker, cloned and overexpressed using an *E. coli* expression system.

Analyzing the kinetics of the antibody response to the MHR chimeric VlpA-G antigen, we found particularly remarkable the early IgA response detected in serum by DPI 7, one week before the first clinical signs. The question of whether this IgA response might allow for detection of subclinical infections in presence of maternal IgG antibodies, as demonstrated for PRRSV (Rotolo et al. 2018), would need to be further investigated. The IgG response appeared later, between DPI 14-17, concomitantly with the progression of the clinical signs. Both IgA and IgG VlpA-G responses increased throughout the study, and their duration needs to be further investigated under experimental and field conditions.

For MHS, there is a lack of information regarding specific biomarkers of infection. Typically, albeit with variations in the methodology for bacterial culture and antigen preparation, MHS surface proteins have been widely used for ELISA development (Kobisch and Friis,1996; Pedersen et al., 1996; Nielsen et al., 2005; Gomes Neto et al., 2014). Previously, Gomes Neto et al. (2015) used an ELISA based on surface proteins extracted from MHS cultures following the same procedure described herein. While they reported late seroconversion (DPI 35-49) and low overall detection rate (2/4 pigs) in a pilot-size animal study, our MHS T20 ELISA was capable of detecting antibodies earlier, between 14 to 17 DPI, approximately one week after the appearance of the first clinical signs and concomitantly with the cessation of the bacterial shedding in oral fluids. Although based on the same antigen, the differences in test performance could be due to differences in assay design/development, including test procedure and composition of ELISA reagents. Unlike the antibody kinetics described for MHR, the IgG response to MHS was significantly higher overtime, and provided better diagnostic performance than the IgA response. The kinetics of the isotype-specific antibody response depends, among other factors, on the type of infection, specimens tested, antigen-specific response, and the intrinsic analytical sensitivity of the test. The biologic importance of the IgA response in MHS-associated disease and MHS colonization as well as the possibility of improving the detection of IgA generated in response to MHS warrants further investigation.

The overall diagnostic performance of the MHR Vlp and the MHS T20 IgG/IgA ELISAs varied depending on the selected cutoff and the antibody isotype evaluated (Table 2 and 3). A S/P≥0.50 cutoff for MHR Vlp IgG and 0.4 for MHR Vlp IgA ELISAs and S/P≥0.6 for MHS T20 IgG and IgA ELISAs could be selected to ensure 100% diagnostic and analytical specificities while providing high detection rate overtime, with 100% seropositive animals detected for both ELISAs after 24-28 DPI throughout the study.

Previous reports suggested that oral fluids might represent a good alternative to individual animal sampling for monitoring MHR and MHS circulation/colonization in swine populations (Clavijo et al. 2014; Gomes Neto et al. 2015). However, our understanding of the implications that may exist between PCR results from oral fluids and clinical signs was limited due to the lack of well-established infection models for both MHR and MHS. In this study, we successfully developed a CDCD pig model to reproduce swine mycoplasmal arthritis in growing animals under experimental conditions. Most of the inoculated pigs developed clinical signs and pathological lesions consistent with MHR or MHS, respectively. MHR oral fluid shedding was detected at high Cq values (Cq ≥32) across pens throughout the study, suggesting that oral fluids could provide an easier diagnostic sample to determine herd status of colonization. The peak of MHS shedding (100%; DPI 8) coincided with the onset of the clinical signs; however, detection of MHS in oral fluids was limited compared to MHR being undetectable by DPI 14. Overall, the high Cq values obtained with both qPCRs indicated that the analytical sensitivity of current PCR protocols for MHR and MHS DNA detection in oral fluids could be further improved.

The identification of subclinically infected animals and the monitoring of disease progression in clinically affected swine herds is important for disease surveillance and management. Prior to this study, the detection of serum antibody against MHR or MHS has not been proven to correlate with the disease status of individual animals. This study demonstrated that the combined use of two ELISAs based on a chimeric VlpA-G recombinant polypeptide specific of MHR or a cocktail of surface proteins extracted from MHS cultures, respectively, can be used for early detection, monitoring of infection, and differential serodiagnosis of MHR-associated disease and MHS-associated arthritis. Concurrent direct and indirect detection of MHR and MHS by PCR and ELISA, respectively, will provide insight into the dynamics of MEM and MRS infections in swine populations. Therefore, these antemortem diagnostic tools could be used for intervention timing and evaluation of interventions to improve control of WR-associated disease and MHS-associated arthritis.

To the authors' knowledge, this is the first study to reproduce MHS-associated arthritis and MHR-associated disease in growing animals and monitor the clinical progression of MHR- and MRS-associated diseases in relation to the kinetics of the antibody responses in pig serum (ELISA) and bacterial shedding (qPCR) in pen oral fluids collected at different time points during the infection process. In doing so, this study provides not only valid serologic assays but also insights into the infection dynamics of MHR-associated disease and MHS-associated arthritis not previously described.

Example 2

The design and production of a recombinant chimeric Vip A-G (rVlpA-G) polypeptide specific of MHR MhrVlpA-G (see FIG. 1(SEQ ID NO:2 entire chimera)):

```
pET32a
EcoR 1-vlpB-
                                         (SEQ ID NO: 5)
GGGGS -vlpC-vlpD-
                                         (SEQ ID NO: 6)
GGGGS -vlpE-
                                         (SEQ ID NO: 7)
GGGGS -vlpF-
                                         (SEQ ID NO: 8)
GGGGS -vlpG-
                                         (SEQ ID NO: 9)
GGGGS -vlpA-HinDIII
                                        (SEQ ID NO: 10)
GGGGSGTGSDSQDSGAKGTGSDSQDSGAKGGGGSEATPKSPESGSQEAAPKSSESGSQG

GGGSSDSTSTSKEQGSSDSTSTSKEQGSGGGGSDGQHSNPSNPTTSDPKESNPSNPTTSG

GGGSGSTPTPEQGNNQGGSTPTPEQGNNQGGGGGSGSTTESSGQADSASGTSSTTGSGS

TTESSGQADSGGGGSKTENTQQSEAPGT*

Nucleotide sequence (chimera back treanslated)
                                           SEQ ID NO: 1
GGCGGCGGCGGCAGCGGCGGCGGCGGCAGCGGCGGCGGCGGCAGCGGCGGCGGCGGCAGC

GGCGGCGGCGGCAGCGGCGGCGGCGGCAGCGGCACCGGCAGCGACAGCCAGGACAGCGGC
```

```
GCCAAGGGCACCGGCAGCGACAGCCAGGACAGCGGCGCCAAGGGCGGCGGCGGCAGCGAG

GCCACCCCCAAGAGCCCCGAGAGCGGCAGCCAGGAGGCCGCCCCCAAGAGCAGCGAGAGC

GGCAGCCAGGGCGGCGGCGGCAGCAGCGACAGCACCAGCACCAGCAAGGAGCAGGGCAGC

AGCGACAGCACCAGCACCAGCAAGGAGCAGGGCAGCGGCGGCGGCGGCAGCGACGGCCAG

CACAGCAACCCCAGCAACCCCACCACCAGCGACCCCAAGGAGAGCAACCCCAGCAACCCC

ACCACCAGCGGCGGCGGCGGCAGCGGCAGCACCCCCACCCCCGAGCAGGGCAACAACCAG

GGCGGCAGCACCCCCACCCCCGAGCAGGGCAACAACCAGGGCGGCGGCGGCGGCAGCGGC

AGCACCACCGAGAGCAGCGGCCAGGCCGACAGCGCCAGCGGCACCAGCAGCACCACCGGC

AGCGGCAGCACCACCGAGAGCAGCGGCCAGGCCGACAGCGGCGGCGGCGGCAGCAAGACC

GAGAACACCCAGCAGAGCGAGGCCCCCGGCACC
```

An rVlpA-G indirect ELISA based on the rVlpA-G as described in Example 1 was further tested for sensitivity and specificity. The diagnostic performance of the MHR rVlpA-G indirect ELISA (diagnostic sensitivity and specificity) and absence cross-reactivity (analytical specificity) against other members of genus Mycoplasma has been evaluated by testing a panel of samples of precisely known immune status (i.e., Mycoplasma hyohinis, Mycoplasma hyosinoviae, Mycoplasma hyopneumoniae, and Mycoplasma flocculare) generated by experimental inoculation of CDCD pigs with different Mycoplasmas. All animals MHR inoculated showed specific seroconversion between day post-vaccination 14 (IgA) and 28 (IgG). No cross-reactivity (100% analytical specificity) against other member of the genus Mycoplasma was observed under experimental conditions.

SEQUENCE LISTING

```
Sequence total quantity: 5
SEQ ID NO: 1            moltype = DNA  length = 693
FEATURE                 Location/Qualifiers
source                  1..693
                        mol_type = other DNA
                        organism = synthetic construct
SEQUENCE: 1
ggcggcggcg gcagcggcgg cggcggcagc ggcggcggcg gcagcggcgg cggcggcagc  60
ggcggcggcg gcagcggcgg cggcggcagc ggcaccggca gcgacagcca ggacagcggc 120
gccaagggca ccggcagcga cagccaggac agcggcgcca agggcggcgg cggcagcgag 180
gccaccccca agagcccga gagcggcagc caggaggccg cccccaagag cagcgagagc 240
ggcagccagg gcggcggcgg cagcagcgac agcaccagca ccagcaagga gcagggcagc 300
agcgacagca ccagcaccag caaggagcag ggcagcggcg gcggcggcag cgacggccag 360
cacagcaacc cagcaacccc accaccagc gaccccaagg agagcaaccc cagcaacccc 420
accaccagcg gcggcggcgg cagcggcagc accccaccc ccgagcaggg caacaaccag 480
ggcggcagca ccccacccc cgagcagggc aacaaccagg gcggcggcgg cggcagcggc 540
agcaccaccg agagcagcgg ccaggccgac agcgccagcg gcaccagcag caccaccggc 600
agcggcagca ccaccgagag cagcggccag gccgacagcg gcggcggcgg cagcaagacc 660
gagaacaccc agcagagcga ggccccggc acc                               693

SEQ ID NO: 2            moltype = AA  length = 206
FEATURE                 Location/Qualifiers
source                  1..206
                        mol_type = protein
                        organism = synthetic construct
SEQUENCE: 2
GGGGSGTGSD SQDSGAKGTG SDSQDSGAKG GGGSEATPKS PESGSQEAAP KSSESGSQGG   60
GGSSDSTSTS KEQGSSDSTS TSKEQGSGGG GSDGQHSNPS NPTTSDPKES NPSNPTTSGG  120
GGSGSTPTPE QGNNQGGSTP TPEQGNNQGG GGGSGSTTES SGQADSASGT SSTTGSGSTT  180
ESSGQADSGG GGSKTENTQQ SEAPGT                                       206

SEQ ID NO: 3            moltype = DNA  length = 24
FEATURE                 Location/Qualifiers
misc_feature            1..24
                        note = Primer
source                  1..24
                        mol_type = other DNA
                        organism = synthetic construct
SEQUENCE: 3
gcatgttgaa cgggatgtag catt                                          24
```

```
SEQ ID NO: 4              moltype = DNA  length = 29
FEATURE                   Location/Qualifiers
misc_feature              1..29
                          note = Primer
source                    1..29
                          mol_type = other DNA
                          organism = synthetic construct
SEQUENCE: 4
tgaagctgtg aagctccttt ctattactc                                   29

SEQ ID NO: 5              moltype = AA  length = 5
FEATURE                   Location/Qualifiers
REGION                    1..5
                          note = Linker sequence
source                    1..5
                          mol_type = protein
                          organism = synthetic construct
SEQUENCE: 5
GGGGS                                                              5
```

What is claimed is:

1. A chimeric polypeptide comprising two or more Mycoplasma variable surface lipoproteins (Vlp) of VlpA as set forth at residues 194 to 206 of SEQ ID NO: 2, VlpB as set forth at residues 6 to 29 of SEQ ID NO: 2, VlpC as set forth at residues 35 to 58 of SEQ ID NO: 2, VlpD as set forth at residues 64 to 87 of SEQ ID NO: 2, VlpE as set forth at residues 93 to 118 of SEQ ID NO: 2, VlpF as set forth at residues 124 to 149 of SEQ ID NO: 2, and VlpG as set forth at residues 155 to 188 of SEQ ID NO: 2.

2. The chimeric polypeptide of claim 1, wherein the polypeptide comprises each of VlpA, VlpB, VlpC, VlpD, VlpE, VlpF, and VlpG.

3. A vaccine composition comprising the chimeric polypeptide of claim 1.

4. A method of vaccinating a subject against a Mycoplasma infection, the method comprising: administering to the subject an effective dose of the vaccine composition of claim 3.

5. The method of claim 4, wherein the subject is a swine.

6. The chimeric polypeptide of claim 1, wherein the two or more Vlp are separated by an intervening linker.

* * * * *